US007135568B2

(12) United States Patent
Gerlach et al.

(10) Patent No.: US 7,135,568 B2
(45) Date of Patent: Nov. 14, 2006

(54) SUBSTITUTED PYRAZOLOPYRIMIDINES AND THIAZOLOPYRIMIDINES

(75) Inventors: Matthias Gerlach, Brachttal (DE); Corrinna Sundermann, Aachen (DE); Utz-Peter Jagusch, Aachen (DE); Bernd Sundermann, Aachen (DE); Martin Fuhr, Toenisvorst (DE); Adriaan P. Ijzerman, MB Haarlem (NL); Miriam Dissen-De Groote, Middelburg (NL)

(73) Assignee: Gruenenthal GmbH, Aachen (DE)

( * ) Notice: Subject to any disclaimer, the term of this patent is extended or adjusted under 35 U.S.C. 154(b) by 0 days.

(21) Appl. No.: 10/660,794

(22) Filed: Sep. 12, 2003

(65) Prior Publication Data

US 2004/0127508 A1 Jul. 1, 2004

Related U.S. Application Data

(63) Continuation of application No. PCT/EP02/02722, filed on Mar. 13, 2002.

(30) Foreign Application Priority Data

Mar. 14, 2001 (DE) ................. 101 12 197
Oct. 29, 2001 (DE) ................. 101 53 344

(51) Int. Cl.
C07D 471/04 (2006.01)
C07D 513/04 (2006.01)
A61K 31/519 (2006.01)
A61P 25/04 (2006.01)
A61P 25/28 (2006.01)

(52) U.S. Cl. ............. 544/250; 544/278; 544/281; 514/259.2; 514/259.3; 514/267

(58) Field of Classification Search ........... 514/259.2, 514/259.3, 267; 544/281, 278, 250
See application file for complete search history.

(56) References Cited

FOREIGN PATENT DOCUMENTS

DE        10112197 A1    9/2002
WO    WO-02/027585 A3    9/2002

OTHER PUBLICATIONS

Mobius HJ. Int J Geriatr Psychiatry. Sep. 2003;18(Suppl 1):S47-54.*
Lee KR et al, Cerebrovasc Dis. 2001;11(1):20-9, Medline abstract PMID: 11173790.*
Low SJ, Roland CL., Int J Clin Pharmacol Ther. Jan. 2004;42(1):1-14, Medline abstract PMID: 14756381.*
Walters MR, Bradford AP, Fischer J, Lees KR., Br J Clin Pharmacol. Mar. 2002;53(3):305-11.*
West, Anthony R., Solid State Chemistry and its Applications, Wiley, New York, 1988, pp. 358 & 365.*
Coleman, Robert A, "Medicinal Chemistry: Principles and Practice, Chapter 4, Frank D. King ed.", The Royal Society of Chemistry, Cambridge, 1994, pp. 53-58.*
David J.W. Grant, "University of Minnesota—Twin Cities Campus College of Pharmacy, Annual Report", [online] 1999, [retrieved on Feb. 13, 2003]. Retrieved from the internet, <http://www.msi.umn.edu/general/Reports/ar99/departments/pharmacy.html>.*
Vippagunta, S. R. et al, Advanced Drug Delivery Reviews, 48, 3-26, 2001.*
P. Leeson et al. "The Glycine Site on the NMDA Receptor: Structure-Activity Relationships and Therapeutic Potential" *J. Med. Chem.* 37(24):4053-4067.
P. Krogsgaard-Larsen et al. "Design of Excitatory Amino Acid Receptor Agonists, Partial Agonists and Antagonists: Ibotenic Acid as a Key Lead Structure" *Eur. J. Med. Chem.* (1996) 31:515-537.

* cited by examiner

Primary Examiner—Thomas C. McKenzie
(74) Attorney, Agent, or Firm—Crowell & Moring LLP

(57) ABSTRACT

Substituted pyrazolopyrimidines and thiazolopyrimidines, specifically, compounds corresponding to the structure (I A), (I B) or (II)

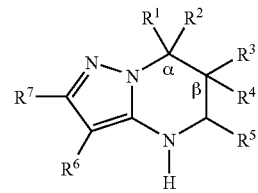

IA

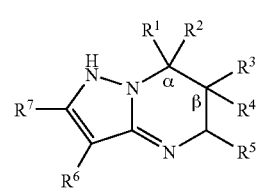

IB

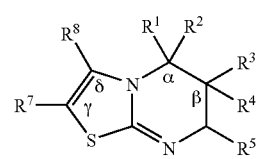

II processes for their preparation, substance libraries containing them, pharmaceutical formulations containing these compounds, the use of these compounds for the production of medicaments for the treatment and/or prophylaxis of pain and related treatment methods are provided.

37 Claims, No Drawings

SUBSTITUTED PYRAZOLOPYRIMIDINES AND THIAZOLOPYRIMIDINES

CROSS-REFERENCE TO RELATED APPLICATIONS

This application is a continuation of International Patent Application No. PCT/EP02/02722, filed Mar. 13, 2002, designating the United States of America, and published in German as WO 02/072585, the entire disclosure of which is incorporated herein by reference. Priority is claimed based on Federal Republic of Germany patent application no. DE 101 12 197.0, filed Mar. 14, 2001, and based on Federal Republic of Germany patent application no. DE 101 53 344.6, filed Oct. 29, 2001.

FIELD OF THE INVENTION

The present invention relates to substituted pyrazolopyrimidines and thiazolopyrimidines, processes for their preparation, substance libraries containing them, medicaments that contain these compounds, the use of these compounds for the production of medicaments for the treatment and/or prophylaxis of pain, epilepsy, schizophrenia, neurodegenerative conditions, in particular Alzheimer's disease, Huntington's disease and Parkinson's disease, cerebral ischaemias and infarcts, psychoses due to raised amino acid levels, cerebral oedemas, insufficiency states of the central nervous system, in particular with hypoxias, especially neonatal hypoxia, and anoxias, AIDS dementia, encephalomyelitis, Tourette's syndrome, perinatal asphyxia, tinnitus, neuropathic pain, respiratory pathway diseases, cancer, cardiac arrhythmias, malfunctions and diseases of the immune system, inflammatory conditions and diseases, neurodegenerative conditions, Parkinson's disease, kidney failure, schizophrenia, sleep disturbances, strokes, thromboses, urinary incontinence, diabetes, psoriasis, septic shock, cerebral traumas, glaucoma and/or congestive insufficiency, as well as pharmaceutical preparations containing these compounds.

BACKGROUND OF THE INVENTION

The treatment of chronic and non-chronic pain conditions is very important in medicine. There is therefore a universal need for highly effective therapies for a patient-friendly and targeted treatment of chronic and non-chronic pain conditions, including the successful and satisfactory treatment of pain on the part of the patient.

Conventional opioids such as morphine are highly effective in treating severe to extremely severe pain. Their use is however limited by the known side effects such as for example respiratory depression, vomiting, sedation, constipation and development of tolerance. Also, they are less effective in treating neuropathic or incidental pain afflicting in particular tumour patients.

Opioids exert their analgesic effect by binding to cell membrane receptors that belong to the family of the so-called G protein-coupled receptors. In addition to these there are further receptors as well as ion channels that are significantly involved in the system of pain generation and pain transmission, for example the N-methyl-D-aspartate ion channel (NMDA ion channel), via which a substantial part of synaptic communication proceeds and through which the calcium ion exchange between a neuronal cell and its environment is controlled (see for example P. D. Leeson, L. L. Iversen, *J. Med. Chem.* 37 (1994) 4053–4067).

Important knowledge concerning the physiological importance of ion channel selective substances has been made possible by the development of the patch-clamp technique, by means of which the effect of NMDA antagonists (i.e. antagonists of the NMDA ion channel) on the calcium level in the cell interior can be detected.

In the unactivated state the NMDA ion channels are in each case closed by individual magnesium ions that are present in the interior of the channel and cannot pass through the latter on account of their size. In the activated state the smaller calcium and sodium ions can pass through the channel. The (+)-MK801 binding site of the NMDA ion channel (ionotropic NMDA receptor) is also present in the interior of this membrane protein. Substances with an NMDA antagonistic action, such as phencyclidine (PCP), ketamine or MK801, occupy this binding site (so-called "channel blockers") and accordingly close the relevant NMDA ion channel.

SUMMARY OF THE INVENTION

One object of the present invention is to provide analgesically active compounds that are suitable for relieving pain and possibly also for relieving chronic and neuropathic pain. In addition these substances should as far as possible produce none of the side effects that normally occur when using opioids such as morphine, for example nausea, vomiting, dependence, respiratory depression or constipation.

This object is achieved by the compounds of the general structure (I A), (I B) and (II), which are analgesically active and bind to the MK801 binding site of the NMDA receptor. The compounds according to the invention are substituted pyrazolopyrimidines and thiazolopyrimidines of the general structure (I A), (I B) or (II)

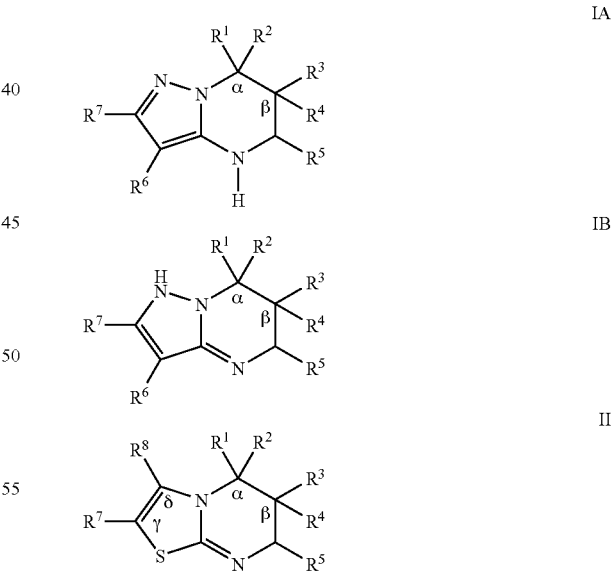

wherein
$R^1$ and $R^2$ independently of one another denote H, O—$R^9$, S—$R^{10}$, $C_{1-12}$-alkyl, $C_{3-8}$-cycloalkyl, —$CH_2$—$C_{3-8}$-cycloalkyl, aryl, —($C_{1-6}$-alkyl)-aryl, heterocyclyl or —($C_{1-6}$-alkyl)-heterocyclyl,
  in which one of the radicals $R^1$ and $R^2$ is H and the other radical of $R^1$ and $R^2$ is not H, or in the case that one of the radicals R¹ and R² denotes aryl, the other radical of R¹ and R² denotes H or $C_{1-12}$-alkyl, R³ and R⁴ denote H, $C_{1-12}$-alkyl, $C_{3-8}$-cycloalkyl, —$CH_2$—$C_{3-8}$-cycloalkyl, aryl or —($C_{1-6}$-alkyl)-aryl in which at least one of the radicals R³ and R⁴ is H, or one of the radicals R¹ and R² together with one of the radicals R³ and R⁴ forms W, where W denotes α'-$(CH_2)_n$-β' where n=3, 4, 5 or 6, α'-CH=CH—$CH_2$-β', α'-$CH_2$—CH=CH-β', α'-CH=CH—$CH_2$—$CH_2$-β', α'-$CH_2$—CH=CH—$CH_2$-β', α'-$CH_2$—$CH_2$—CH=CH-β',

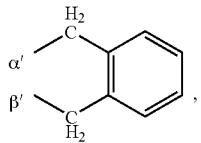

α'-O—$(CH_2)_m$-β' where m=2, 3, 4 or 5,

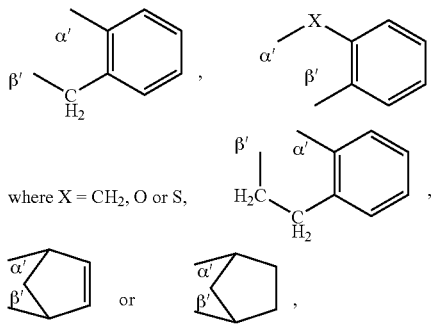

where X = $CH_2$, O or S, the end of W identified by α' is joined to the atom of the compound of the general structure (I A), (I B) or (II) identified by α, and the end of W identified by β' is joined to the atom of the compound of the general structure (I A), (I B) or (II) identified by β, the other radical of R¹ and R² is H or $C_{1-12}$-alkyl, and the other radical of R³ and R⁴ is H or $C_{1-12}$-alkyl;

R⁵ denotes $C_{1-12}$-alkyl, $C_{3-8}$-cycloalkyl, —$CH_2$—$C_{3-8}$-cycloalkyl, aryl, —($C_{1-6}$ alkyl)-aryl, heterocyclyl, —($C_{1-6}$ alkyl)-heterocyclyl or C(=O)$R^{11}$;

R⁶ denotes H, $C_{1-8}$-alkyl, —CN, fluorine, chlorine, bromine, iodine, $NO_2$, $NH_2$, $NHR^{12}$, $NR^{13}R^{14}$, $OR^{15}$, $S(O)_pR^{16}$ where p=0, 1 or 2, —C(=O)$R^{17}$ or —N=N-aryl;

R⁷ denotes H, $C_{1-8}$-alkyl, aryl, —CN, fluorine, chlorine, bromine, iodine, $NO_2$, $NH_2$, $NHR^{12}$, $NR^{13}R^{14}$, $OR^{18}$, $S(O)_qR^{19}$ where q=0, 1 or 2 or denotes C(=O)$R^{20}$;

R⁸ denotes H, $C_{1-8}$-alkyl or aryl, or the radicals R⁷ and R⁸ together form Y, where Y denotes γ'-$CR^{21}$=$CR^{22}$—$CR^{23}$=$CR^{24}$-δ' and the end of Y identified by γ' is joined to the atom of the general structure (II) identified by γ, and the end of Y identified by δ' is joined to the atom of the general structure (II) identified by δ;

R⁹ and $R^{10}$ independently of one another denote H, $C_{1-8}$-alkyl, $C_{3-8}$-cycloalkyl, —$CH_2$—$C_{3-8}$-cycloalkyl, aryl or —($C_{1-6}$-alkyl)-aryl;

$R^{11}$ denotes H, $C_{1-8}$-alkyl, $C_{3-8}$-cycloalkyl, —$CH_2$—$C_{3-8}$-cycloalkyl, aryl or $OR^{25}$;

$R^{12}$ denotes $C_{1-6}$-alkyl or —$CH_2$-aryl;

$R^{13}$ and $R^{14}$ are identical or different $C_{1-6}$-alkyl or together denote —$(CH_2)_h$— where h=4 or 5;

$R^{15}$ and $R^{16}$ independently of one another denote H, $C_{1-8}$-alkyl, $C_{3-8}$-cycloalkyl, —$CH_2$—$C_{3-8}$-cycloalkyl, aryl or —($C_{1-6}$-alkyl)-aryl;

$R^{17}$ denotes H, $C_{1-8}$-alkyl, $C_{3-8}$-cycloalkyl, —$CH_2$—$C_{3-8}$-cycloalkyl, aryl, —($C_{1-6}$-alkyl)-aryl, $NH_2$, $NHR^{12}$, $NR^{13}R^{14}$ or $OR^{26}$;

$R^{18}$ and $R^{19}$ independently of one another denote H, $C_{1-8}$-alkyl, $C_{3-8}$-cycloalkyl, —$CH_2$—$C_{3-8}$-cycloalkyl, aryl or —($C_{1-6}$-alkyl)-aryl;

$R^{20}$ denotes H, $C_{1-8}$-alkyl, $C_{3-8}$-cycloalkyl, —$CH_2$—$C_{3-8}$-cycloalkyl, aryl or —($C_{1-6}$-alkyl)-aryl or $OR^{27}$;

$R^{21}$, $R^{22}$, $R^{23}$ and $R^{24}$ independently of one another denote H, fluorine, chlorine, bromine, iodine or $OR^{28}$;

$R^{25}$, $R^{26}$, $R^{27}$ and $R^{28}$ independently of one another denote H or $C_{1-6}$-alkyl, where $R^{25}$ does not denote H if simultaneously R¹ denotes aryl and R² denotes alkyl.

DETAILED DESCRIPTION OF THE EMBODIMENTS

The compounds according to the invention of the general structure (I A), (I B) or (II) in the represented form or in the form of their acid(s) or their base(s) or in the form of one of their salts, in particular one of their physiologically compatible salts, or in the form of one of their solvates, in particular the hydrates; in the form of their racemate, in the form of the pure stereoisomers, in particular enantiomers or diastereomers, or in the form of mixtures of the stereoisomers, in particular of the enantiomers or diastereomers, are present in an arbitrary mixture ratio. The compounds according to the invention, in particular the pyrazolopyrimidines (I) according to the invention, may be present in tautomeric forms, in the case of (I) in the forms (I A) and (I B), wherein the optionally preferred tautomeric form may vary from compound to compound and for example depending on the aggregate state or on the chosen solvent.

The following compounds of the general structure (I A), (I B) or (II) are already known in the prior art, though their use has not been described in a medicament or for the production of a medicament for the treatment and/or prophylaxis of pain, epilepsy, schizophrenia, neurodegenerative conditions, in particular Alzheimer's disease, Huntington's disease and Parkinson's disease, cerebral ischaemias and infarcts, psychoses due to raised amino acid levels, cerebral oedemas, insufficiency states of the central nervous system, in particular in hypoxias and anoxias, AIDS dementia, encephalomyelitis, Tourette's syndrome, perinatal asphyxia and tinnitus:

4,5,6,7-tetrahydro-2-methyl-5,7-diphenylpyrazolo[1,5-a] pyrimidine, 4,5,6,7-tetrahydro-2,5-dimethyl-7-phenylpyrazolo[1,5-a]pyrimidine, 4,5,6,7-tetrahydro-5,7-dimethyl-3-phenylpyrazolo[1,5-a]pyrimidine, 4,5,6,7-tetrahydro-2,5,7-trimethylpyrazolo[1,5-a]pyrimidine, 4,5,6,7-tetrahydro-5,7-dimethyl-2-phenylpyrazolo[1,5-a] pyrimidine (B. Koren et al., Tetrahedron (1976) 32, 493–497;

4,5,6,7-tetrahydro-2-methyl-5,7-di-n-propylpyrazolo[1,5-a] pyrimidine-3-carbonitrile, 4,5,6,7-tetrahydro-5-methyl-7-[3-(trifluoromethyl)-phenyl]pyrazolo[1,5-a]pyrimidine-3-carbonitrile, 7-[4-chloro)-phenyl]-4,5,6,7-tetrahydro-5-methylpyrazolo[1,5-a]pyrimidine-3-carbonitrile, 7-[3-chloro)-phenyl]-4,5,6,7-tetrahydro-5-methylpyrazolo[1, 5-a]pyrimidine-3-carbonitrile (EP 0 264 773 A1);

3,4-dihydro-2-(4-nitrophenyl)-4-phenyl-2H-pyrimido[2,1-b]benzothiazole, 3,4-dihydro-4-(4-methylphenyl)-2-(4- nitrophenyl)-2H-pyrimido[2,1-b]benzothiazole (M. A. Abdel-Rahman et al., CA (1995) 796768 [Rev. Roum. Chim. (1995) 42, 165–172]).

These compounds are therefore also the subject of the present invention, as are processes according to the invention for their preparation, substance libraries or medicaments containing them, as well as their use for the production of medicaments for the treatment and/or prophylaxis of pain, epilepsy, schizophrenia, neurodegenerative conditions, in particular Alzheimer's disease, Huntington's disease and Parkinson's disease, cerebral ischaemias and infarcts, psychoses due to raised amino acid levels, cerebral oedemas, insufficiency states of the central nervous system, especially in hypoxias and anoxias, AIDS dementia, encephalomyelitis, Tourette's syndrome, perinatal asphyxia and tinnitus, as well as further medical conditions mentioned in this disclosure.

The terms "alkyl", "$C_{1-12}$-alkyl", "$C_{1-8}$-alkyl" and "$C_{1-6}$-alkyl" include within the scope of the present invention acyclic saturated or unsaturated hydrocarbon radicals that may be branched or straight-chain as well as unsubstituted or singly substituted or multiply identically or differently substituted with (as in the case of $C_{1-12}$-alkyl) 1 to 12 (i.e. 1, 2, 3, 4, 5, 6, 7, 8, 9, 10, 11 or 12), with (as in the case of $C_{1-12}$-alkyl) 1 to 8 (i.e. 1, 2, 3, 4, 5, 6, 7 or 8) or with (as in the case of $C_{1-6}$-alkyl) 1 to 6 (i.e. 1, 2, 3, 4, 5 or 6) C atoms, i.e. $C_{1-12}$-alkanyls, $C_{1-8}$-alkanyls or $C_{1-6}$-alkanyls, $C_{2-12}$-alkenyls, $C_{2-8}$-alkenyls or $C_{2-6}$-alkenyls, and $C_{2-12}$-alkinyls, $C_{2-8}$-alkinyls or $C_{2-6}$-alkinyls. In this connection "alkinyls" have at least one C—C double bond, and "alkinyls" have at least one C—C triple bond. Preferably alkyl is selected from the group comprising methyl, ethyl, n-propyl, 2-propyl, n-butyl, isobutyl, sec.-butyl, tert.-butyl, n-pentyl, isopentyl, neopentyl, n-hexyl, 2-hexyl, n-heptyl, n-octyl, n-nonyl, n-decyl, n-dodecyl; ethenyl (vinyl), ethinyl, propenyl (—CH$_2$CH=CH$_2$, —CH=CH—CH$_3$, —C(=CH$_2$)—CH$_3$), propinyl (—CH$_2$—C≡CH, —C≡C—CH$_3$), butenyl, butinyl, pentenyl, pentinyl, hexenyl, hexinyl, octenyl and octinyl. "$C_{3-8}$-cycloalkyl" (or "cycloalkyl") denotes within the context of the present invention a cyclic saturated or unsaturated hydrocarbon radical with 3, 4, 5, 6, 7 or 8 C atoms, in which the radical may be unsubstituted or singly substituted or multiply identically or differently substituted and may optionally be benzo-condensed. Cycloalkyl denotes for example cyclopropyl, cyclobutyl, cyclopentyl, cyclohexyl, cycloheptyl, cyclooctyl, cyclopentenyl, cyclohexenyl, cycloheptenyl and cyclooctenyl. For the purposes of the present invention the following are particularly preferred: cyclopropyl, cyclopropyl-2-carboxylic acid, cyclopropyl-2-carboxylic acid ethyl ester and cyclohexyl.

For the purposes of the present invention the expression "aryl" is understood to denote a radical that is selected from the group comprising phenyl, naphthyl, anthracenyl and biphenyl, and is unsubstituted or is singly or multiply identically or differently substituted. The aryl radicals may also be condensed with further saturated, (partially) unsaturated or aromatic ring systems. Each aryl radical may be present unsubstituted or singly or multiply substituted, in which the aryl substituents may be identical or different and may be in any arbitrary position of the aryl radical. Advantageously aryl denotes aryl', which includes aryl$^1$, aryl$^2$ and aryl$^3$. In this connection aryl$^1$ denotes

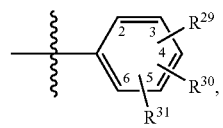

aryl$^2$ denotes

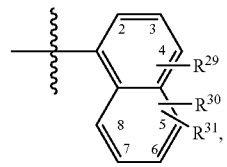

and aryl$^3$ denotes

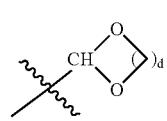

wherein $R^{29}$, $R^{30}$ and $R^{31}$ independently of one another denote H, —$C_{1-6}$-alkyl, $C_{3-8}$-cycloalkyl, —($C_{1-6}$ alkyl)-$C_{3-8}$-cycloalkyl, aryl, ($C_{1-6}$ alkyl)-aryl, heterocyclyl, —($C_{1-6}$ alkyl)-heterocyclyl, F, Cl, Br, I, —CN, —NC, —OR$^{32}$, —SR$^{33}$, —NO, —NO$_2$, NH$_2$, NHR$^{34}$, NR$^{35}$R$^{36}$, —N—OH, —N—OC$_{1-6}$-alkyl, —NHNH$_2$, —N=N-aryl, —(C=O)R$^{37}$, where d=1, 2 or 3, or denote —(C=S)R$^{37}$, and may be in any arbitrary ring position;

$R^{32}$ and $R^{33}$ independently of one another denote H, —$C_{1-6}$-alkyl, —$C_{3-8}$-cycloalkyl, —($C_{1-6}$-alkyl)-$C_{3-8}$-cycloalkyl, -aryl, —($C_{1-6}$-alkyl)-aryl, -heterocyclyl, —($C_{1-6}$-alkyl)-heterocyclyl, (C=O)R$^{38}$, —[(CH$_2$)$_w$—O]$_z$—H or —[(CH$_2$)$_w$—O]$_z$—C$_{1-6}$-alkyl where w=1, 2, 3 or 4 and z=1, 2, 3, 4 or 5;

$R^{34}$ denotes $C_{1-6}$-alkyl, —CH$_2$-aryl or —(C=O)O-tert.-butyl;

$R^{35}$ and $R^{36}$ independently of one another denote $C_{1-6}$-alkyl or together denote —(CH$_2$)—$_g$ where g=4 or 5;

$R^{37}$ denotes H, —$C_{1-6}$-alkyl, —$C_{3-8}$-cycloalkyl, —($C_{1-6}$-alkyl)—$C_{3-8}$-cycloalkyl, -aryl, —($C_{1-6}$-alkyl)-aryl, -heterocyclyl, —($C_{1-6}$-alkyl)-heterocyclyl, —OR$^{39}$, —NH$_2$, —NHR$^{34}$, —NR$^{35}$R$^{36}$;

$R^{38}$ denotes H, —$C_{1-6}$-alkyl, —$C_{3-8}$-cycloalkyl, —($C_{1-6}$-alkyl)—$C_{3-8}$-cycloalkyl, -aryl, —($C_{1-6}$-alkyl)-aryl; and $R^{39}$ denotes H, —$C_{1-6}$-alkyl, —$C_{3-8}$-cycloalkyl, —($C_{1-6}$-alkyl)—$C_{3-8}$-cycloalkyl, -aryl, —($C_{1-6}$-alkyl)-aryl, -heterocyclyl or —($C_{1-6}$-alkyl)-heterocyclyl.

Particularly preferred aryl radicals for the purposes of the invention are phenyl, 3-fluorophenyl, 3-bromophenyl, 4-bromophenyl, 4-chlorophenyl, 4-fluorophenyl, 3-methylphenyl, 4-methylphenyl, 4-hydroxyphenyl, 4-methoxyphenyl, 2,4-dimethylphenyl, 3,4-dimethoxyphenyl, 2,3,4-trimethoxyphenyl, 2-naphthyl, 4-trifluorophenyl, 4-phenoxyphenyl, 2-hydroxy-3-methoxyphenyl, 4-hydroxy-3-methoxyphenyl and 3-carboxy-2-hydroxyphenyl.

The expression "heterocyclyl" denotes a monocyclic or polycyclic organic radical in which at least one ring contains 1 heteroatom or 2, 3, 4 or 5 identical or different heteroatoms that is/are selected from the group comprising N, O and S, wherein the radical is saturated or unsaturated, and is unsubstituted or singly substituted or multiply identically or differently substituted. Examples of heterocyclyl radicals within the scope of the present invention are monocyclic 5-membered, 6-membered or 7-membered organic radicals containing 1 heteroatom or 2, 3, 4 or 5 identical or different heteroatoms that is/are nitrogen, oxygen and/or sulfur, and their benzo-condensed analogues. The "heteroaryl" radicals form a subgroup of the heterocyclyl radicals, and comprise those heterocyclyl radicals in which the at least one ring that contains the heteroatom(s) is heteroaromatic. Each heteroaryl radical may be present unsubstituted or singly substituted or multiply identically or differently substituted. Examples of heterocyclyl radicals within the context of the present invention are pyrrolidinyl, tetrahydrofuryl, piperidinyl, piperazinyl and in particular morpholinyl. Examples of heterocyclyl radicals that are at the same time heteroaryl radicals are pyrrolyl, pyrazolyl, imidazolyl, pyridazinyl, pyrimidinyl, pyrazinyl and in particular furanyl, thienyl and pyridinyl as well as their benzo-condensed analogues. All these radicals may in each case be present unsubstituted or singly or multiply, identically or differently substituted.

The expressions "($C_{1-6}$-alkyl)-$C_{3-8}$-cycloalkyl", "($C_{1-6}$-alkyl)-heterocyclyl" and "($C_{1-6}$-alkyl)-aryl" denote, for the purposes of the present invention, that the cycloalkyl, heterocyclyl or aryl radical is bound via a $C_{1-6}$-alkyl group to the compound with which it is substituted. The same comments apply to the expression "$CH_2$—$C_{3-8}$-cycloalkyl".

In connection with the expressions "alkyl", "alkanyl", "alkenyl", "alkinyl" and "cycloalkyl", the term "substituted" within the meaning of the present invention is understood to mean the replacement of a hydrogen atom by for example F, Cl, Br, I, —CN, —NC, $NH_2$, NH-alkyl, NH-aryl, NH-alkyl-aryl, NH-heterocyclyl, NH-alkyl-OH, N(alkyl)$_2$, N(alkyl-aryl)$_2$, N(heterocyclyl)$_2$, N(alkyl-OH)$_2$, NO, $NO_2$, SH, S-alkyl, S-aryl, S-alkyl-aryl, S-heterocyclyl, S-alkyl-OH, S-alkyl-SH, OH, O-alkyl, O-aryl, O-alkyl-aryl, O-heterocyclyl, O-alkyl-OH, CHO, C(=O)$C_{1-6}$-alkyl, C(=S)$C_{1-6}$-alkyl, C(=O)aryl, C(=S)aryl, C(=O)$C_{1-6}$-alkyl-aryl, C(=S)$C_{1-6}$-alkyl-aryl, C(=O)-heterocyclyl, C(=S)-heterocyclyl, $CO_2H$, $CO_2$-alkyl, $CO_2$-alkyl-aryl, C(=O)$NH_2$, C(=O)NH-alkyl, C(=O)NH-aryl, C(=O)NH-heterocyclyl, C(=O)N(alkyl)$_2$, C(=O)N(alkyl-aryl)$_2$, C(=O)N(heterocyclyl)$_2$, SO-alkyl, $SO_2$-alkyl, $SO_2$-alkyl-aryl, $SO_2NH_2$, $SO_3H$, $SO_3$-alkyl, cycloalkyl, aryl or heterocyclyl, in which multiply substituted radicals are understood to mean those radicals that are multiply substituted, e.g. doubly or triply substituted, either on different atoms or on the same atom, for example triply substituted on the same C atom as in the case of $CF_3$ or —$CH_2CF_3$, or at different positions, as in the case of —CH(OH)—CH=CCl—$CH_2$Cl. The multiple substitution may be carried out with the same or with different substituents. Particularly preferred for the purposes of the present invention are $CF_3$ and $CH_2$—$CH_2$—OH as substituted alkyl as well as cyclopropyl-2-carboxylic acid and cyclopropyl-2-carboxylic acid ethyl ester as substituted cycloalkyl.

With reference to "aryl", "heterocyclyl" as well as "heteroaryl", within the context of the present invention the term "singly substituted" or "multiply substituted" is understood to denote the single or multiple substitution, e.g. double, triple or fourfold substitution, of one or more hydrogen atoms of the ring system by a suitable substituent. Insofar as the meaning of this suitable substituent in connection with "aryl", "heterocyclyl" or "heteroaryl" is not defined in another place in the description or in the claims, suitable substituents are F, Cl, Br, I, —CN, —NC, $NH_2$, NH-alkyl, NH-aryl, NH-alkyl-aryl, NH-heterocyclyl, NH-alkyl-OH, N(alkyl)$_2$, N(alkyl-aryl)$_2$, N(heterocyclyl)$_2$, N(alkyl-OH)$_2$, NO, $NO_2$, SH, S-alkyl, S-cycloalkyl, S-aryl, S-alkyl-aryl, S-heterocyclyl, S-alkyl-OH, S-alkyl-SH, OH, O-alkyl, O-cycloalkyl, O-aryl, O-alkyl-aryl, O-heterocyclyl, O-alkyl-OH, CHO, C(=O)$C_{1-6}$-alkyl, C(=S)$C_{1-6}$-alkyl, C(=O)aryl, C(=S)aryl, C(=O)$C_{1-6}$-alkyl-aryl, C(=S)$C_{1-6}$-alkyl-aryl, C(=O)-heterocyclyl, C(=S)-heterocyclyl, $CO_2H$, $CO_2$-alkyl, $CO_2$-alkyl-aryl, C(=O)$NH_2$, C(=O)NH-alkyl, C(=O)NH-aryl, C(=O)NH-heterocyclyl, C(=O)N(alkyl)$_2$, C(=O)N(alkyl-aryl)$_2$, C(=O)N(heterocyclyl)$_2$, S(O)-alkyl, S(O)-aryl, $SO_2$-alkyl, $SO_2$-aryl, $SO_2NH_2$, $SO_3H$, $CF_3$, =O, =S, alkyl, cycloalkyl, aryl and/or heterocyclyl; on one or optionally various atoms (in which connection a substituent may optionally in turn be substituted). The multiple substitution is performed with the same or with different substituents.

"Benzo-condensed" denotes for the purposes of the present invention that a benzene ring is condensed onto another ring.

Pharmaceutically acceptable or physiologically compatible salts within the context of the present invention are those salts of the compounds according to the invention according to the general structure (I A), (I B) and/or (II) that when used for pharmaceutical purposes, especially in mammals and/or humans, are physiologically compatible. Such pharmaceutically acceptable salts may be formed for example with inorganic or organic acids, or in the case where the compounds according to the invention are carboxylic acids, may be formed with bases.

Preferably the pharmaceutically acceptable salts of the compounds according to the invention according to the general structure (I A), (I B) or (II) are formed with hydrochloric acid, hydrobromic acid, sulfuric acid, phosphoric acid, methanesulfonic acid, p-toluenesulfonic acid, carbonic acid, formic acid, acetic acid, oxalic acid, succinic acid, tartaric acid, mandelic acid, fumaric acid, lactic acid, citric acid, glutamic acid or aspartic acid. If the compounds according to the invention are carboxylic acids, the pharmaceutically acceptable salts may also be formed by reaction with bases, such as for example sodium hydrogen carbonate or sodium carbonate. The salts that are formed include, inter alia, hydrochlorides, hydrobromides, phosphates, carbonates, hydrogen carbonates, formates, acetates, oxalates, succinates, tartrates, fumarates, citrates and glutamates or sodium salts. Particularly preferred are the hydrochlorides. Also preferred are the hydrates of the compounds according to the invention, which may be obtained for example by crystallisation from aqueous solution.

All compounds according to the invention contain at least one asymmetry centre, namely the carbon atom of the structure (I A), (I B) or (II) substituted by $R^5$. Accordingly the compounds according to the invention according to the general structure (I A), (I B) or (II) may be present in the form of their racemates, in the form of the pure enantiomers and/or diastereomers or in the form of mixtures of these enantiomers and/or diastereomers, and more specifically both as the substance per se as well as pharmaceutically acceptable salts of these compounds. The mixtures may be present in any arbitrary mixture ratio of the stereoisomers. Preferably the compounds of the general structure (I A), (I B) or (II) are present as enantiomer-pure compounds.

Preferred are those compounds of the general formulae (I A), (I B) or (II) or their pharmaceutically acceptable salts in which $R^1$ and $R^2$ independently of one another denote H, O—$R^9$, S—$R^{10}$, $C_{1-6}$-alkyl, aryl' or —($C_{1-6}$-alkyl)-aryl', wherein the aryl' substituents $R^{29}$, $R^{30}$ and $R^{31}$ independently of one another denote H, $C_{1-6}$-alkyl, F, Cl, Br, I, OH, O—$C_{1-6}$-alkyl, O-aryl¹ or O—$CH_2$-aryl¹, wherein one of the radicals $R^1$ and $R^2$ is H and the other radical of $R^1$ and $R^2$ is not H, or in the case that one of the radicals $R^1$ and $R^2$ denotes aryl', the other radical of $R^1$ and $R^2$ denotes H or $C_{1-6}$-alkyl, $R^3$ and $R^4$ denote H, unsubstituted or singly substituted or multiply identically or differently substituted methyl, ethyl, n-propyl, 2-propyl, n-butyl, isobutyl, sec.-butyl, tert.-butyl, n-amyl, isoamyl, sec.-amyl, n-hexyl, isohexyl, sec.-hexyl, aryl' or —$CH_2$-aryl', wherein at least one of the radicals $R^3$ and $R^4$ is H, or one of the radicals $R^1$ and $R^2$ together with one of the radicals $R^3$ and $R^4$ forms W, where W denotes α'-CH=CH—$CH_2$-β', α'-CH=CH—$CH_2$—$CH_2$-β', α'-O—$(CH_2)_m$-β' where m=2, 3, 4 or 5,

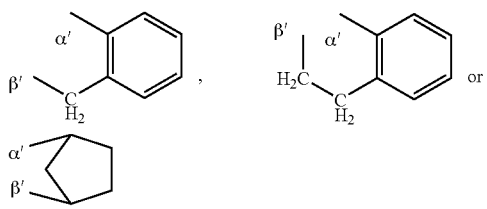

the end of W identified by α' is joined to the atom of the compound of the general structure (I A), (I B) or (II) identified by α, and the end of W identified by β' is joined to the atom of the general structure (I A), (I B) or (II) identified by β, the other radical of $R^1$ and $R^2$ is H or methyl, ethyl, n-propyl, 2-propyl, n-butyl, isobutyl, sec.-butyl, tert.-butyl, n-amyl, isoamyl, sec.-amyl, n-hexyl, isohexyl or sec.-hexyl and the other radical of $R^3$ and $R^4$ denotes H or methyl, ethyl, n-propyl, 2-propyl, n-butyl, isobutyl, sec.-butyl, tert.-butyl, n-amyl, isoamyl, sec.-amyl, n-hexyl, isohexyl, sec.-hexyl;

$R^5$ denotes methyl, ethyl, n-propyl, 2-propyl, n-butyl, isobutyl, sec.-butyl, tert.-butyl, n-amyl, isoamyl, sec.-amyl, n-hexyl, isohexyl, sec.-hexyl, cyclopropyl, cyclobutyl, cyclopentyl, cyclohexyl or cycloheptyl that in each case is unsubstituted or singly substituted or multiply identically or differently substituted, or denotes aryl' or —$(CH_2)_k$-aryl', where k=1, 2, 3 or 4, heterocyclyl or C(=O)$R^{11}$;

$R^6$ denotes H, methyl, ethyl, —CN, fluorine, chlorine, bromine, iodine, —C(=O)$R^{17}$ or —N=N-aryl¹;

$R^7$ denotes H, aryl¹, O$R^{18}$, S(O)$_q R^{19}$, where q=0, 1 or 2, or denotes unsubstituted or singly substituted or multiply identically or differently substituted methyl, ethyl, n-propyl, 2-propyl, n-butyl, isobutyl, sec.-butyl, tert.-butyl, n-amyl, isoamyl, sec.-amyl, n-hexyl, isohexyl or sec.-hexyl, $R^8$ denotes H or aryl', or the radicals $R^7$ and $R^8$ together form Y, where Y denotes γ'-$CR^{21}$=$CR^{22}$—$CR^{23}$=$CR^{24}$-δ' and the end of Y identified by γ' is joined to the atom of the general structure (II) identified by γ, and the end of Y identified by δ' is joined to the atom of the general structure (II) identified by δ;

$R^9$ denotes unsubstituted or singly substituted or multiply identically or differently substituted methyl, ethyl, n-propyl, 2-propyl, n-butyl, isobutyl, sec.-butyl, tert.-butyl, n-amyl, isoamyl, sec.-amyl, n-hexyl, isohexyl, sec.-hexyl, cyclopropyl, cyclobutyl, cyclopentyl, cyclohexyl or cycloheptyl or denotes —$[(CH_2)_r$—O$]_s$—H where r=1, 2, 3, 4, 5 or 6 and s=1, 2, 3, 4, 5 or 6;

$R^{10}$ denotes aryl';

$R^{11}$ denotes aryl' or O$R^{25}$;

$R^{17}$ denotes O$R^{26}$;

$R^{18}$ denotes H or methyl;

$R^{19}$ denotes H, aryl¹, or in each case unsubstituted, singly substituted or multiply identically or differently substituted methyl, ethyl, n-propyl, 2-propyl, n-butyl, isobutyl, sec.-butyl, tert.-butyl, n-amyl, isoamyl, sec.-amyl, n-hexyl, isohexyl or sec.-hexyl;

$R^{21}$, $R^{22}$, $R^{23}$ and $R^{24}$ independently of one another denote H, fluorine, chlorine, bromine, iodine or O$R^{28}$;

$R^{25}$ denotes H, methyl, ethyl, n-propyl, 2-propyl, n-butyl, isobutyl, sec.-butyl, tert.-butyl, n-amyl, isoamyl, sec.-amyl, n-hexyl, isohexyl or sec.-hexyl, where $R^{25}$ does not denote H if at the same time $R^1$ denotes aryl and $R^2$ denotes alkyl;

$R^{26}$ denotes H, methyl, ethyl, n-propyl, 2-propyl, n-butyl, isobutyl, sec.-butyl, tert.-butyl, n-amyl, isoamyl, sec.-amyl, n-hexyl, isohexyl or sec.-hexyl; and $R^{28}$ denotes H, methyl or ethyl;

Heterocyclyl denotes furan-2-yl, furan-3-yl, thien-2-yl, thien-3-yl, pyridin-2-yl, pyridin-3-yl or pyridin-4-yl, where furanyl, thienyl and pyridinyl are in each case unsubstituted or singly substituted or multiply identically or differently substituted;

Aryl' denotes aryl¹, aryl² or aryl³;

Aryl¹ denotes

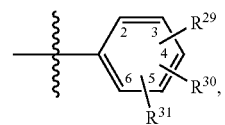

Aryl² denotes

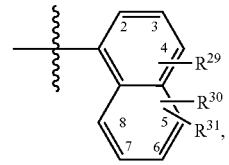

Aryl³ denotes

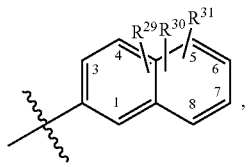

$R^{29}$, $R^{30}$ and $R^{3}$ independently of one another denote H, $C_{1-6}$-alkyl, $C_{3-8}$-cycloalkyl, $(C_{1-6}$ alkyl$)$-$C_{3-8}$-cycloalkyl, aryl, $(C_{1-6}$-alkyl$)$-aryl, heterocyclyl, $(C_{1-6}$ alkyl$)$-heterocyclyl, F, Cl, Br, I, —CN, —NC, —$OR^{32}$, —$SR^{33}$, —NO, —$NO_2$, $NH_2$, $NHR^{34}$, $NR^{35}R^{36}$, —N—OH, —N—$OC_{1-6}$-alkyl, —$NHNH_2$, —N=N-aryl, —(C=O)$R^{37}$,

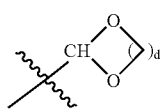

where d=1, 2 or 3, or denotes —(C=S)$R^{37}$, and may be in any arbitrary ring position;

$R^{32}$ and $R^{33}$ independently of one another denote H, —$C_{1-6}$-alkyl, —$C_{3-8}$-cycloalkyl, —$(C_{1-6}$-alkyl$)$-$C_{3-8}$-cycloalkyl, -aryl, —$(C_{1-6}$-alkyl$)$-aryl, -heterocyclyl, —$(C_{1-6}$-alkyl$)$-heterocyclyl, $(C=O)R^{38}$, —$[(CH_2)_w$—O$]_z$—H or —$[(CH_2)_w$—O$]_z$—$C_{1-6}$-alkyl where w=1, 2, 3 or 4 and z=1, 2, 3, 4 or 5;

$R^{34}$ denotes $C_{1-6}$-alkyl, —$CH_2$-aryl or —(C=O)O-tert.-butyl;

$R^{35}$ and $R^{36}$ independently of one another denote $C_{1-6}$-alkyl or together denote —$(CH_2)$—$_g$ where g=4 or 5;

$R^{37}$ denotes H, —$C_{1-6}$-alkyl, —$C_{3-8}$-cycloalkyl, —$(C_{1-6}$-alkyl$)$-$C_{3-8}$-cycloalkyl, -aryl, —$(C_{1-6}$-alkyl$)$-aryl, -heterocyclyl, —$(C_{1-6}$-alkyl$)$-heterocyclyl, —$OR^{39}$, —$NH_2$, —$NHR^{34}NR^{35}R^{36}$;

$R^{38}$ denotes H, —$C_{1-6}$-alkyl, —$C_{3-8}$-cycloalkyl, —$(C_{1-6}$-alkyl$)$-$C_{3-8}$-cycloalkyl, -aryl, —$(C_{1-6}$-alkyl$)$-aryl; and $R^{39}$ denotes H, —$C_{1-6}$-alkyl, —$C_{3-8}$-cycloalkyl, —$(C_{1-6}$-alkyl$)$-$C_{3-8}$-cycloalkyl, -aryl, —$(C_{1-6}$-alkyl$)$-aryl, -heterocyclyl or —$(C_{1-6}$-alkyl$)$-heterocyclyl.

Among these compounds those are particularly preferred in which $R^{1}$ and $R^{2}$ independently of one another denote H, O—$R^{9}$, S—$R^{10}$, unsubstituted or singly substituted or multiply identically or differently substituted methyl, ethyl, n-propyl, 2-propyl, n-butyl, tert.-butyl or n-hexyl, aryl' or —$CH_2$-aryl', where the aryl' substituents $R^{29}$, $R^{30}$ and $R^{31}$ independently of one another denote H, methyl, ethyl, 2-propyl, n-butyl, tert.-butyl, n-hexyl, F, Cl, Br, I, OH, O-methyl, O-ethyl, wherein one of the radicals $R^{1}$ and $R^{2}$ is H and the other radical of $R^{1}$ and $R^{2}$ is not H, or in the case that one of the radicals $R^{1}$ and $R^{2}$ denotes aryl', the other radical of $R^{1}$ and $R^{2}$ denotes H or methyl, ethyl, n-propyl, 2-propyl, n-butyl, tert.-butyl or n-hexyl, $R^{3}$ and $R^{4}$ denote H, methyl or aryl¹, wherein the aryl¹ substituents $R^{29}$, $R^{30}$ and $R^{31}$ independently of one another are H, methyl or O-methyl, wherein at least one of the radicals $R^{3}$ and $R^{4}$ is H, or one of the radicals $R^{1}$ and $R^{2}$ together with one of the radicals $R^{3}$ and $R^{4}$ forms W, where W denotes α'-CH=CH—$CH_2$-β', α'-CH=CH—$CH_2$—$CH_2$-β', α'-O—$(CH_2)_m$-β', where m=2, 3, 4 or 5

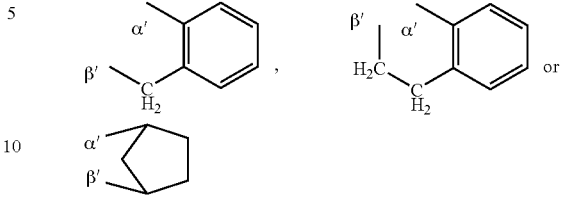

the end of W identified by α' is joined to the atom of the compound of the general structure (I A), (I B) or (II) identified by α, and the end of W identified by β' is joined to the atom of the compound of the general structure (I A), (I B) or (II) identified by β, the other radical of $R^{1}$ and $R^{2}$ and the other radical of $R^{3}$ and $R^{4}$ in each case denotes H;

$R^{5}$ denotes methyl, ethyl, n-propyl, 2-propyl, n-butyl, isobutyl, sec.-butyl, tert.-butyl, —$(CH_2)_4$—OH, cyclopropyl, where cyclopropyl is unsubstituted or singly substituted by C(=O)OH, C(=O)O-methyl or C(=O)O-ethyl, or denotes cyclopentyl, cyclohexyl, aryl¹ or —$(CH_2)_k$-aryl¹ where the aryl¹ substituents $R^{29}$, $R^{30}$ and $R^{31}$ independently of one another denote H, OH, —O-methyl, O—$C_6H_5$, $CH_3$, $CF_3$ or C(=O)OH and k=1 or 2, or denotes heterocyclyl or C(=O)$R^{11}$;

$R^{6}$ denotes H, —CN, bromine, —C(=O)$R^{17}$ or —N=N-phenyl;

$R^{7}$ denotes H, aryl¹ where $R^{29}$, $R^{30}$ and $R^{31}$ are H, OH, S(O)$_q$$R^{19}$, where q=0 or 2, or denotes methyl, ethyl, n-propyl, 2-propyl, n-butyl, isobutyl, sec.-butyl or tert.-butyl, $R^{8}$ denotes H, aryl¹ where the aryl¹ substituents $R^{29}$, $R^{30}$ and $R^{31}$ independently of one another are H, methyl or chlorine, or denotes aryl³ where $R^{29}$, $R^{30}$ and $R^{31}$ are H, or the radicals $R^{7}$ and $R^{8}$ together form Y, where Y denotes γ'-$CR^{21}$=$CR^{22}$—$CR^{23}$=$CR^{24}$-δ' and the end of Y identified by γ' is joined to the atom of the general structure (II) identified by γ, and the end of Y identified by δ' is joined to the atom of the general structure (II) identified by δ;

$R^{9}$ denotes methyl, ethyl, n-propyl, 2-propyl, n-butyl, isobutyl, sec.-butyl, tert.-butyl, n-amyl, isoamyl, sec.-amyl, n-hexyl, isohexyl, sec.-hexyl, cyclopropyl, cyclopentyl or cyclohexyl or denotes —$[(CH_2)_r$—O$]_s$—H where r=1, 2 or 3 and s=1 or 2;

$R^{10}$ denotes aryl¹;

$R^{11}$ denotes aryl¹ where $R^{29}$, $R^{30}$ and $R^{31}$ denote H or OR²⁵;

$R^{17}$ denotes $OR^{26}$;

$R^{19}$ denotes methyl or aryl¹, where one of the aryl¹ substituents $R^{29}$, $R^{30}$ and $R^{31}$ is H or —$NO_2$, and the two other aryl¹ substituents of $R^{29}$, $R^{30}$ and $R^{31}$ are H;

$R^{21}$ and $R^{23}$ denote H;

$R^{22}$ denotes H, fluorine or OR²⁸;

$R^{24}$ denotes H or chlorine;

$R^{25}$ denotes H, methyl or ethyl, where $R^{25}$ does not denote H if at the same time $R^{1}$ denotes aryl and $R^{2}$ denotes alkyl;

$R^{26}$ denotes H, methyl or ethyl;

$R^{28}$ denotes methyl or ethyl; and

Heterocyclyl denotes furan-2-yl, furan-3-yl, thien-2-yl, thien-3-yl, pyridin-2-yl, pyridin-3-yl or pyridin-4-yl, where furanyl, thienyl and pyridinyl are in each case unsubstituted or singly substituted or multiply identically or differently substituted by —$NO_2$, —$CH_3$ or C(=O)OH.

Most particularly preferred compounds according to the invention of the general structure (I A), (I B) or (II) are those in which $R^1$ and $R^1$ independently of one another denote H, O—CH$_2$—CH$_2$—OH, O-cyclohexyl, S-phenyl, methyl, phenyl, 3-fluorophenyl, 3-bromophenyl, 4-bromophenyl, 4-chlorophenyl, 4-fluorophenyl, 3-methylphenyl, 4-hydroxyphenyl, 4-methoxyphenyl, 2,4-dimethylphenyl, 3,4-dimethoxyphenyl, 2,3,4-trimethoxyphenyl, 2-naphthyl or —CH$_2$-phenyl, $R^3$ and $R^4$ denote H, methyl or 4-methoxyphenyl, where at least one of the radicals $R^3$ and $R^4$ is H, or one of the radicals $R^1$ and $R^2$ together with one of the radicals $R^3$ and $R^4$ form W, where W denotes α'-CH=CH—CH$_2$-β', α'-CH=CH—CH$_2$—CH$_2$-β', α'-O—(CH$_2$)$_m$-β' where m=2, 3, 4 or 5,

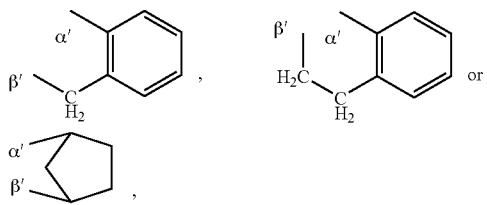

the end of W identified by α' is joined to the atom of the compound of the general structure (I A), (I B) or (II) identified by α, and the end of W identified by β' is joined to the atom of the compound of the general structure (I A), (I B) or (II) identified by β, and the other radical of $R^1$ and $R^2$ and the other radical of $R^3$ and $R^4$ in each case denote H;

$R^5$ denotes n-propyl, n-butyl, tert.-butyl, —(CH$_2$)$_4$—OH, cyclopropyl, cycloprop-2-yl-1-carboxylic acid ethyl ether, cyclohexyl, 4-trifluorophenyl, 4-phenoxyphenyl, 2-hydroxy-3-methoxyphenyl, 4-hydroxy-3-methoxyphenyl, 3-carboxy-2-hydroxy-phenyl, —(CH$_2$)$_2$-phenyl, 5-carboxyfuran-2-yl, 5-methylfuran-2-yl, 5-nitrofuran-2-yl, 5-nitro-thien-2-yl, pyridin-2-yl, pyridin-3-yl, C(=O)phenyl, C(=O)OH or C(=O)Oethyl, where $R^5$ does not denote C(=O)OH if at the same time $R^1$ denotes aryl and $R^2$ denotes alkyl;

$R^6$ denotes H, —CN, bromo, —C(=O)OH, —C(=O)Oethyl or —N=N-phenyl;

$R^7$ denotes H, phenyl, OH, —S-methyl, —SO$_2$-(4-nitrophenyl) or tert.-butyl;

$R^8$ denotes 4-chlorophenyl, 4-methylphenyl or 2-naphthyl; or the radicals $R^7$ and $R^8$ together form Y, where Y denotes γ'-CR$^{21}$=CH—CH=CH-δ' and the end of Y identified by γ' is joined to the atom of the general structure (II) identified by γ, and the end of Y identified by δ' is joined to the atom of the general structure (II) identified by δ; and $R^{21}$ denotes fluorine, methoxy or ethoxy.

Exemplary and advantageous compounds of the present invention are selected from the group that comprises 3-bromo-5-(5-nitrofuran-2-yl)-7-m-tolyltetrahydropyrazolo[1,5-a]pyrimidine 3-bromo-7-(4-fluorophenyl)-7-methyl-5-(5-nitrofuran-2-yl)-tetrahydropyrazolo[1,5-a]pyrimidine 3-bromo-7-naphthalin-2-yl-5-(5-nitrofuran-2-yl)-tetrahydropyrazolo[1,5-a]pyrimidine 2-(3-bromo-7-m-tolyltetrahydropyrazolo[1,5-a]pyrimidin-5-yl)-cyclopropanecarboxylic acid ethyl ester 2-[3-bromo-7-(4-bromophenyl)-tetrahydropyrazolo[1,5-a]pyrimidin-5-yl]-cyclopropanecarboxylic acid ethyl ester 2-(3-bromo-7-naphthalin-2-yl-tetrahydropyrazolo[1,5-a]pyrimidin-5-yl)-cyclopropanecarboxylic acid ethyl ester 3-bromo-7-(4-fluorophenyl)-7-methyl-5-(5-methylfuran-2-yl)-tetrahydropyrazolo[1,5-a]pyrimidine 3-bromo-7-(3,4-dimethoxyphenyl)-tetrahydropyrazolo[1,5-a]pyrimidine-5-carboxylic acid ethyl ester 3-bromo-7-(4-methoxyphenyl)-tetrahydropyrazolo[1,5-a]pyrimidine-5-carboxylic acid ethyl ester 3-bromo-7-(4-methoxyphenyl)-tetrahydropyrazolo[1,5-a]pyrimidine-5-carboxylic acid 3-bromo-7-(2,4-dimethylphenyl)-5-(5-nitrofuran-2-yl)-tetrahydropyrazolo[1,5-a]pyrimidine 3-bromo-7-(4-methoxyphenyl)-5-(5-nitrofuran-2-yl)-tetrahydropyrazolo[1,5-a]pyrimidine 5,5a,6,8a-tetrahydro-3H-1,4,8b-triaza-as-indacene-3,5-dicarboxylic acid diethyl ester; 5,5a,6,8a-tetrahydro-4H-1,4,8b-triaza-as-indacene-3,5-dicarboxylic acid diethyl ester 2-hydroxy-3-phenylazo-5,5a,6,8a-tetrahydro-3H-1,4,8b-triaza-as-indacene-5-carboxylic acid ethyl ester; 2-hydroxy-3-phenylazo-5,5a,6,8a-tetrahydro-4H-1,4,8b-triaza-as-indacene-5-carboxylic acid ethyl ester 2-tert.-butyl-5,5a,6,8a-tetrahydro-3H-1,4,8b-triaza-as-indacene-5-carboxylic acid ethyl ester; 2-tert.-butyl-5,5a,6,8a-tetrahydro-3H-1,4,8b-triaza-as-indacene-5-carboxylic acid ethyl ester 3-bromo-2-phenyl-5,5a,6,8a-tetrahydro-3H-1,4,8b-triaza-as-indacene-5-carboxylic acid ethyl ester; 3-bromo-2-phenyl-5,5a,6,8a-tetrahydro-4H-1,4,8b-triaza-as-indacene-5-carboxylic acid ethyl ester 7-(2,3,4-trimethoxyphenyl)-tetrahydropyrazolo[1,5-a]pyrimidine-3,5-dicarboxylic acid diethyl ester 3-cyano-2-methylsulfanyl-7-(2,3,4-trimethoxyphenyl)-tetrahydropyrazolo[1,5-a]pyrimidine-5-carboxylic acid ethyl ester 2-hydroxy-7-(4-hydroxyphenyl)-6-methyl-3-phenylazotetrahydropyrazolo[1,5-a]pyrimidine-5-carboxylic acid ethyl ester 3-bromo-7-(4-hydroxyphenyl)-6-methyl-2-phenyltetrahydropyrazolo[1,5-a]pyrimidine-5-carboxylic acid ethyl ester 5,5a,6,10b-tetrahydro-3H-1,4,10c-triazacyclopenta[c]fluorene-3,5-dicarboxylic acid diethyl ester; 5,5a,6,10b-tetrahydro-4H-1,4,10c-triazacyclopenta[c]fluorene-3,5-dicarboxylic acid diethyl ester 2-hydroxy-3-phenylazo-5,5a,6,10b-tetrahydro-3H-1,4,10c-triazacyclopenta[c]fluorene-5-carboxylic acid ethyl ester; 2-hydroxy-3-phenylazo-5,5a,6,10b-tetrahydro-4H-1,4,10c-triazacyclopenta[c]fluorene-5-carboxylic acid ethyl ester 7-phenylsulfanyltetrahydropyrazolo[1,5-a]pyrimidine-3,5-dicarboxylic acid diethyl ester 3-cyano-2-methylsulfanyl-7-phenylsulfanyltetrahydropyrazolo[1,5-a]pyrimidine-5-carboxylic acid ethyl ester 3-cyano-2-methylsulfanyl-7-(2,3,4-trimethoxyphenyl)-tetrahydropyrazolo[1,5-a]pyrimidine-5-carboxylic acid 7-phenylsulfanyltetrahydropyrazolo[1,5-a]pyrimidine-3,5-dicarboxylic acid-3-ethyl ester 3-cyano-7-(2,4-dimethylphenyl)-2-methylsulfanyl-tetrahydropyrazolo[1,5-a]pyrimidine-5-carboxylic acid ethyl ester 3-cyano-7-(2,4-dimethylphenyl)-tetrahydropyrazolo-[1,5-a]pyrimidine-5-carboxylic acid ethyl ester 7-(2,4-dimethylphenyl)-tetrahydropyrazolo-[1,5-a]pyrimidine-3,5-dicarboxylic acid-3-ethyl ester 3-bromo-7-(2,4-dimethylphenyl)-2-phenyltetrahydropyrazolo-[1,5-a]pyrimidine-5-carboxylic acid
3-cyano-7-(2,4-dimethylphenyl)-2-methylsulfanyltetrahydropyrazolo[1,5-a]pyrimidine-5-carboxylic acid
3-cyano-7-(2,4-dimethylphenyl)-tetrahydropyrazolo-[1,5-a]pyrimidine-5-carboxylic acid
3-cyano-7-(3,4-dimethoxyphenyl)-2-methylsulfanyltetrahydropyrazolo[1,5-a]pyrimidine-5-carboxylic acid
7-(2,4-dimethylphenyl)-5-(5-nitrofuran-2-yl)-tetrahydropyrazolo[1,5-a]pyrimidine-3-carboxylic acid ethyl ester
7-(2,4-dimethylphenyl)-5-(5-nitrofuran-2-yl)-3-phenylazotetrahydropyrazolo[1,5-a]pyrimidin-2-ol
3-bromo-7-(2,4-dimethylphenyl)-5-(5-nitrofuran-2-yl)-2-phenylazotetrahydropyrazolo[1,5-a]pyrimidine
7-(2,4-dimethylphenyl)-2-methylsulfanyl-5-(5-nitrofuran-2-yl)-tetrahydropyrazolo[1,5-a]pyrimidine-3-carbonitrile
7-(2,4-dimethylphenyl)-5-(5-nitrofuran-2-yl)-tetrahydropyrazolo[1,5-a]pyrimidine-3-carbonitrile
3-bromo-7-(3,4-dimethoxyphenyl)-5-(5-nitrofuran-2-yl)-2-phenyltetrahydropyrazolo[1,5-a]pyrimidine
7-(4-methoxyphenyl)-2-methylsulfanyl-5-(5-nitrofuran-2-yl)-tetrahydropyrazolo[1,5-a]pyrimidine-3-carbonitrile
7-(2,4-dimethylphenyl)-5-(2-ethoxycarbonylcyclopropyl)-tetrahydropyrazolo[1,5-a]pyrimidine-3-carboxylic acid ethyl ester
2-[7-(2,4-dimethylphenyl)-2-hydroxy-3-phenylazotetrahydropyrazolo[1,5-a]pyrimidin-5-yl]-cyclopropanecarboxylic acid ethyl ester
2-[2-tert.-butyl-7-(2,4-dimethylphenyl)tetrahydropyrazolo[1,5-a]pyrimidin-5-yl]cyclopropanecarboxylic acid ethyl ester
2-[3-bromo-7-(2,4-dimethylphenyl)-2-phenyltetrahydropyrazolo[1,5-a]pyrimidin-5-yl]cyclopropanecarboxylic acid ethyl ester
2-[3-cyano-7-(2,4-dimethylphenyl)-2-methylsulfanyltetrahydropyrazolo[1,5-a]pyrimidin-5-yl]cyclopropanecarboxylic acid ethyl ester
5-(2-ethoxycarbonylcyclopropyl)-7-(3-fluorophenyl)-tetrahydropyrazolo[1,5-a]pyrimidine-3-carboxylic acid ethyl ester
2-[3-bromo-7-(3-bromophenyl)-2-phenyltetrahydropyrazolo[1,5-a]pyrimidin-5-yl]cyclopropanecarboxylic acid ethyl ester
2-[7-(3-bromophenyl)-3-cyano-2-methylsulfanyltetrahydropyrazolo[1,5-a]pyrimidin-5-yl]cyclopropanecarboxylic acid ethyl ester
7-(2,4-dimethylphenyl)-5-(5-nitrothiophen-2-yl)-3-phenylazotetrahydropyrazolo[1,5-a]pyrimidin-2-ol
7-(2,4-dimethylphenyl)-2-methylsulfanyl-5-(5-nitrothiophen-2-yl)-tetrahydropyrazolo[1,5-a]pyrimidine-3-carbonitrile
7-(2,4-dimethylphenyl)-5-(5-nitrothiophen-2-yl)-tetrahydropyrazolo[1,5-a]pyrimidine-3-carbonitrile
7-(3,4-dimethoxyphenyl)-5-(5-nitrothiophen-2-yl)-tetrahydropyrazolo[1,5-a]pyrimidine-3-carboxylic acid ethyl ester
7-(3,4-dimethoxyphenyl)-5-(5-nitrothiophen-2-yl)-3-phenylazotetrahydropyrazolo[1,5-a]pyrimidin-2-ol
3-bromo-7-(3,4-dimethoxyphenyl)-5-(5-nitrothiophen-2-yl)-2-phenyltetrahydropyrazolo[1,5-a]pyrimidine
7-(3,4-dimethoxyphenyl)-2-methylsulfanyl-5-(5-nitrothiophen-2-yl)-tetrahydropyrazolo[1,5-a]pyrimidine-3-carbonitrile
7-(3,4-dimethoxyphenyl)-5-(5-nitrothiophen-2-yl)-tetrahydropyrazolo[1,5-a]pyrimidine-3-carbonitrile
7-(4-methoxyphenyl)-5-(5-nitrothiophen-2-yl)-tetrahydropyrazolo[1,5-a]pyrimidine-3-carboxylic acid ethyl ester
5-[3-bromo-7-(4-methoxyphenyl)-2-phenyltetrahydropyrazolo[1,5-a]pyrimidin-5-yl]-furan-2-carboxylic acid
5-benzoyl-7-(2,4-dimethylphenyl)-tetrahydropyrazolo-[1,5-a]pyrimidine-3-carboxylic acid ethyl ester
5-benzoyl-7-(2,4-dimethylphenyl)-2-methylsulfanyltetrahydropyrazolo[1,5-a]pyrimidine-3-carbonitrile
5-benzoyl-7-(2,4-dimethylphenyl)-tetrahydropyrazolo-[1,5-a]pyrimidine-3-carbonitrile
5-benzoyl-7-(3,4-dimethoxyphenyl)-tetrahydropyrazolo[1,5-a]pyrimidine-3-carboxylic acid ethyl ester
[3-bromo-7-(3,4-dimethoxyphenyl)-2-phenyltetrahydropyrazolo[1,5-a]pyrimidin-5-yl]-phenylmethanone
5-benzoyl-7-(3,4-dimethoxyphenyl)-2-methylsulfanyltetrahydropyrazolo[1,5-a]pyrimidine-3-carbonitrile
5-benzoyl-7-(3,4-dimethoxyphenyl)tetrahydropyrazolo[1,5-a]pyrimidine-3-carbonitrile
5-benzoyl-7-(4-methoxyphenyl)-tetrahydropyrazolo-[1,5-a]pyrimidine-3-carboxylic acid ethyl ester
5-benzoyl-7-(4-methoxyphenyl)-2-methylsulfanyltetrahydropyrazolo[1,5-a]pyrimidine-3-carbonitrile
5-benzoyl-7-(4-methoxyphenyl)tetrahydropyrazolo-[1,5-a]pyrimidine-3-carbonitrile
5-benzoyl-7-(3-fluorophenyl)-tetrahydropyrazolo-[1,5-a]pyrimidine-3-carboxylic acid ethyl ester
[3-bromo-7-(3-fluorophenyl)-2-phenyltetrahydropyrazolo[1,5-a]pyrimidin-5-yl]-phenylmethanone
[3-bromo-7-(3-bromophenyl)-2-phenyltetrahydropyrazolo[1,5-a]pyrimidin-5-yl]-phenylmethanone
7-(2,4-dimethylphenyl)-5-(4-phenoxyphenyltetrahydropyrazolo[1,5-a]pyrimidine-3-carboxylic acid ethyl ester
3-bromo-7-(2,4-dimethylphenyl)-5-(4-phenoxyphenyl)-2-phenyltetrahydropyrazolo[1,5-a]pyrimidine
7-(2,4-dimethylphenyl)-2-methylsulfanyl-5-(4-phenoxyphenyl)-tetrahydropyrazolo[1,5-a]pyrimidine-3-carbonitrile
7-(2,4-dimethylphenyl)-5-(4-phenoxyphenyl)-tetrahydropyrazolo[1,5-a]pyrimidine-3-carbonitrile
7-(3,4-dimethoxyphenyl)-5-(4-phenoxyphenyl)-tetrahydropyrazolo[1,5-a]pyrimidine-3-carboxylic acid ethyl ester
7-(3,4-dimethoxyphenyl)-2-methylsulfanyl-5-(4-phenoxyphenyl)-tetrahydropyrazolo[1,5-a]pyrimidine-3-carbonitrile
3-[3-cyano-7-(4-hydroxyphenyl)-6-methyltetrahydropyrazolo[1,5-a]pyrimidin-5-yl]-2-hydroxybenzoic acid
3-(3-cyano-5,5a,6,10b-tetrahydro-3H-1,4,10c-triazacyclopenta[c]fluoren-5-yl)-2-hydroxybenzoic acid; 3-(3-cyano-5,5a,6,10b-tetrahydro-4H-1,4,10c-triazacyclopenta[c]fluoren-5-yl)-2-hydroxybenzoic acid
3-(3-cyano-7-phenylsulfanyltetrahydropyrazolo[1,5-a]pyrimidin-5-yl]-2-hydroxybenzoic acid
3-[2-tert.-butyl-7-(4-chlorophenyl)-7-methyltetrahydropyrazolo[1,5-a]pyrimidin-5-yl]-2-hydroxybenzoic acid
5-(4-hydroxy-3-methoxyphenyl)-7-(4-hydroxyphenyl)-6-methyltetrahydropyrazolo[1,5-a]pyrimidine-3-carboxylic acid ethyl ester
5-(4-hydroxy-3-methoxyphenyl)-7-(4-hydroxyphenyl)-6-methyltetrahydropyrazolo[1,5-a]pyrimidine-3-carbonitrile
5-(4-hydroxy-3-methoxyphenyl)-5,5a,6,10b-tetrahydro-3H-1,4,10c-triazacyclopenta[c]fluorene-3-carboxylic acid ethyl ester; 5-(4-hydroxy-3-methoxyphenyl)-5,5a,6,10b-tetrahydro-4H-1,4,10c-triazacyclopenta[c]fluorene-3-carboxylic acid ethyl ester
4-(2-tert.-butyl-5,5a,6,10b-tetrahydro-3H-1,4,10c-triazacyclopenta[c]fluoren-5-yl)-2-methoxyphenol; 4-(2-tert.-butyl-5,5a,6,10b-tetrahydro-4H-1,4,10c-triazacyclopenta[c]fluoren-5-yl)-2-methoxyphenol 5-(4-hydroxy-3-methoxyphenyl)-2-methylsulfanyl-5,5a,6,10b-tetrahydro-3H-1,4,10c-triazacyclopenta[c]fluorene-3-carbonitrile; 5-(4-hydroxy-3-methoxyphenyl)-2-methylsulfanyl-5,5a,6,10b-tetrahydro-3H-1,4,10c-triazacyclopenta[c]fluorene-3-carbonitrile 5-(4-hydroxy-3-methoxyphenyl)-7-phenylsulfanyl-tetrahydropyrazolo[1,5-a]pyrimidine-3-carboxylic acid ethyl ester 4-(2-tert.-butyl-7-phenylsulfanyltetrahydropyrazolo[1,5-a]pyrimidin-5-yl)-2-methoxyphenol 4-(3-bromo-2-phenyl-7-phenylsulfanyltetrahydropyrazolo[1,5-a]pyrimidin-5-yl)-2-methoxyphenol 5-(2-hydroxy-3-methoxyphenyl)-7-phenylsulfanyltetrahydropyrazolo[1,5-a]pyrimidine-3-carboxylic acid ethyl ester 7-(4-chlorophenyl)-5-(2-hydroxy-3-methoxyphenyl)-7-methyltetrahydropyrazolo[1,5-a]pyrimidine-3-carboxylic acid ethyl ester 5-(4-hydroxybutyl)-5,5a,6,10b-tetrahydro-3H-1,4,10c-triazacyclopenta[c]fluorene-3-carbonitrile; 5-(4-hydroxybutyl)-5,5a,6,10b-tetrahydro-4H-1,4,10c-triazacyclopenta[c]fluorene-3-carbonitrile 5-(4-hydroxybutyl)-2-methylsulfanyl-7-phenylsulfanyltetrahydropyrazolo[1,5-a]pyrimidine-3-carbonitrile 5-(4-hydroxybutyl)-7-phenylsulfanyltetrahydropyrazolo[1,5-a]pyrimidine-3-carbonitrile 7-(4-chlorophenyl)-5-(4-hydroxybutyl)-7-methyltetrahydropyrazolo[1,5-a]pyrimidine-3-carbonitrile 5-butyl-2-methylsulfanyl-5,5a,6,10b-tetrahydro-3H-1,4,10c-triazacyclopenta[c]fluorene-3-carbonitrile;

5-butyl-2-methylsulfanyl-5,5a,6,10b-tetrahydro-4H-1,4,10c-triazacyclopenta[c]fluorene-3-carbonitrile 5-butyl-2-methylsulfanyl-7-phenylsulfanyltetrahydropyrazolo[1,5-a]pyrimidine-3-carbonitrile 5-butyl-7-phenylsulfanyltetrahydropyrazolo[1,5-a]pyrimidine-3-carbonitrile 5-butyl-7-(4-chlorophenyl)-7-methylsulfanyltetrahydropyrazolo[1,5-a]pyrimidine-3-carbonitrile 5-cyclopropyl-7-(2,4-dimethylphenyl)-3-phenylazotetrahydropyrazolo[1,5-a]pyrimidin-2-ol 2-tert.-butyl-5-cyclopropyl-7-(2,4-dimethylphenyl)-tetrahydropyrazolo[1,5-a]pyrimidine 5-cyclopropyl-7-(2,4-dimethylphenyl)-2-methyl-sulfanyltetrahydro-pyrazolo[1,5-a]pyrimidine-3-carbonitrile 2-tert.-butyl-5-cyclopropyl-7-(3,4-dimethoxyphenyl)-tetrahydropyrazolo[1,5-a]pyrimidine 3-bromo-5-cyclopropyl-7-(3,4-dimethoxyphenyl)-2-phenyltetrahydropyrazolo[1,5-a]pyrimidine 5-cyclopropyl-7-(4-methoxyphenol)-tetrahydropyrazolo[1,5-a]pyrimidine-3-carboxylic acid ethyl ester 5-cyclopropyl-3,5,5a,6,7,11b-hexahydro-1,4,11c-triazacyclopenta[c]phenanthrene-3-carbonitrile 7-(2,4-dimethylphenyl)-5-pyridin-2-yl-tetrahydropyrazolo[1,5-a]pyrimidine-3-carboxylic acid ethyl ester 7-(2,4-dimethylphenyl)-3-phenylazo-5-pyridin-2-yl-tetrahydropyrazolo[1,5-a]pyrimidin-2-ol 3-bromo-7-(2,4-dimethylphenyl)-2-phenyl-5-pyridin-2-yl-tetrahydropyrazolo[1,5-a]pyrimidine 7-(2,4-dimethylphenyl)-2-methylsulfanyl-5-pyridin-2-yl-tetrahydropyrazolo[1,5-a]pyrimidine-3-carbonitrile 7-(3,4-dimethoxyphenyl)-2-methylsulfanyl-5-phenethyltetrahydropyrazolo[1,5-a]pyrimidine-3-carbonitrile 7-(3,4-dimethoxyphenyl)-5-phenethyl-tetrahydropyrazolo[1,5-a]pyrimidine-3-carbonitrile 5-cyclopropyl-7-(2-hydroxyethoxy)-tetrahydropyrazolo[1,5-a]pyrimidine-3-carboxylic acid ethyl ester 2-(2-tert.-butyl-5-cyclopropyltetrahydropyrazolo-[1,5-a]pyrimidin-7-yloxy)-ethanol 5-cyclopropyl-3,5,5a,6,7,8a-hexahydro-8-oxa-1,4,8b-triaza-as-indacene-3-carboxylic acid ethyl ester; 5-cyclopropyl-4,5,5a,6,7,8a-hexahydro-8-oxa-1,4,8b-triaza-as-indacene-3-carboxylic acid ethyl ester 5-cyclopropyl-3-phenylazo-3,5,5a,6,7,8a-hexahydro-8-oxa-1,4,8b-triaza-as-indacen-2-ol; 5-cyclopropyl-3-phenylazo-4,5,5a,6,7,8a-hexahydro-8-oxa-1,4,8b-triaza-as-indacen-2-ol 7-cyclohexyloxy-5-cyclopropyltetrahydropyrazolo-[1,5-a]pyrimidin-3-carboxylic acid ethyl ester 7-cyclohexyloxy-5-cyclopropyl-2-methylsulfanyltetrahydropyrazolo[1,5-a]pyrimidin-3-carbonitrile 7-(4-chlorophenyl)-5-cyclohexyltetrahydropyrazolo-[1,5-a]pyrimidin-3-carbonitrile 5-cyclohexyl-7-(2-hydroxyethoxy)-tetrahydropyrazolo[1,5-a]pyrimidine-3-carboxylic acid ethyl ester 5-cyclohexyl-3,5,5a,6,7,8a-hexahydro-8-oxa-1,4,8b-triaza-as-indacene-3-carboxylic acid ethyl ester; 5-cyclohexyl-4,5,5a,6,7,8a-hexahydro-8-oxa-1,4,8b-triaza-as-indacene-3-carboxylic acid ethyl ester 5-cyclohexyl-7-cyclohexyloxytetrahydropyrazolo[1,5-a]pyrimidine-3-carboxylic acid ethyl ester 7-(2,4-dimethylphenyl)-3-phenylazo-5-propyl-tetrahydropyrazolo[1,5-a]pyrimidin-2-ol 7-(2,4-dimethylphenyl)-2-methylsulfanyl-5-propyl-tetrahydropyrazolo[1,5-a]pyrimidine-3-carbonitrile 5-tert.-butyl-7-(2,4-dimethylphenyl)-tetrahydropyrazolo[1,5-a]pyrimidine-3-carboxylic acid ethyl ester 2,5-di-tert.-butyl-7-(3,4-dimethoxyphenyl)-tetrahydropyrazolo[1,5-a]pyrimidine 3-bromo-5-tert.-butyl-7-(3,4-dimethoxyphenyl)-2-phenyltetrahydropyrazolo[1,5-a]pyrimidine 2-[3-cyano-6,7-bis-(4-methoxyphenyl)-tetrahydropyrazolo[1,5-a]pyrimidin-5-yl]-cyclopropanecarboxylic acid ethyl ester 3-cyano-6,7-bis-(4-methoxyphenyl)-tetrahydropyrazolo[1,5-a]pyrimidine-5-carboxylic acid 4-[3-bromo-6-methyl-2-phenyl-5-(4-trifluoro-methylphenyl)-tetrahydropyrazolo[1,5-a]pyrimidin-7-yl]-phenol 7-(4-hydroxyphenyl)-6-methyl-2-methylsulfanyl-5-(4-trifluoro-methylphenyl)-tetrahydropyrazolo[1,5-a]pyrimidine-3-carbonitrile 7-(4-hydroxyphenyl)-6-methyl-5-(4-trifluoromethylphenyl)-tetrahydropyrazolo[1,5-a]pyrimidine-3-carbonitrile 2-(4-nitrophenylsulfonyl)-5-phenylsulfanyl-7-pyridin-2-yl-6,7-dihydro-5H-thiazolo[3,2-a]pyrimidine 3-(4-chlorophenyl)-5-phenylsulfanyl-7-pyridin-2-yl-6,7-dihydro-5H-thiazolo[3,2-a]pyrimidine 5-phenylsulfanyl-7-pyridin-2-yl-3-p-tolyl-6,7-dihydro-5H-thiazolo[3,2-a]pyrimidine 7-methoxy-4-phenylsulfanyl-2-pyridin-2-yl-3,4-dihydro-2H-9-thia-1,4a-diazafluorene 7-ethoxy-4-phenylsulfanyl-2-pyridin-2-yl-3,4-dihydro-2H-9-thia-1,4a-diazafluorene 7-fluoro-4-phenylsulfanyl-2-pyridin-2-yl-3,4-dihydro-2H-9-thia-1,4a-diazafluorene 3-naphthalin-2-yl-5-phenylsulfanyl-7-pyridin-2-yl-6,7-dihydro-5H-thiazolo[3,2-a]pyrimidine 7-phenyl-3-phenylazo-5-pyridin-2-yl-3,5,6,7-tetrahydropyrazolo[1,5-a]pyrimidin-2-ol 7-phenylsulfanyl-5-pyridin-2-yl-3,5,6,7-tetrahydropyrazolo[1,5-a]pyrimidine-3-carboxylic acid ethyl ester 3-phenylazo-7-phenylsulfanyl-5-pyridin-2-yl-3,5,6,7-tetrahydropyrazolo[1,5-a]pyrimidin-2-ol 3-bromo-7-phenylsulfanyl-5-pyridin-2-yl-3,5,6,7-tetrahy-dropyrazolo[1,5-a]pyrimidine 7-phenylsulfanyl-5-pyridin-2-yl-3,5,6,7-tetrahydropyrazolo[1,5-a]pyrimidine-3-carbonitrile 7-(3,4-dimethoxyphenyl)-2-methylsulfanyl-5-pyridin-2-yl-tetrahydropyrazolo[1,5-a]pyrimidine-3-carbonitrile 3-bromo-7-(3,4-dimethoxyphenyl)-2-phenyl-5-pyridin-2-yl-tetrahydropyrazolo[1,5-a]pyrimidine 3-bromo-7-(3,4-dimethoxyphenyl)-2-phenyl-tetrahydropyrazolo[1,5-a]pyrimidine-5-carboxylic acid ethyl ester 3-bromo-7-(3,4-dimethoxyphenyl)-5-(5-nitrofuran-2-yl)-2-phenyl-tetrahydropyrazolo[1,5-a]pyrimidine 3-cyano-7-(3,4-dimethoxyphenyl)-2-methylsulfanyl-tetrahydropyrazolo[1,5-a]pyrimidine-5-carboxylic acid ethyl ester 3-cyano-7-(3,4-dimethoxyphenyl)-tetrahydropyrazolo-[1,5-a]pyrimidine-5-carboxylic acid ethyl ester 3-bromo-7-(3,4-dimethoxyphenyl)-2-phenyl-5-pyridin-2-yl-4,5,6,7-tetrahydropyrazolo[1,5-a]pyrimidine 7-(3,4-dimethoxyphenyl)-5-pyridin-2-yl-4,5,6,7-tetrahydropyrazolo[1,5-a]pyrimidine-3-carbonitrile 7-(3,4-dimethoxyphenyl)-2-methylsulfanyl-5-(5-nitrofuran-2-yl)-tetrahydropyrazolo[1,5-a]-pyrimidine-3-carbonitrile 7-(3,4-dimethoxyphenyl)-5-pyridin-2-yl-4,5,6,7-tetrahydropyrazolo[1,5-a]pyrimidine-3-carboxylic acid ethyl ester as well as their pharmaceutically acceptable salts.

The present invention also relates to processes for the production of the compounds of the structure (I A), (I B) and (II) according to the invention.

Accordingly, the compounds of the general structure (I A) and (I B) as well as their pharmaceutically acceptable salts

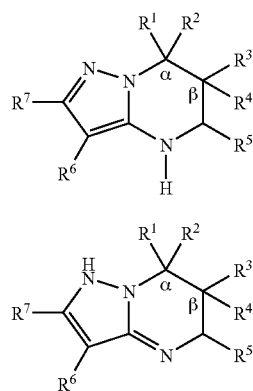

wherein $R^1$, $R^2$, $R^3$, $R^4$, $R^5$, $R^6$ and $R^7$ are as defined above, can be prepared by reacting a pyrazolamine of the general structure (IIIA) and/or (IIIB)

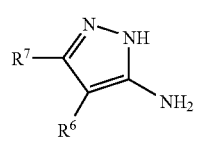

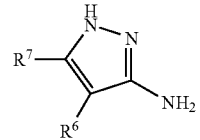

wherein $R^6$ and $R^7$ are as defined above, with an aldehyde of the general structure (IV)

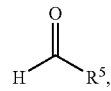

wherein $R^5$ is as defined above, and with an olefin of the general structure (V)

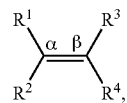

wherein $R^1$, $R^2$, $R^3$ and $R^4$ are as defined above, with the proviso that if one of the radicals $R^1$ and $R^2$ together with one of the radicals $R^3$ and $R^4$ forms W, the end of W identified by α' is joined to the α-carbon atom of the olefin of the general structure (V), and the end of W identified by β' is joined to the β-carbon atom of the olefin of the general structure (V), in the presence of an acid.

Accordingly the compounds of the general structure (II) according to the invention as well as their pharmaceutically acceptable salts

II wherein $R^1$, $R^2$, $R^3$, $R^4$, $R^5$, $R^7$ and $R^8$ are as defined above, can be obtained by reacting a thiazolamine of the general structure (VI)

VI wherein $R^7$ and $R^8$ are as defined above, with the proviso that if $R^7$ and $R^8$ form Y, the end of Y identified by γ' is coupled to the atom of the thiazolamine of the general structure (VI) identified by γ and the end of Y identified by δ' is coupled to the atom of the thiazolamine of the general structure (VI) identified by δ, with an aldehyde of the general structure (IV)

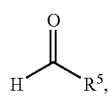

wherein $R^5$ is as defined above, and with an olefin of the general structure (V)

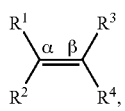

wherein $R^1$, $R^2$, $R^3$ and $R^4$ are as defined above, with the proviso that if one of the radicals $R^1$ and $R^2$ together with one of the radicals $R^3$ and $R^4$ form W, the end of W identified by α' is joined to the α-carbon atom of the olefin of the general structure (V) and the end of W identified by β' is joined to the β-carbon atom of the olefin of the general structure (V), in the presence of an acid.

The processes according to the invention are preferably carried out in a "one-pot" reaction, in which a heterocyclylamine of the general structure (II A), (II B) or (VI), an aldehyde of the general structure (IV) and an olefin of the general structure (V) are simultaneously reacted with one another.

The acid that is used is an inorganic or organic protonic or Lewis acid. Preferably the reaction is carried out in the presence of an organic acid, for example acetic acid, trifluoroacetic acid or methanesulfonic acid, especially trifluoroacetic acid.

The production process according to the invention may be carried out in any suitable solvent in which the reactants are sufficiently soluble. Preferably organic solvents are used, for example dichloromethane or in particular acetonitrile.

The processes according to the invention are conveniently carried out at a temperature of 0° to 100° C., in particular 15° to 40° C. The reaction time is preferably 15 minutes to 12 hours and may be adapted to the respective requirements.

All heterocyclylamines of the general structure (III) or (VI), the aldehydes of the general structure (IV) and the olefins of the general structure (V) that are used in the processes according to the invention are commercially available (from Acros, Geel; Avocado, Port of Heysham; Aldrich, Delsenhofen; Fluka, Seelze; Lancaster, Mülheim; Maybridge, Tintagel; Merck, Darmstadt; Sigma, Deisenhofen; TCI, Japan) or may be prepared according to processes generally known in the prior art.

The processes according to the invention may also be carried out in semi-automated or fully automated form as parallel synthesis of a group of compounds of the general structure (I A), (I B) and/or (II) according to the invention. Accordingly, substance libraries that contain at least one compound and preferably at least 48, in particular 96 and most particularly preferably 384 compounds of the general structure (I A), (I B) or (II) as defined above are also the subject of the present invention.

For the purposes of the present invention the expression "substance library" is understood to denote a group of compounds that are prepared according to the same process under identical or almost identical reaction conditions and by varying one reactant or several reactants. Such a substance library may contain the library items both as individual pure compounds as well as in the form of a mixture of these compounds. With the aid of this substance library a medical screening for example may be performed in an automated manner in one or several in vitro screening processes.

The compounds of the general structure (I A) and/or (I B) or (II) may be isolated both as the substance per se as well as in the form of a salt. The substances of the general structure (I A), (I B) or (II) are usually obtained by reaction according to the process outlined above followed by conventional working-up. The compounds that are thereby obtained may then be converted into the corresponding salt by for example adding an inorganic or organic acid, preferably hydrochloric acid, hydrobromic acid, sulfuric acid, phosphoric acid, methanesulfonic acid, p-toluenesulfonic acid, carbonic acid, formic acid, acetic acid, oxalic acid, succinic acid, tartaric acid, mandelic acid, fumaric acid, lactic acid, citric acid, glutamic acid or aspartic acid. The salts that are formed include, inter alia, hydrochlorides, hydrobromides, phosphates, carbonates, hydrogen carbonates, formates, acetates, oxalates, succinates, tartrates, fumarates, citrates and glutamates. In the case where the compounds of the general structure (I A), (I B) and/or (II) are acids, in particular carboxylic acids (for example if $R^5$= ($CO_2H$), the salt formation may be carried out by addition of a base, for example sodium hydroxide, $NaHCO_3$ or sodium carbonate; for the (carboxylic) acids it is particularly preferred to form the sodium salt. The particularly preferred hydrochloride formation may in particular also be carried out by adding trimethylsilyl chloride (TMSC) to the base (I A), (I B) or (II) dissolved in a suitable organic solvent. The formation of sodium salts may be carried out by for example titrating the compound (I A), (I B) or (II) dissolved in a suitable solvent, for example a water-methanol mixture, with sodium hydroxide solution.

Where the compounds of the general structure (I A), (I B) or (II) are obtained in the production process according to the invention as racemates or as mixtures of their various enantiomers and/or diastereomers, these mixtures may be separated according to processes that are well known in the prior art. Suitable methods include, inter alia, chromatographic separation processes, in particular liquid chromatography processes under normal or elevated pressure, preferably MPLC and HPLC processes, as well as fractional crystallisation processes. In this connection in particular individual enantiomers may be separated from one another for example by means of chiral phase HPLC or by means of crystallisation of diastereomer salts formed with chiral acids, for example (+)-tartaric acid, (−)-tartaric acid or (+)-10-camphorsulfonic acid or—where acids are involved—formed with chiral bases, for example brucine or (−)-ephedrine.

Moreover the present invention also provides a medicament that comprises at least one of the compounds according to the invention of the general structure (I a), (I B) or (II) as defined above and/or their pharmaceutically acceptable salts. In this connection the compounds according to the invention may be present in the medicament according to the invention as isomer-pure, in particular enantiomer-pure and/or diastereomer-pure compounds, but also as a racemic or non-racemic mixture. Preferably the medicament contains a pharmaceutically acceptable salt of the compounds according to the invention, in particular a hydrochloride or a sodium salt.

The present invention also provides for the use of at least one compound according to the invention of the general structure (I A), (I B) or (II), including their diastereomers or enantiomers, also as racemates or as an enantiomer mixture, in the form of their free base or acid or in the form of a salt formed with a physiological compatible acid or base, in particular the hydrochloride salt and sodium salt, for the production of a medicament for pain relief. The compounds according to the invention have proved analgesically effective and bind to the MK801 binding site of the ionotropic NMDA receptor.

It has also been found as a result of binding to the MK801 binding site that the compounds according to the invention of the general structure (I A), (I B) or (II) are very suitable for treating further medical conditions, in particular for treating epilepsy, schizophrenia, neurodegenerative conditions, in particular Alzheimer's disease, Huntington's disease and Parkinson's disease, cerebral ischaemias and infarcts, psychoses due to raised amino acid levels, cerebral oedemas, insufficiency states of the central nervous system, in particular in hypoxia and anoxia, AIDS dementia, encephalomyelitis, Tourette's syndrome, perinatal asphyxia and tinnitus. The present application also provides for the use of at least one compound according to the invention of the general structure (I A), (I B) or (II) including a pharmaceutically acceptable salt, for the production of a medicament for the treatment and/or prophylaxis of epilepsy, schizophrenia, neurodegenerative conditions, in particular Alzheimer's disease, Huntington's disease and Parkinson's disease, cerebral ischaemias and infarcts, psychoses due to raised amino acid levels, cerebral oedemas, insufficiency states of the central nervous system, in particular in hypoxia and anoxia, AIDS dementia, encephalomyelitis, Tourette's syndrome, perinatal asphyxia and/or tinnitus.

It has furthermore surprisingly been shown that the compounds according to the invention of the general formula (I A) and/or (I B) are suitable ligands, in particular pharmacologically active ligands, of nucleoside transport proteins and/or of adenosine kinase and/or of adenosine deaminase and/or of $A_1$ and/or of $A_2$ and/or of $A_3$ receptors.

It is known that adenosine and ATP (adenosine-5'-triphosphate) and the purinergic receptors (purinoreceptors; P1 and P2 receptors) binding the latter play a significant role in the transmission and propagation of sensory information both in peripheral nerves as well as in the dorsal horn (M. W. Salter, A. Sollevi, "Handbook of exp. pharmacol.", Chapter 13, (2001), pp. 371–401). In particular adenosine and ATP as well as the P1 and P2 receptors play a role in the development and propagation of pain. With the P1 and P2 receptors a distinction is made between the so-called ATP receptors (=P2 receptors) and the so-called adenosine receptors (=P1 receptors). Among these P1 receptors four sub-types have been identified up to the present time, namely $A_1$, $A_{2a}$, $A_{2b}$ and $A_3$, all of which belong to the family of G protein-coupled receptors (GPCR). (Hereinafter the two sub-types $A_{2a}$ and $A_{2b}$ will also be identified as $A_2$ sub-type.)

Other substances that also have an influence on the adenosine level in the body are adenosine kinase, which catalyses the conversion of adenosine into AMP (adenosine-5'-monophosphate), adenosine deaminase, which catalyses the hydrolytic deamination of adenosine and 2'-deoxyadenosine to, respectively, inosine and 2'-deoxyinosine, and the nucleoside transport proteins, which are involved in the transport of, inter alia, adenosine from the extracellular space into the cell and vice versa. The latter play a role in particular in neuropathic pain states.

On account of the properties that have now been discovered, the present invention also provides for the use of compounds of the general formula (I A) or (I B) in the form shown above or in the form of their acid(s) or their base(s) or in the form of one of their salts, in particular one of the physiologically compatible salts, or in the form of one of their solvates, in particular the hydrates; in the form of their racemate; in the form of the pure stereoisomers, in particular enantiomers or diastereomers, or in the form of mixtures of the stereoisomers, in particular of the enantiomers or diastereomers, in an arbitrary mixture ratio; in which $R^1$ and $R^2$ independently of one another denote H, O—$R^9$, S—$R^{10}$, $C_{1-12}$-alkyl, $C_{3-8}$-cycloalkyl, —$CH_2$—$C_{3-8}$-cycloalkyl, aryl, —($C_{1-6}$-alkyl)-aryl, heterocyclyl or —($C_{1-6}$ alkyl)-heterocyclyl, in which one of the radicals $R^1$ and $R^2$ is H and the other radical of $R^1$ and $R^2$ is not H, or in the case that one of the radicals $R^1$ and $R^2$ denotes aryl, the other radical of $R^1$ and $R^2$ denotes H or $C_{1-12}$-alkyl, $R^3$ and $R^4$ denote H, $C_{1-12}$-alkyl, $C_{3-8}$-cycloalkyl, —$CH_2$—$C_{3-8}$-cycloalkyl, aryl or —($C_{1-6}$-alkyl)-aryl in which at least one of the radicals $R^3$ and $R^4$ is H, or one of the radicals $R^1$ and $R^2$ together with one of the radicals $R^3$ and $R^4$ forms W, where W denotes $\alpha'$-$(CH_2)_n$-$\beta'$ where n=3, 4, 5 or 6, $\alpha'$-CH=CH—$CH_2$-$\beta'$, $\alpha'$-$CH_2$—CH=CH-$\beta'$, $\alpha'$-CH=CH—$CH_2$—$CH_2$-$\beta'$, $\alpha'$-$CH_2$—CH=CH—$CH_2$-$\beta'$, $\alpha'$-$CH_2$—$CH_2$—CH=CH-$\beta'$, $\alpha'$-O—$(CH_2)_m$-$\beta'$ where m=2, 3, 4 or 5,

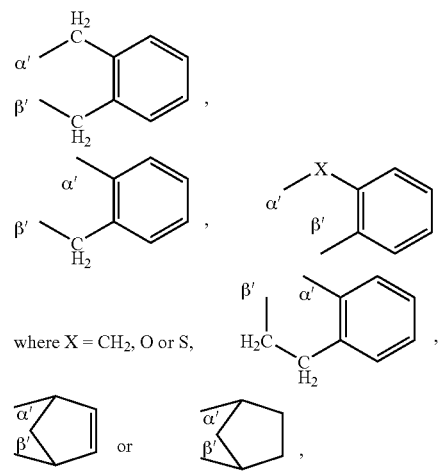

where X = $CH_2$, O or S, the end of W identified by $\alpha'$ is joined to the atom of the compound of the general formula (I A) and/or (I B) identified by $\alpha$, and the end of W identified by $\beta'$ is joined to the atom of the compound of the general structure (I A) and/or (I B) identified by $\beta$, the other radical of $R^1$ and $R^2$ is H or $C_{1-12}$-alkyl, and the other radical of $R^3$ and $R^4$ is H or $C_{1-2}$-alkyl;

$R^5$ denotes $C_{1-12}$-alkyl, $C_{3-8}$-cycloalkyl, —$CH_2$-$C_{3-8}$-cycloalkyl, aryl, —($C_{1-6}$ alkyl)-aryl, heterocyclyl, —($C_{1-6}$ alkyl)-heterocyclyl or C(=O)$R^{11}$;

$R^6$ denotes H, $C_{1-8}$-alkyl, —CN, fluorine, chlorine, bromine, iodine, $NO_2$, $NH_2$, $NHR^{12}$, $NR^{13}R^{14}$, $OR^{15}$, $S(O)_pR^{16}$ where p=0, 1 or 2, —C(=O)$R^{17}$ or —N=N-aryl;

$R^7$ denotes H, $C_{1-8}$-alkyl, aryl, —CN, fluorine, chlorine, bromine, iodine, $NO_2$, $NH_2$, $NHR^{12}$, $NR^{13}R^{14}$, $OR^{18}$, $S(O)_qR^{19}$ where q=0, 1 or 2 or denotes $C(=O)R^{20}$;

$R^9$ and $R^{10}$ independently of one another denote H, $C_{1-8}$-alkyl, $C_{3-8}$-cycloalkyl, —$CH_2$—$C_{3-8}$-cycloalkyl, aryl or —($C_{1-6}$-alkyl)-aryl;

$R^{11}$ denotes H, $C_{1-8}$-alkyl, $C_{3-8}$-cycloalkyl, —$CH_2$—$C_{3-8}$-cycloalkyl, aryl or $OR^{25}$;

$R^{12}$ denotes $C_{1-6}$-alkyl or —$CH_2$-aryl;

$R^{13}$ and $R^{14}$ are identical or different $C_{1-6}$-alkyl or together denote —$(CH_2)_h$— where h=4 or 5;

$R^{15}$ and $R^{16}$ independently of one another denote H, $C_{1-8}$-alkyl, $C_{3-8}$-cycloalkyl, —$CH_2$—$C_{3-8}$-cycloalkyl, aryl or —($C_{1-6}$-alkyl)-aryl;

$R^{17}$ denotes H, $C_{1-8}$-alkyl, $C_{3-8}$-cycloalkyl, —$CH_2$—$C_{3-8}$-cycloalkyl, aryl, —($C_{1-6}$-alkyl)-aryl, $NH_2$, $NHR^{12}$, $NR^{13}R^{14}$ or $OR^{26}$;

$R^{18}$ and $R^{19}$ independently of one another denote H, $C_{1-8}$-alkyl, $C_{3-8}$-cycloalkyl, —$CH_2$—$C_{3-8}$-cycloalkyl, aryl or —($C_{1-6}$-alkyl)-aryl;

$R^{20}$ denotes H, $C_{1-8}$-alkyl, $C_{3-8}$-cycloalkyl, —$CH_2$—$C_{3-8}$-cycloalkyl, aryl or —($C_{1-6}$-alkyl)-aryl or $OR^{27}$;

$R^{25}$, $R^{26}$, and $R^{27}$ independently of one another denote H or $C_{1-6}$-alkyl, where $R^{25}$ does not denote H if simultaneously $R^1$ denotes aryl and $R^2$ denotes alkyl;

for the prevention and/or treatment and for the production of a medicament for the prevention and/or treatment of medical conditions and/or illnesses that are influenced via a modulation, i.e., stimulation and/or inhibition, of nucleoside transport proteins and/or of adenosine kinase and/or of adenosine deaminase and/or of $A_1$ and/or of $A_2$ and/or of $A_3$ receptors.

Preferably the compounds of the general formula (1A) and/or (1B) are therefore used for the prevention and/or treatment of and for the production of a medicament for the prevention and/or treatment of pain, neuropathic pain, respiratory pathway conditions, cancer, cardiac arrythmias, ischaemias, epilepsy, Huntington's disease, malfunctions and diseases of the immune system, inflammatory conditions and diseases, neonatal hypoxia, neurodegenerative conditions, Parkinson's disease, kidney failure, schizophrenia, sleep disturbances, strokes, thromboses, urinary incontinence, diabetes, psoriasis, septic shock, cerebral trauma, glaucoma and/or congestive insufficiency. The compounds of the general formulae (I A) and/or (I B) have proved effective in treating these conditions. In addition side effects that normally occur when using conventional opioid analgesics are not or are only rarely observed with these compounds.

In addition the present invention also provides pharmaceutical compositions that contain at least one compound of the general structure (I A), (I B) or (II) defined above or one of their pharmaceutically acceptable salts and one or more pharmaceutical auxiliary substances. The medicaments and pharmaceutical compositions according to the invention may exist and be administered as liquid, semi-solid or solid medicament forms and in the form of for example injectable solutions, drops, juices, syrups, sprays, suspensions, granules, tablets, pellets, transdermal therapeutic systems, capsules, plasters, suppositories, ointments, creams, lotions, gels, emulsions or aerosols and, depending on the pharmaceutical form, contain in addition to at least one compound according to the invention of the general structure (I A), (I B) or (II), also pharmaceutical auxiliary substances such as for example carrier materials, fillers, solvents, diluents, surfactants, colourants, preservatives, release agents, intestinal lubricants, lubricants, aroma substances and/or binders.

These auxiliary substances may for example be water, ethanol, 2-propanol, glycerol, ethylene glycol, propylene glycol, polyethylene glycol, polypropylene glycol, glucose, fructose, lactose, sucrose, dextrose, molasses, starch, modified starch, gelatin, sorbitol, inositol, mannitol, microcrystalline cellulose, methylcellulose, carboxymethylcellulose, cellulose acetate, shellac, cetyl alcohol, polyvinylpyrrolidone, paraffins, waxes, natural and synthetic gums, gum arabic, alginates, dextran, saturated and unsaturated fatty acids, stearic acid, magnesium stearate, zinc stearate, glyceryl stearate, sodium lauryl sulfate, edible oils, sesame oil, coconut oil, groundnut oil, soya bean oil, lecithin, sodium lactate, polyoxyethylene and polyoxypropylene fatty acid esters, sorbitan fatty acid esters, sorbic acid, benzoic acid, citric acid, ascorbic acid, tannic acid, sodium chloride, potassium chloride, magnesium chloride, calcium chloride, magnesium oxide, zinc oxide, silicon dioxide, titanium oxide, titanium dioxide, magnesium sulfate, zinc sulfate, calcium sulfate, potassium carbonate, calcium phosphate, dicalcium phosphate, potassium bromide, potassium iodide, talcum, kaolin, pectin, crospovidone, agar and bentonite.

The choice of the auxiliary substances as well as the amounts thereof to be employed depends on whether the medicament is to be administered orally, subcutaneously, parenterally, intravenously, vaginally, pulmonarily, intraperitoneally, transdermally, intramuscularly, nasally, buccally, rectally or topically, for example to treat infections of the skin, mucous membranes and eyes. For oral administration, inter alia preparations in the form of tablets, sugar-coated pills, capsules, granules, drops, juices and syrups are suitable, while for parenteral, topical and inhalative application solutions, suspensions, readily reconstitutable powders for inhalation as well as sprays are suitable. Compounds according to the invention of the general structure (I A), (I B) or (II) in a depôt in dissolved form or in a plaster, optionally with the addition of agents promoting skin penetration, are suitable percutaneous application preparations. Preparation forms that may be used for rectal, transmucosal, parenteral and/or percutaneous administration may provide for the delayed release of the compounds according to the invention of the general structure (I A), (I B) or (II).

The production of the medicaments and pharmaceutical compositions according to the invention is carried out with the aid of agents, devices, methods and processes well known in the prior art relating to pharmaceutical formulations, such as are described for example in "Remington's Pharmaceutical Sciences", Ed. A. R. Gennaro, 17$^{th}$ Edition, Mack Publishing Company, Easton, Pa. (1985), in particular in Part 8, Chapters 76 to 93.

Thus for example for a solid formulation such as a tablet, the active constituent of the medicament, i.e. a compound of the general structure (I A), (I B) or (II) or one of its pharmaceutically acceptable salts, may be granulated with a pharmaceutical carrier, for example customary tablet constituents such as maize starch, lactose, sucrose, sorbitol, talcum, magnesium stearate, dicalcium phosphate or pharmaceutically acceptable gums, and pharmaceutical diluents, such as for example water, in order to form a solid composition that contains a compound according to the invention or a pharmaceutically acceptable salt thereof in a state of homogeneous distribution. The expression "homogeneous distribution" is understood in the present context to mean that the active substance is distributed uniformly throughout the whole composition so that the latter can be directly subdivided into equally effective unit-dose forms such as tablets, pills or capsules. The solid composition is then subdivided into unit-dose forms. The tablets or pills of the medicament according to the invention and/or of the compositions according to the invention may also be coated or otherwise compounded in order to provide a delayed-release dose form. Suitable coating agents include, inter alia, polymeric acids and mixtures of polymeric acids with materials such as for example shellac, cetyl alcohol and/or cellulose acetate.

The amount of active substance to be administered to the patient varies and depends on the patient's weight, age and medical history, as well as on the type of application, medical indications and severity of the condition.

Normally 0.1 to 5000 mg/kg, in particular 1 to 500 mg/kg and preferably 2 to 250 mg/kg bodyweight of at least one compound according to the invention of the general structure (I A), (I B) or (II) are administered.

The following examples serve to describe the present invention in more detail:

EXAMPLES

The chemicals and solvents that were used were obtained commercially from one of the following suppliers: Acros, Geel; Avocado, Port of Heysham; Aldrich, Deisenhofen; Fluka, Seelze; Lancaster, Mülheim; Maybridge, Tintagel; Merck, Darmstadt; Sigma, Deisenhofen; TCI, Japan; or are prepared according to processes generally known in the prior art.

General Operating Protocol (Semi-Automated Synthesis)

A threaded round-bottom glass tube (diameter 16 mm, length 125 mm) was fitted with a stirrer and sealed with a screw cap provided with a septum. The tube was placed in a stirring block adjusted to a temperature of 20° C. The following reagents were then successively pipetted in:

1. 1 ml of a solution containing 0.1 M trifluoroacetic acid and 0.1 M heterocyclylamine component (III) or (VI), in acetonitrile
2. 1 ml of a 0.11 M aldehyde (IV) solution in acetonitrile
3. 1 ml of a 0.3 M olefin (V) solution in acetonitrile The reaction mixture was stirred for 600 minutes at 20° C. in one of the stirring blocks. The reaction solution was then filtered off at the filtration station. The test tube was rinsed twice with 1.5 ml of a 7.5% $NaHCO_3$ solution. The rack together with the samples was placed manually on the working-up unit. 2 ml of diethyl ether were added to the reaction mixture in a Vortexer and shaken. The mixture was briefly centrifuged to form a phase boundary. The phase boundary was optically detected and the organic phase was pipetted off.

In the next step 2 ml of diethyl ether were again added to the aqueous phase, the whole was shaken and centrifuged, and the organic phase was pipetted off. The combined organic phases were dried over 2.4 g of granulated $MgSO_4$. The solvent was removed in a vacuum centrifuge.

Each sample was analysed by means of ESI-MS and/or NMR.

Mass spectroscopy investigations (ESI-MS) were carried out with an LCQ Classic mass spectrometer from the Finnegan company. $^1$H-NMR investigations of the compounds according to the invention were carried out with a 300 MHz DPX Advance NMR apparatus from Bruker.

The example compounds 1–144, 146–151 as well as 153 and 154 were prepared according to the aforedescribed general operating protocol (see Table 1).

TABLE 1

| Exmp. | Name | Calculated Mol. Wt. | Found Mol. Wt. |
|---|---|---|---|
| 1 | 3-bromo-5-(5-nitrofuran-2-yl)-7-m-tolyltetrahydropyrazolo[1,5-a]pyrimidine | 403.24 | 403.2/405.1 |
| 2 | 3-bromo-7-(4-fluorophenyl)-7-methyl-5-(5-nitrofuran-2-yl)-tetrahydropyrazolo[1,5-a]pyrimidine | 421.23 | 421.1/423.0 |
| 3 | 3-bromo-7-naphthalin-2-yl-5-(5-nitrofuran-2-yl)-tetrahydropyrazolo[1,5-a]pyrimidine | 439.27 | 439.2/441.1 |
| 4 | 2-(3-bromo-7-m-tolyltetrahydropyrazolo[1,5-a]pyrimidin-5-yl)-cyclopropanecarboxylic acid ethyl ester | 404.31 | 404.5/406.4 |
| 5 | 2-[3-bromo-7-(4-bromophenyl)-tetrahydropyrazolo[1,5-a]pyrimidin-5-yl]-cyclopropanecarboxylic acid ethyl ester | 469.18 | 468.3/470.1/472.1 |
| 6 | 2-(3-bromo-7-naphthalin-2-yl-tetrahydropyrazolo[1,5-a]pyrimidin-5-yl)-cyclopropanecarboxylic acid ethyl ester | 440.34 | 440.5/442.5 |
| 7 | 3-bromo-7-(4-fluorophenyl)-7-methyl-5-(5-methylfuran-2-yl)-tetrahydropyrazolo[1,5-a]pyrimidine | 390.26 | 390.1/392.0 |
| 8 | 3-bromo-7-(3,4-dimethoxyphenyl)-tetrahydropyrazolo[1,5-a]-pyrimidine-5-carboxylic acid ethyl ester | 410.27 | 410.3/412.2 |
| 9 | 3-bromo-7-(4-methoxyphenyl)-tetrahydropyrazolo[1,5-a]-pyrimidine-5-carboxylic acid ethyl ester | 380.24 | 380.2/382.1 |

TABLE 1-continued

| Exmp. | Name | Calculated Mol. Wt. | Found Mol. Wt. |
|---|---|---|---|
| 10 | 3-bromo-7-(4-methoxyphenyl)-tetrahydropyrazolo[1,5-a]-pyrimidine-5-carboxylic acid | 352.19 | 354.2 |
| 11 | 3-bromo-7-(2,4-dimethylphenyl)-5-(5-nitrofuran-2-yl)-tetrahydropyrazolo[1,5-a]pyrimidine | 417.26 | 417.1/419.0 |
| 12 | 3-bromo-7-(4-methoxyphenyl)-5-(5-nitrofuran-2-yl)-tetrahydropyrazolo[1,5-a]pyrimidine | 419.23 | 419.0/421.0 |
| 13 | 5,5a,6,8a-tetrahydro-3H-1,4,8b-triaza-as-indacene-3,5-dicarboxylic acid diethyl ester; 5,5a,6,8a-tetrahydro-4H-1,4,8b-triaza-as-indacene-3,5-dicarboxylic acid diethyl ester | 305.33 | 306.1 |
| 14 | 2-hydroxy-3-phenylazo-5,5a,6,8a-tetrahydro-3H-1,4,8b-triaza-as-indacene-5-carboxylic acid ethyl ester; 2-hydroxy-3-phenylazo-5,5a,6,8a-tetrahydro-4H-1,4,8b-triaza-as-indacene-5-carboxylic acid ethyl ester | 353.38 | 354.3 |
| 15 | 2-tert.-butyl-5,5a,6,8a-tetrahydro-3H-1,4,8b-triaza-as-indacene-5-carboxylic acid ethyl ester; 2-tert.-butyl-5,5a,6,8a-tetrahydro-3H-1,4,8b-triaza-as-indacene-5-carboxylic acid ethyl ester | 289.37 | 290.3 |
| 16 | 3-bromo-2-phenyl-5,5a,6,8a-tetrahydro-3H-1,4,8b-triaza-as-indacene-5-carboxylic acid ethyl ester; 3-bromo-2-phenyl-5,5a,6,8a-tetrahydro-4H-1,4,8b-triaza-as-indacene-5-carboxylic acid ethyl ester | 388.26 | 388.2/390.1 |
| 17 | 7-(2,3,4-trimethoxyphenyl)-tetrahydropyrazolo[1,5-a]pyrimidine-3,5-dicarboxylic acid diethyl ester | 433.46 | 434.4 |
| 18 | 3-cyano-2-methylsulfanyl-7-(2,3,4-trimethoxyphenyl)-tetrahydropyrazolo[1,5-a]pyrimidine-5-carboxylic acid ethyl ester | 432.49 | 433.2 |
| 19 | 2-hydroxy-7-(4-hydroxyphenyl)-6-methyl-3-phenylazo-tetrahydropyrazolo[1,5-a]pyrimidine-5-carboxylic acid ethyl ester | 421.45 | 422.4 |
| 20 | 3-bromo-7-(4-hydroxyphenyl)-6-methyl-2-phenyltetrahydropyrazolo-[1,5-a]pyrimidine-5-carboxylic acid ethyl ester | 456.34 | 456.4/458.4 |
| 21 | 5,5a,6,10b-tetrahydro-3H-1,4,10c-triazacyclopenta[c]fluorene-3,5-dicarboxylic acid diethyl ester; 5,5a,6,10b-tetrahydro-4H-1,4,10c-triazacyclopenta[c]fluorene-3,5-dicarboxylic acid diethyl ester | 355.39 | 356.2 |
| 22 | 2-hydroxy-3-phenylazo-5,5a,6,10b-tetrahydro-3H-1,4,10c-triazacyclopenta[c]fluorene-5-carboxylic acid ethyl ester; 2-hydroxy-3-phenylazo-5,5a,6,10b-tetrahydro-4H-1,4,10c-triazacyclopenta[c]fluorene-5-carboxylic acid ethyl ester | 403.44 | 404.3 |
| 23 | 7-phenylsulfanyltetrahydropyrazolo-[1,5-a]pyrimidine-3,5-dicarboxylic acid diethyl ester | 375.44 | 376.2 |
| 24 | 3-cyano-2-methylsulfanyl-7-phenylsulfanyltetrahydropyrazolo[1,5-a]pyrimidine-5-carboxylic acid ethyl ester | 374.48 | 375.1 |
| 25 | 3-cyano-2-methylsulfanyl-7-(2,3,4-trimethoxyphenyl)-tetrahydropyrazolo[1,5-a]pyrimidine-5-carboxylic acid | 404.44 | 405.2 |
| 26 | 7-phenylsulfanyltetrahydropyrazolo-[1,5-a]pyrimidine-3,5-dicarbaxylic acid-3-ethyl ester | 347.39 | 348.2 |

TABLE 1-continued

| Exmp. | Name | Calculated Mol. Wt. | Found Mol. Wt. |
|---|---|---|---|
| 27 | 3-cyano-7-(2,4-dimethylphenyl)-2-methylsulfanyl-tetrahydropyrazolo-[1,5-a]pyrimidine-5-carboxylic acid ethyl ester | 370.47 | 371.2 |
| 28 | 3-cyano-7-(2,4-dimethylphenyl)-tetrahydropyrazolo[1,5-a]-pyrimidine-5-carboxylic acid ethyl ester | 324.38 | 325.2 |
| 29 | 7-(2,4-dimethylphenyl)-tetrahydropyrazolo[1,5-a]pyrimidine-3,5-dicarboxylic acid-3-ethyl ester | 343.38 | 344.2 |
| 30 | 3-bromo-7-(2,4-dimethylphenyl)-2-phenyltetrahydropyrazolo-[1,5-a]-pyrimidine-5-carboxylic acid | 426.31 | 426.2/428.1 |
| 31 | 3-cyano-7-(2,4-dimethylphenyl)-2-methylsulfanyltetrahydropyrazolo[1,5-a]pyrimidine-5-carboxylic acid | 342.42 | 343.2 |
| 32 | 3-cyano-7-(2,4-dimethylphenyl)-tetrahydropyrazolo-[1,5-a]pyrimidine-5-carboxylic acid | 296.32 | 297.2 |
| 33 | 3-cyano-7-(3,4-dimethoxyphenyl)-2-methylsulfanyltetrahydropyrazolo[1,5-a]pyrimidine-5-carboxylic acid | 374.41 | 376.2 |
| 34 | 7-(2,4-dimethylphenyl)-5-(5-nitrofuran-2-yl)tetrahydropyrazolo-[1,5-a]pyrimidine-3-carboxylic acid ethyl ester | 410.42 | 411.1 |
| 35 | 7-(2,4-dimethylphenyl)-5-(5-nitrofuran-2-yl)-3-phenylazotetrahydropyrazolo[1,5-a]pyrimidin-2-ol | 458.47 | 459.3 |
| 36 | 3-bromo-7-(2,4-dimethylphenyl)-5-(5-nitrofuran-2-yl)-2-phenylazotetrahydropyrazolo[1,5-a]pyrimidine | 493.36 | 493.2/495.1 |
| 37 | 7-(2,4-dimethylphenyl)-2-methylsulfanyl-5-(5-nitrofuran-2-yl)-tetrahydropyrazolo[1,5-a]-pyrimidine-3-carbonitrile | 409.46 | 410.1 |
| 38 | 7-(2,4-dimethylphenyl)-5-(5-nitrofuran-2-yl)-tetrahydropyrazolo[1,5-a]pyrimidine-3-carbonitrile | 363.37 | 364.1 |
| 39 | 3-bromo-7-(3,4-dimethoxyphenyl)-5-(5-nitrofuran-2-yl)-2-phenyl-tetrahydropyrazolo[1,5-a]pyrimidine | 525.36 | 525.4/527.1 |
| 40 | 7-(4-methoxyphenyl)-2-methylsulfanyl-5-(5-nitro-furan-2-yl)-tetrahydropyrazolo[1,5-a]-pyrimidine-3-carbonitrile | 411.43 | 412.9 |
| 41 | 7-(2,4-dimethylphenyl)-5-(2-ethoxycarbonylcyclo-propyl)-tetrahydropyrazolo[1,5-a]pyrimidine-3-carboxylic acid ethyl ester | 411.5 | 412.5 |
| 42 | 2-[7-(2,4-dimethylphenyl)-2-hydroxy-3-phenylazotetrahydropyrazolo[1,5-a]pyrimidin-5-yl]-cyclopropanecarboxylic acid ethyl ester | 459.54 | 460.3 |
| 43 | 2-[2-tert.-butyl-7-(2,4-dimethylphenyl)tetrahydropyrazolo[1,5-a]pyrimidin-5-yl]cyclopropanecarboxylic acid ethyl ester | 395.54 | 396.5 |
| 44 | 2-[3-bromo-7-(2,4-dimethylphenyl)-2-phenyltetra-hydropyrazolo[1,5-a]pyrimidin-5-yl]cyclopropanecarboxylic acid ethyl ester | 494.43 | 494.4/496.2 |
| 45 | 2-[3-cyano-7-(2,4-dimethylphenyl)-2-methylsulfanyltetrahydropyrazolo-[1,5-a]pyrimidin-5-yl]cyclopropanecarboxylic acid ethyl ester | 410.53 | 411.3 |
| 46 | 5-(2-ethoxycarbonylcyclopropyl)-7-(3-fluorophenyl)tetrahydropyrazolo-[1,5-a]pyrimidine-3-carboxylic acid ethyl ester | 401.43 | 402.2 |
| 47 | 2-[3-bromo-7-(3-bromophenyl)-2-phenyltetrahydropyrazolo[1,5-a]- | 545.28 | 544.3/546.1/548.0 |

TABLE 1-continued

| Exmp. | Name | Calculated Mol. Wt. | Found Mol. Wt. |
|---|---|---|---|
| | pyrimidin-5-yl]cyclopropanecarboxylic acid ethyl ester | | |
| 48 | 2-[7-(3-bromophenyl)-3-cyano-2-methylsulfanyltetrahydropyrazolo[1,5-a]pyrimidin-5-yl]cyclopropanecarboxylic acid ethyl ester | 461.38 | 461.2/463.0 |
| 49 | 7-(2,4-dimethylphenyl)-5-(5-nitrothiophen-2-yl)-3-phenylazotetrahydropyrazolo[1,5-a]pyrimidin-2-ol | 474.54 | 475.2 |
| 50 | 7-(2,4-dimethylphenyl)-2-methyl-sulfanyl-5-(5-nitrothiophen-2-yl)-tetrahydropyrazolo[1,5-a]-pyrimidine-3-carbonitrile | 425.53 | 426.1 |
| 51 | 7-(2,4-dimethylphenyl)-5-(5-nitrothiophen-2-yl)-tetrahydropyrazolo-[1,5-a]pyrimidine-3-carbonitrile | 379.44 | 380.1 |
| 52 | 7-(3,4-dimethoxyphenyl)-5-(5-nitrothiophen-2-yl)-tetrahydropyrazolo-[1,5-a]pyrimidine-3-carboxylic acid ethyl ester | 458.49 | 459.3 |
| 53 | 7-(3,4-dimethoxyphenyl)-5-(5-nitrothiophen-2-yl)-3-phenylazotetrahydropyrazolo[1,5-a]pyrimidin-2-ol | 506.54 | 507.2 |
| 54 | 3-bromo-7-(3,4-dimethoxyphenyl)-5-(5-nitrothiophen-2-yl)-2-phenyltetrahydropyrazolo[1,5-a]pyrimidine | 541.42 | 541.4/543.3 |
| 55 | 7-(3,4-dimethoxyphenyl)-2-methylsulfanyl-5-(5-nitrothiophen-2-yl)-tetrahydropyrazolo[1,5-a]-pyrimidine-3-carbonitrile | 457.53 | 458.1 |
| 56 | 7-(3,4-dimethoxyphenyl)-5-(5-nitrothiophen-2-yl)-tetrahydropyrazolo[1,5-a]pyrimidine-3-carbonitrile | 411.43 | 412.1 |
| 57 | 7-(4-methoxyphenyl)-5-(5-nitrothiophen-2-yl)-tetrahydropyrazolo-[1,5-a]pyrimidine-3-carboxylic acid ethyl ester | 428.46 | 429.1 |
| 58 | 5-[3-bromo-7-(4-methoxyphenyl)-2-phenyltetrahydropyrazolo[1,5-a]-pyrimidin-5-yl]-furan-2-carboxylic acid | 494.34 | 494.2/496.1 |
| 59 | 5-benzoyl-7-(2,4-dimethylphenyl)-tetrahydropyrazolo-[1,5-a]-pyrimidine-3-carboxylic acid ethyl ester | 403.48 | 404.2 |
| 60 | 5-benzoyl-7-(2,4-dimethylphenyl)-2-methylsulfanyltetrahydropyrazolo[1,5-a]pyrimidine-3-carbonitrile | 402.51 | 403.1 |
| 61 | 5-benzoyl-7-(2,4-dimethylphenyl)-tetrahydropyrazolo-[1,5-a]-pyrimidine-3-carbonitrile | 356.42 | 355.3/357.2 |
| 62 | 5-benzoyl-7-(3,4-dimethoxyphenyl)-tetrahydropyrazolo[1,5-a]-pyrimidine-3-carboxylic acid ethyl ester | 435.47 | 436.2 |
| 63 | [3-bromo-7-(3,4-dimethoxyphenyl)-2-phenyltetrahydro-pyrazolo[1,5-a]-pyrimidin-5-yl]phenylmethanone | 518.41 | 518.7/520.2 |
| 64 | 5-benzoyl-7-(3,4-dimethoxyphenyl)-2-methylsulfanyltetrahydropyrazolo-[1,5-a]pyrimidine-3-carbonitrile | 434.51 | 435.1 |
| 65 | 5-benzoyl-7-(3,4-dimethoxyphenyl)-tetrahydropyrazolo[1,5-a]-pyrimidine-3-carbonitrile | 388.42 | 389.1 |
| 66 | 5-benzoyl-7-(4-methoxyphenyl)-tetrahydropyrazolo-[1,5-a]-pyrimidine-3-carboxylic acid ethyl ester | 405.45 | 406.1 |
| 67 | 5-benzoyl-7-(4-methoxyphenyl)-2-methylsulfanyltetrahydropyrazolo-[1,5-a]pyrimidine-3-carbonitrile | 404.49 | 405.0 |
| 68 | 5-benzoyl-7-(4-methoxyphenyl)tetrahydropyrazolo-[1,5-a]pyrimidine-3-carbonitrile | 358.4 | 359.0 |

TABLE 1-continued

| Exmp. | Name | Calculated Mol. Wt. | Found Mol. Wt. |
|---|---|---|---|
| 69 | 5-benzoyl-7-(3-fluorophenyl)-tetrahydropyrazolo-[1,5-a]-pyrimidine-3-carboxylic acid ethyl ester | 393.41 | 394.4 |
| 70 | [3-bromo-7-(3-fluorophenyl)-2-phenyltetrahydropyrazolo[1,5-a]-pyrimidin-5-yl]-phenylmethanone | 476.35 | 476.3/478.3 |
| 71 | [3-bromo-7-(3-bromophenyl)-2-phenyltetrahydro-pyrazolo[1,5-a]-pyrimidin-5-yl]phenylmethanone | 537.26 | 538.4 |
| 72 | 7-(2,4-dimethylphenyl)-5-(4-phenoxyphenyltetrahydropyrazolo-[1,5-a]pyrimidine-3-carboxylic acid ethyl ester | 467.56 | 468.2 |
| 73 | 3-bromo-7-(2,4-dimethylphenyl)-5-(4-phenoxyphenyl)-2-phenyltetrahydro-pyrazolo[1,5-a]pyrimidine | 550.5 | 550.3/552.2 |
| 74 | 7-(2,4-dimethylphenyl)-2-methylsulfanyl-5-(4-phenoxyphenyl)-tetrahydropyrazolo[1,5-a]-pyrimidine-3-carbonitrile | 466.6 | 467.1 |
| 75 | 7-(2,4-dimethylphenyl)-5-(4-phenoxyphenyl)tetrahydropyrazolo-[1,5-a]pyrimidine-3-carbonitrile | 420.51 | 421.1 |
| 76 | 7-(3,4-dimethoxyphenyl)-5-(4-phenoxyphenyl)tetrahydropyrazolo-[1,5-a]pyrimidine-3-carboxylic acid ethyl ester | 499.56 | 500.2 |
| 77 | 7-(3,4-dimethoxyphenyl)-2-methylsulfanyl-5-(4-phenoxyphenyl)-tetrahydropyrazolo[1,5-a]-pyrimidine-3-carbonitrile | 498.6 | 499.1 |
| 78 | 3-[3-cyano-7-(4-hydroxyphenyl)-6-methyltetrahydropyrazolo[1,5-a]-pyrimidin-5-yl]-2-hydroxybenzoic acid | 390.39 | 391.1 |
| 79 | 3-(3-cyano-5,5a,6,10b-tetrahydro-3H-1,4,10c-triazacyclopenta[c]-fluoren-5-yl)-2-hydroxybenzoic acid; 3-(3-cyano-5,5a,6,10b-tetrahydro-4H-1,4,10c-triazacyclopenta[c]fluoren-5-yl)-2-hydroxybenzoic acid | 372.38 | 373.0 |
| 80 | 3-(3-cyano-7-phenylsulfanyltetrahydropyrazolo[1,5-a]pyrimidin-5-yl]-2-hydroxybenzoic acid | 392.43 | 392.9 |
| 81 | 3-[2-tert.-butyl-7-(4-chloro-phenyl)-7-methyltetrahydropyrazolo-[1,5-a]pyrimidin-5-yl]-2-hydroxybenzoic acid | 439.94 | 440.2 |
| 82 | 5-(4-hydroxy-3-methoxyphenyl)-7-(4-hydroxyphenyl)-6-methyltetrahydropyrazolo[1,5-a]pyrimidine-3-carboxylic acid ethyl ester | 423.46 | 424.1 |
| 83 | 5-(4-hydroxy-3-methoxyphenyl)-7-(4-hydroxyphenyl)-6-methyltetrahydropyrazolo[1,5-a]pyrimidine-3-carbonitrile | 376.41 | 377.1 |
| 84 | 5-(4-hydroxy-3-methoxyphenyl)-5,5a,6,10b-tetrahydro-3H-1,4,10c-triazacyclopenta[c]fluorene-3-carboxylic acid ethyl ester; 5-(4-hydroxy-3-methoxyphenyl)-5,5a,6,10b-tetrahydro-4H-1,4,10c-triazacyclopenta[c]fluorene-3-carboxylic acid ethyl ester | 405.45 | 406.0 |
| 85 | 4-(2-tert.-butyl-5,5a,6,10b-tetrahydro-3H-1,4,10c-triazacyclopenta[c]fluoren-5-yl)-2-methoxyphenol; 4-(2-tert.-butyl-5,5a,6,10b-tetrahydro-4H-1,4,10c-triazacyclopenta[c]fluoren-5-yl)-2-methoxyphenol | 389.49 | 390.2 |

TABLE 1-continued

| Exmp. | Name | Calculated Mol. Wt. | Found Mol. Wt. |
|---|---|---|---|
| 86 | 5-(4-hydroxy-3-methoxyphenyl)-2-methylsulfanyl-5,5a,6,10b-tetrahydro-3H-1,4,10c-triazacyclopenta[c]fluorene-3-carbonitrile; 5-(4-hydroxy-3-methoxyphenyl)-2-methylsulfanyl-5,5a,6,10b-tetrahydro-3H-1,4,10c-triazacyclopenta[c]fluorene-3-carbonitrile | 404.49 | 404.9 |
| 87 | 5-(4-hydroxy-3-methoxyphenyl)-7-phenylsulfanyltetrahydropyrazolo[1,5-a]pyrimidine-3-carboxylic acid ethyl ester | 425.5 | 426.0 |
| 88 | 4-(2-tert.-butyl-7-phenylsulfanyltetrahydro-pyrazolo[1,5-a]-pyrimidin-5-yl)-2-methoxyphenol | 409.55 | 410.1 |
| 89 | 4-(3-bromo-2-phenyl-7-phenylsulfanyl-tetrahydro-pyrazolo[1,5-a]pyrimidin-5-yl)-2-methoxyphenol | 508.44 | 508.2/510.0 |
| 90 | 5-(2-hydroxy-3-methoxyphenyl)-7-phenylsulfanyltetrahydropyrazolo-[1,5-a]pyrimidine-3-carboxylic acid ethyl ester | 425.5 | 425.0 |
| 91 | 7-(4-chlorophenyl)-5-(2-hydroxy-3-methoxyphenyl)-7-methyltetrahydropyrazolo[1,5-a]pyrimidine-3-carboxylic acid ethyl ester | 441.91 | 441.0 |
| 92 | 5-(4-hydroxybutyl)-5,5a,6,10b-tetrahydro-3H-1,4,10c-triazacyclopenta[c]fluorene-3-carbonitrile; 5-(4-hydroxybutyl)-5,5a,6,10b-tetrahydro-4H-1,4,10c-triazacyclopenta-[c]fluorene-3-carbonitrile | 308.38 | 309.3 |
| 93 | 5-(4-hydroxybutyl)-2-methylsulfanyl-7-phenyl-sulfanyltetrahydropyrazolo[1,5-a]pyrimidine-3-carbonitrile | 374.52 | 375.2 |
| 94 | 5-(4-hydroxybutyl)-7-phenylsulfanyltetrahydro-pyrazolo[1,5-a]pyrimidine-3-carbonitrile | 328.43 | 329.2 |
| 95 | 7-(4-chlorophenyl)-5-(4-hydroxybutyl)-7-methyltetrahydropyrazolo[1,5-a]pyrimidine-3-carbonitrile | 344.84 | 345.1 |
| 96 | 5-butyl-2-methylsulfanyl-5,5a,6,10b-tetrahydro-3H-1,4,10c-triazacyclopenta[c]fluorene-3-carbonitrile; 5-butyl-2-methylsulfanyl-5,5a,6,10b-tetrahydro-4H-1,4,10c-triazacyclopenta[c]-fluorene-3-carbonitrile | 338.47 | 339.3 |
| 97 | 5-butyl-2-methylsulfanyl-7-phenylsulfanyltetrahydropyrazolo-[1,5-a]pyrimidine-3-carbonitrile | 358.52 | 359.2 |
| 98 | 5-butyl-7-phenylsulfanyltetrahydropyrazolo[1,5-a]pyrimidine-3-carbonitrile | 312.43 | 313.1 |
| 99 | 5-butyl-7-(4-chlorophenyl)-7-methylsulfanyltetrahydropyrazolo[1,5-a]pyrimidine-3-carbonitrile | 374.93 | 375.3 |
| 100 | 5-cyclopropyl-7-(2,4-dimethylphenyl)-3-phenylazotetrahydro-pyrazolo[1,5-a]pyrimidin-2-ol | 387.48 | 388.5 |
| 101 | 2-tert.-butyl-5-cyclopropyl-7-(2,4-dimethylphenyl)-tetrahydropyrazolo-[1,5-a]pyrimidine | 323.48 | 324.6 |
| 102 | 5-cyclopropyl-7-(2,4-dimethylphenyl)-2-methylsulfanyltetrahydropyrazolo[1,5-a]-pyrimidine-3-carbonitrile | 338.47 | 339.8 |
| 103 | 2-tert.-butyl-5-cyclopropyl-7-(3,4-dimethoxyphenyl)tetrahydropyrazolo-[1,5-a]pyrimidine | 355.48 | 356.3/357.6 |
| 104 | 3-bromo-5-cyclopropyl-7-(3,4-dimethoxyphenyl)-2-phenyltetrahydropyrazolo[1,5-a]pyrimidine | 454.37 | 454.3/456.1 |

TABLE 1-continued

| Exmp. | Name | Calculated Mol. Wt. | Found Mol. Wt. |
|---|---|---|---|
| 105 | 5-cyclopropyl-7-(4-methoxyphenol)-tetrahydropyrazolo[1,5-a]-pyrimidine-3-carboxylic acid ethyl ester | 341.41 | 342.7 |
| 106 | 5-cyclopropyl-3,5,5a,6,7,11b-hexahydro-1,4,11c-triazacyclopenta-[c]phenanthrene-3-carbonitrile | 290.36 | 291.4 |
| 107 | 7-(2,4-dimethylphenyl)-5-pyridin-2-yl-tetrahydro-pyrazolo[1,5-a]-pyrimidine-3-carboxylic acid ethyl ester | 376.45 | 377.3/378.4 |
| 108 | 7-(2,4-dimethylphenyl)-3-phenylazo-5-pyridin-2-yl-tetrahydropyrazolo-[1,5-a]pyrimidin-2-ol | 424.5 | 425.3 |
| 109 | 3-bromo-7-(2,4-dimethylphenyl)-2-phenyl-5-pyridin-2-yl-tetrahydropyrazolo [1,5-a]pyrimidine | 459.39 | 459.7/462.2 |
| 110 | 7-(2,4-dimethylphenyl)-2-methylsulfanyl-5-pyridin-2-yl-tetrahydropyrazolo [1,5-a]pyrimidine-3-carbonitrile | 375.49 | 376.4 |
| 111 | 7-(3,4-dimethoxyphenyl)-2-methylsulfanyl-5-phenethyl-tetrahydropyrazolo [1,5-a]pyrimidine-3-carbonitrile | 434.56 | 435.3 |
| 112 | 7-(3,4-dimethoxyphenyl)-5-phenethyltetrahydropyrazolo[1,5-a]-pyrimidine-3-carbonitrile | 388.47 | 389.2 |
| 113 | 5-cyclopropyl-7-(2-hydroxyethoxy)-tetrahydropyrazolo[1,5-a]pyrimidine-3-carboxylic acid ethyl ester | 295.33 | 296.2 |
| 114 | 2-(2-tert.-butyl-5-cyclopropyltetrahydropyrazolo-[1,5-a]-pyrimidin-7-yloxy)-ethanol | 279.38 | 280.3 |
| 115 | 5-cyclopropyl-3,5,5a,6,7,8a-hexahydro-8-oxa-1,4,8b-triaza-as-indacene-3-carboxylic acid ethyl ester; 5-cyclopropyl-4,5,5a,6,7,8a-hexahydro-8-oxa-1,4,8b-triaza-as-indacene-3-carboxylic acid ethyl ester | 277.32 | 278.3 |
| 116 | 5-cyclopropyl-3-phenylazo-3,5,5a,6,7,8a-hexahydro-8-oxa-1,4,8b-triaza-as-indacen-2-ol; 5-cyclopropyl-3-phenylazo-4,5,5a,6,7,8a-hexahydro-8-oxa-1,4,8b-triaza-as-indacen-2-ol | 325.37 | 326.5 |
| 117 | 7-cyclohexyloxy-5-cyclopropyltetrahydropyrazolo[1,5-a]pyrimidin-3-carboxylic acid ethyl ester | 333.43 | 334.1 |
| 118 | 7-cyclohexyloxy-5-cyclopropyl-2-methylsulfanyltetrahydropyrazolo-[1,5-a]pyrimidine-3-carbonitrile | 332.46 | 333.2 |
| 119 | 7-(4-chlorophenyl)-5-cyclohexyltetrahydropyrazolo-[1,5-a]pyrimidin-3-carbonitrile | 340.85 | 341.4 |
| 120 | 5-cyclohexyl-7-(2-hydroxyethoxy)-tetrahydropyrazolo[1,5-a]-pyrimidine-3-carboxylic acid ethyl ester | 337.41 | 338.3 |
| 121 | 5-cyclohexyl-3,5,5a,6,7,8a-hexahydro-8-oxa-1,4,8b-triaza-as-indacene-3-carboxylic acid ethyl ester; 5-cyclohexyl-4,5,5a,6,7,8a-hexahydro-8-oxa-1,4,8b-triaza-as-indacene-3-carboxylic acid ethyl ester | 319.4 | 320.3 |
| 122 | 5-cyclohexyl-7-cyclohexyloxytetrahydropyrazolo-[1,5-a]-pyrimidine-3-carboxylic acid ethyl ester | 375.51 | 376.2 |
| 123 | 7-(2,4-dimethylphenyl)-3-phenylazo-5-propyl-tetrahydropyrazolo[1,5-a]-pyrimidin-2-ol | 389.5 | 390.5 |

TABLE 1-continued

| Exmp. | Name | Calculated Mol. Wt. | Found Mol. Wt. |
|---|---|---|---|
| 124 | 7-(2,4-dimethylphenyl)-2-methylsulfanyl-5-propyltetrahydropyrazolo[1,5-a]pyrimidine-3-carbonitrile | 340.49 | 341.3 |
| 125 | 5-tert.-butyl-7-(2,4-dimethylphenyl)-tetrahydropyrazolo[1,5-a]-pyrimidine-3-carboxylic acid ethyl ester | 355.48 | 356.1 |
| 126 | 2,5-di-tert.-butyl-7-(3,4-dimethoxyphenyl)tetrahydropyrazolo-[1,5-a]pyrimidine | 371.52 | 372.2 |
| 127 | 3-bromo-5-tert.-butyl-7-(3,4-dimethoxyphenyl)-2-phenyltetrahydropyrazolo[1,5-a]pyrimidine | 470.41 | 470.2/472.1 |
| 128 | 2-[3-cyano-6,7-bis-(4-methoxyphenyl)tetrahydropyrazolo-[1,5-a]pyrimidin-5-yl]-cyclopropanecarboxylic acid ethyl ester | 472.54 | 473.0 |
| 129 | 3-cyano-6,7-bis-(4-methoxyphenyl)-tetrahydro-pyrazolo[1,5-a]-pyrimidine-5-carboxylic acid | 404.42 | 405.0 |
| 130 | 4-[3-bromo-6-methyl-2-phenyl-5-(4-trifluoromethylphenyl)tetrahydropyrazolo[1,5-a]pyrimidin-7-yl]-phenol | 528.37 | 528.1 |
| 131 | 7-(4-hydroxyphenyl)-6-methyl-2-methylsulfanyl-5-(4-trifluoromethylphenyl)tetrahydropyrazolo-[1,5-a]pyrimidine-3-carbonitrile | 444.47 | 445.1 |
| 132 | 7-(4-hydroxyphenyl)-6-methyl-5-(4-trifluoromethylphenyl)tetrahydropyrazolo[1,5-a]pyrimidine-3-carbonitrile | 398.38 | 399.1 |
| 133 | 2-(4-nitrophenylsulfonyl)-5-phenylsulfanyl-7-pyridin-2-yl-6,7-dihydro-5H-thiazolo[3,2-a]-pyrimidine | 510.61 | 511.2 |
| 134 | 3-(4-chlorophenyl)-5-phenylsulfanyl-7-pyridin-2-yl-6,7-dihydro-5H-thiazolo[3,2-a]-pyrimidine | 435.99 | 436.4 |
| 135 | 5-phenylsulfanyl-7-pyridin-2-yl-3-p-tolyl-6,7-dihydro-5H-thiazolo[3,2-a]pyrimidine | 415.58 | 416.3 |
| 136 | 7-methoxy-4-phenylsulfanyl-2-pyridin-2-yl-3,4-dihydro-2H-9-thia-1,4a-diazafluorene | 405.54 | 406.3 |
| 137 | 7-ethoxy-4-phenylsulfanyl-2-pyridin-2-yl-3,4-dihydro-2H-9-thia-1,4a-diazafluorene | 419.56 | 420.3 |
| 138 | 7-fluoro-4-phenylsulfanyl-2-pyridin-2-yl-3,4-dihydro-2H-9-thia-1,4a-diazafluorene | 393.5 | 394.2 |
| 139 | 3-naphthalin-2-yl-5-phenylsulfanyl-7-pyridin-2-yl-6,7-dihydro-5H-thiazolo[3,2-a]pyrimidine | 451.61 | 452.5 |
| 140 | 7-phenyl-3-phenylazo-5-pyridin-2-yl-3,5,6,7-tetrahydropyrazolo[1,5-a]pyrimidin-2-ol | 396.47 | 397.4 |
| 141 | 7-phenylsulfanyl-5-pyridin-2-yl-3,5,6,7-tetrahydropyrazolo[1,5-a]pyrimidine-3-carboxylic acid ethyl ester | 380.5 | 381.4 |
| 142 | 3-phenylazo-7-phenylsulfanyl-5-pyridin-2-yl-3,5,6,7-tetrahydropyrazolo[1,5-a]pyrimidin-2-ol | 428.51 | 429.6 |
| 143 | 3-bromo-7-phenylsulfanyl-5-pyridin-2-yl-3,5,6,7-tetrahydropyrazolo-[1,5-a]pyrimidine | 387.3 | 387.2 |
| 144 | 7-phenylsulfanyl-5-pyridin-2-yl-3,5,6,7-tetrahydropyrazolo[1,5-a]pyrimidine-3-carbonitrile | 333.41 | 334.2 |
| 146 | 7-(3,4-dimethoxyphenyl)-2-methylsulfanyl-5-pyridin-2-yl-tetrahydropyrazolo[1,5-a]pyrimidine-3-carbonitrile | 407.0 | 409.5/409.9 |

TABLE 1-continued

| Exmp. | Name | Calculated Mol. Wt. | Found Mol. Wt. |
|---|---|---|---|
| 147 | 3-bromo-7-(3,4-dimethoxyphenyl)-2-phenyl-5-pyridin-2-yl-tetrahydropyrazolo[1,5-a]pyrimidine | 490.9 | 492.6/494.4 |
| 148 | 3-bromo-7-(3,4-dimethoxyphenyl)-2-phenyltetrahydro-pyrazolo[1,5-a]pyrimidine-5-carboxylic acid ethyl ester | 485.9 | 486.5/488.4 |
| 149 | 3-bromo-7-(3,4-dimethoxyphenyl)-5-(5-nitrofuran-2-yl)-2-phenyl-tetrahydropyrazolo[1,5-a]pyrimidine | 524.9 | 525.4/527.1 |
| 150 | 3-cyano-7-(3,4-dimethoxyphenyl)-2-methylsulfanyltetrahydropyrazolo[1,5-a]pyrimidine-5-carboxylic acid ethyl ester | 402.0 | 402.5 |
| 151 | 3-cyano-7-(3,4-dimethoxyphenyl)-tetrahydropyrazolo-[1,5-a]-pyrimidine-5-carboxylic acid ethyl ester | 356.0 | 357.2 |
| 153 | 7-(3,4-dimethoxyphenyl)-2-methylsulfanyl-5-(5-nitrofuran-2-yl) tetrahydropyrazolo[1,5-a]-pyrimidine-3-carbonitrile | 441.5 | 442.1 |
| 154 | 7-(3,4-dimethoxyphenyl)-5-pyridin-2-yl-4,5,6,7-tetrahydropyrazolo-[1,5-a]pyrimidine-3-carboxylic acid ethyl ester | 408.5 | 409.5 |

Example 145

3-bromo-7-(3,4-dimethoxyphenyl)-2-phenyl-5-pyridin-2-yl-4,5,6,7-tetrahydropyrazolo[1,5-a]pyrimidine dihydrochloride 1.5 g of 5-amino-4-bromo-3-phenylpyrazole in acetonitrile were placed in a 100 ml single-necked flask, and 1.55 g of 3,4-dimethoxystyrene, 0.88 g of 2-pyridyl carbaldehyde and 0.72 ml of trifluoroacetic acid were added and the whole was stirred overnight at room temperature. The reaction solution was completely concentrated by evaporation. The crude product was purified by reversed phase HPLC. HPLC column: Macherey-Nagel, VP 100/21 Nucleosil 100-3 C18 HD (serial no. 0115186 batch 23710123):

Gradient: methanol (Riedel-de-Haen, Chromasolv)/water: gradient (4 stages) from 60% to 100% methanol in 37.5 minutes (flow rate 10 ml/min, injection volume: 1 ml) HPLC: Beckman SYSTEM GOLD, (Detector 166, Injector Endurance/SPARK, 125P Solvent Module, fraction collector: Foxy200/ISCO)

To form the hydrochloride 139 mg of 3-bromo-7-(3,4-dimethoxyphenyl)-2-phenyl-5-pyridin-2-yl-4,5,6,7-tetrahydropyrazolo[1,5-a]pyrimidine were dissolved in 1.1 ml of methyl ethyl ketone and then 6 µl of $H_2O$ and 7 µl of TMSCl were added. After some time a solid precipitated out. After suction filtration and washing with ether, yellow crystals were obtained that were dried under a vacuum.

$^1$H-NMR data (600 MHz; DMSO-d6): δ=8.68 (m, 1H), 8.27 (m, 1H), 7.92 (d, 1H, J=8.1 Hz), 7.74–7.67 (m, 3H), 7.39 (dd, 2H, J=7.5, 7.5 Hz), 7.33 (t, 1H, J=7.2 Hz), 6.83 (d, 1H, J=7.7 Hz), 6.78 (s, 1H), 6.66 (d, 1H, J=9.0 Hz), 5.47 (m, 1H), 5.03 (m, 1H), 3.71 (s, 3H), 3.69 (s, 3H), 2.67 (m, 1H), 2.59 (m, 1H).

Example 147

3-bromo-7-(3,4-dimethoxyphenyl)-2-phenyl-5-pyridin-2-yl-tetrahydropyrazolo[1,5-a]pyrimidine, prepared according to the process described above $^1$H-NMR data (600 MHz; DMSO-d6): δ=8.34 (br. s, 1H), 7.93 (d, 1H, J=3.8 Hz), 7.64 (s, 1H), 7.14 (d, 1H, J=4.5 Hz), 6.81 (d, 1H, J=8.3 Hz), 6.71 (s, 1H) 6.60 (d, 1H, J=8.3 Hz), 5.40 (dd, 1H J=4.5, 8.3 Hz), 5.09 (br. d, 1H, J=8.3 Hz), 3.70 (s, 3H), 3.68 (s, 3H), 2.59 (br. d, 1H, J=13.6 Hz), 2.50 (m, 1H).

Example 152

7-(3,4-dimethoxyphenyl)-5-pyridin-2-yl-4,5,6,7-tetrahydropyrazolo[1,5-a]pyrimidine-3-carbonitrile dihydrochloride 1 g (9.3 mmoles) of 3-aminopyrazole-4-carbonitrile was placed in 28 ml of acetonitrile, and 2.28 g (13.9 mmoles) of 3,4-dimethoxystyrene, 1.29 g (12 mmoles) of pyridine-2-carbaldehyde and 1.05 g (9.3 mmoles) of trifluoroacetic acid were added and the whole was stirred overnight at room temperature. The dark brown solution was completely concentrated by evaporation in a rotary evaporator and dried. The product was purified by HPLC (conditions as described above).

The base that was thereby obtained (270 mg) was suspended in methanol and 15 µl of $H_2O$ and 208 µl of TMSCl were then added. A clear solution was formed which was concentrated by evaporation on a Rotavapor. The yellow crystals that were formed were dried under a vacuum.

$^1$H-NMR data (600 MHz; DMSO-d6): δ=8.65 (d, 1H, J=4.8 Hz), 8.23 (t, 1H, J=7.2 Hz), 8.16 (m, 1H), 7.86 (d, 1H), 7.70–7.65 (m, 2H), 6.77 (d, 1H, J=8.3 Hz) 6.68 (s, 1H), 6.53

(d, 1H, J=8.3 Hz), 5.43 (dd, 1H, J=4.5, 7.5 Hz), 5.08 (m, 1H), 3.70 (s, 3H), 3.68 (s, 3H), 2.73 (m, 1H), 2.63 (br. d, 1H, J=14.3 Hz).

Example 56

Dihydrochloride

The dihydrochloride of 7-(3,4-dimethoxyphenyl)-5-(5-nitrothiophen-2-yl)-tetrahydropyrazolo[1,5-a]pyrimidine-3-carbonitrile was prepared in a similar manner to Examples 145 and 152.

$^1$H-NMR data (600 MHz; DMSO-d6): δ=8.65 (d, 1H, J=4.8 Hz), 8.23 (t, 1H, J=7.2 Hz), 8.16 (m, 1H), 7.86 (d, 1H), 7.70–7.65 (m, 2H), 6.77 (d, 1H, J=8.3 Hz) 6.68 (s, 1H), 6.53 (d, 1H, J=8.3 Hz), 5.43 (dd, 1H, J=4.5, 7.5 Hz), 5.08 (m, 1H), 3.70 (s, 3H), 3.68 (s, 3H), 2.73 (m, 1H), 2.63 (br. d, 1H, J=14.3 Hz).

Pharmacological Investigations:

The investigations to determine the NMDA antagonistic action of the compounds according to the invention were carried out on brain membrane homogenates (rat brain homogenate minus cerebellum, pons and medulla oblongata from male Wistar strain rats (Charles River, Sulzfeld, Germany)).

For this, freshly prepared rat brains were digested, after removal of the cerebellum, pons and medulla oblongata, in 50 mmole/l Tris/HCl (pH 7.7) in a Polytron homogeniser (model PT3000, Kinematika AG, Littau, Switzerland) at 6,000 revs. per minute (rpm) for 1 minute while cooling in ice and then centrifuged for 15 minutes at 4° C. and 60,000 g. The supernatant was decanted and discarded, and the membrane pellet was taken up again in 50 mmole/l of Tris/HCl (pH 7.7) and digested in a homogeniser at 2,000 rpm for 1 minute and recentrifuged for 15 minutes at 4° C. and 60,000 g. The supernatant was discarded again and the membrane pellet was homogenised in 50 mmole/l Tris/HCl (pH 7.7) (2,000 rpm for 1 minute) and aliquot portions were frozen at −70° C.

For the receptor binding test aliquots were in each case thawed out and then centrifuged for 15 minutes at 4° C. and 60,000 g. After decanting and discarding the supernatant, the membrane pellet for the binding test was taken up in binding test buffer and homogenised (2,000 rpm for 1 minute). 5 mmole/l Tris/HCl (pH 7.7) supplemented with 30 µmole/l of glycine and 100 µmole/l of glutamic acid was used as binding test buffer.

1 nmole/l of ($^3$H)-(+)-MK801 ((5R, 10S)-(+)-5-methyl-10,11-dihydro-5H-dibenzo(a,d)cyclohepten-5,10-imine (NET-972, NEN, Cologne, Germany) was added as radioactively labelled ligand. The proportion of non-specific binding was determined in the presence of 10 µmole/l of non-radioactively labelled (+)-MK801 (RBI/Sigma, Deisenhofen, Germany). In further assays the respective compounds according to the invention were added in concentration series and the displacement of the radioactive ligand from its specific binding to the NMDA receptor was measured.

The batches were incubated in each case for 40 minutes at 25° C. and then harvested by filtration to determine the radioactive ligand bound to the brain membrane homogenate. The radioactivity retained by the filter was measured after adding a scintillator ("Ready Protein" scintillator, Beckmann Coulter GmbH, Krefeld, Germany) in a β-counter (Packard TR$^1$-CARB Liquid Scintillation Analyser 2000CA, Packard Instrument, Meriden, Conn. 06450, USA).

The resulting percentage inhibition of the specific binding of the ligand ($^3$H)-(+)-MK801 in the presence of in each case 10 µmole/l of the respective compound according to the invention serves as a measure of the affinity of this compound for the (+)-MK801 binding site of the ionotropic NMDA receptor. The affinities are given in Table 2 as mean values of double determinations on selected examples.

TABLE 2

| Example | % Inhibition |
|---------|--------------|
| 140 | 44 |
| 141 | 45 |
| 142 | 75 |
| 143 | 49 |
| 144 | 45 |

The following test conditions were chosen for the determination of the inhibition of the nucleoside transport protein:

100 µl of the substance solution in aqueous solution with DMSO as solution aid were incubated for 30 minutes at 25° C. with 100 µl of 1.5 nM [$^3$H]NBI (N$^6$-benzyladenosine), 100 µl of buffer (50 mM Tris.HCl, pH 7.4) and 100 µl of an aqueous suspension of erythrocyte membrane. After the incubation the test mixture was filtered off (Whatman GF/C Filter, post-washed with 50 mM Tris.HCl). The filters were transferred to test tubes, 3.5 ml of scintillation fluid were added, and after 2 hours the radioactivity was measured in a β-counter. The measurement results (K$_i$ value at 10 µM and % displacement at 10 µM) are shown in Table 3.

TABLE 3

| Example No. | K$_i$ Value [µM] | % Displacement at 10 µM |
|-------------|------------------|-------------------------|
| 39 | | 40 |
| 53 | 0.6 | |
| 54 | 1.3 | |
| 55 | 0.4 | |
| 56 | | 43 |
| 64 | 0.6 | |
| 111 | 0.3 | |
| 145 | 0.4 | |
| 153 | | 50 |
| 154 | | 41 |

The dihydrochloride of Example 147 (prepared from Example 147 in a similar manner to Examples 145 and 152) was investigated as regards its affinity for the recombinant human adenosine A$_3$ receptor in a displacement assay (C. A. Salvatore et al., *Process. Natl. Acad. Sci. USA* (1993), Vol. 90, 10365–10369). At a ligand concentration of 0.1 nM [$^{125}$I]AB-MECA (N$^6$-(4-amino-3-[$^{125}$I]iodobenzyladenosine) the displacement at a concentration of 3 µM was 93%.

Pharmaceutical Formulation of a Medicament According to the Invention 1 g of the hydrochloride of 3-phenylazo-7-phenylsulfanyl-5-pyridin-2-yl-3,5,6,7-tetrahydropyrazolo[1,5-a]pyrimidin-2-ol was dissolved at room temperature in 1 l of water for injection purposes and then adjusted to isotonic conditions by addition of sodium chloride.

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations within the scope of the appended claims and equivalents thereof.

What is claimed is:

1. A compound corresponding to the structure (I A), (I B) or (II)

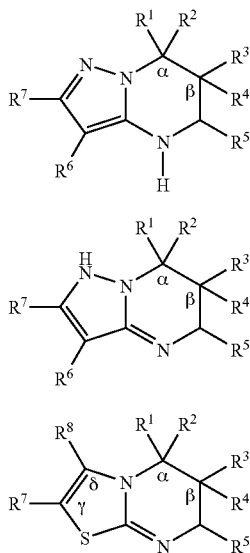

or a salt thereof, or a stereoisomer, mixture of stereoisomers having an arbitrary mixture ratio, or a racemic mixture thereof;
wherein
- $R^1$ and $R^2$ are independently selected from the group consisting of H, O—$R^9$, S—$R^{10}$, $C_{1-12}$-alkyl, $C_{3-8}$-cycloalkyl, —$CH_2$—$C_{3-8}$-cycloalkyl, aryl, —($C_{1-6}$-alkyl)-aryl, heterocyclyl or —($C_{1-6}$ alkyl)-heterocyclyl wherein exactly one of the radicals $R^1$ and $R^2$ is H, or wherein one of the radicals $R^1$ and $R^2$ is aryl and the other radical of $R^1$ and $R^2$ is H or $C_{1-12}$-alkyl,
- $R^3$ and $R^4$ are selected from the group consisting of H, $C_{1-12}$-alkyl, $C_{3-8}$-cycloalkyl, —$CH_2$—$C_{3-8}$-cycloalkyl, aryl or —($C_{1-6}$-alkyl)-aryl, wherein at least one of the radicals $R^3$ and $R^4$ is H, or
  one of the radicals $R^1$ and $R^2$ together with one of the radicals $R^3$ and $R^4$ form W, where W is α'-$(CH_2)_n$-β' where n=3, 4, 5 or 6, α'-CH=CH—$CH_2$-β', α'-$CH_2$—CH=CH-β', α'-CH=CH—$CH_2$—$CH_2$-β', α'-$CH_2$—CH=CH—$CH_2$-β', α'-$CH_2$—$CH_2$—CH=CH-β', or α'-O—$(CH_2)_m$-β' where m=2, 3, 4 or 5, or where W corresponds to

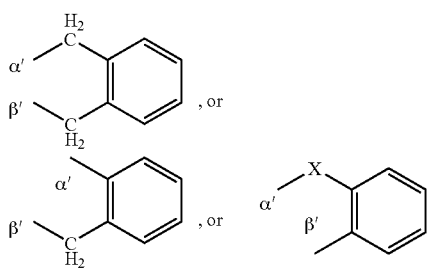

where X = $CH_2$, O or S,

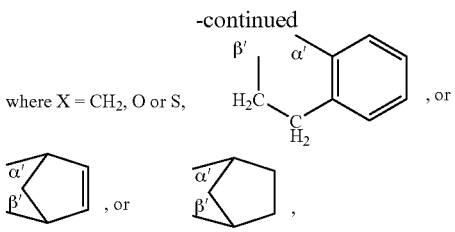

where the end of W identified by α' is joined to the atom identified by α in the compound corresponding to structure (I A), (I B) or (II), the end of W identified by β' is joined to the atom identified by β in the compound corresponding to structure (I A), (I B) or (II), the other radical of $R^1$ and $R^2$ is H or $C_{1-12}$-alkyl, and the other radical of $R^3$ and $R^4$ is H or $C_{1-12}$-alkyl;
- $R^5$ is $C_{1-12}$-alkyl, $C_{3-8}$-cycloalkyl, —$CH_2$—$C_{3-8}$-cycloalkyl, aryl, —($C_{1-6}$ alkyl)-aryl, heterocyclyl, —($C_{1-6}$ alkyl)-heterocyclyl or C(=O)$R^{11}$;
- $R^6$ is H, $C_{1-8}$-alkyl, —CN, fluorine, chlorine, bromine, iodine, $NO_2$, $NH_2$, $NHR^{12}$, $NR^{13}R^{14}$, $OR^{15}$, $S(O)_pR^{16}$ where p=0, 1 or 2, —C(=O)$R^{17}$ or —N=N-aryl;
- $R^7$ is H, $C_{1-8}$-alkyl, aryl, —CN, fluorine, chlorine, bromine, iodine, $NO_2$, $NH_2$, $NHR^{12}$, $NR^{13}R^{14}$, $OR^{18}$, $S(O)_qR^{19}$ where q=0, 1 or 2, or C(=O)$R^{20}$,
- $R^8$ is H, $C_{1-8}$-alkyl or aryl, or
- $R^7$ and $R^8$ together form Y, wherein Y is γ'-$CR^{21}$=$CR^{22}$—$CR^{23}$=$CR^{24}$-δ', where the end of Y identified by γ' is joined to the atom identified by γ in the compound corresponding to structure (II), and where the end of Y identified by δ' is joined to the atom identified by δ in the compound corresponding to structure (II);
- $R^9$ and $R^{10}$ are independently selected from the group consisting of H, $C_{1-8}$-alkyl, $C_{3-8}$-cycloalkyl, —$CH_2$—$C_{3-8}$-cycloalkyl, aryl and —($C_{1-6}$-alkyl)-aryl;
- $R^{11}$ is H, $C_{1-8}$-alkyl, $C_{3-8}$-cycloalkyl, —$CH_2$—$C_{3-8}$-cycloalkyl, aryl or $OR^{25}$;
- $R^{12}$ is $C_{1-6}$-alkyl or —$CH_2$-aryl;
- $R^{13}$ and $R^{14}$ are identical or different $C_{1-6}$-alkyl radicals, or together are —$(CH_2)_h$— and form a ring, where h=4 or 5;
- $R^{15}$ and $R^{16}$ are independently selected from the group consisting of H, $C_{1-8}$-alkyl, $C_{3-8}$-cycloalkyl, —$CH_2$—$C_{3-8}$-cycloalkyl, aryl and —($C_{1-6}$-alkyl)-aryl;
- $R^{17}$ is H, $C_{1-8}$-alkyl, $C_{3-8}$-cycloalkyl, —$CH_2$—$C_{3-8}$-cycloalkyl, aryl, —($C_{1-6}$-alkyl)-aryl, $NH_2$, $NHR^{12}$, $NR^{13}R^{14}$ or $OR^{26}$;
- $R^{18}$ and $R^{19}$ are independently selected from the group consisting of H, $C_{1-8}$-alkyl, $C_{3-8}$-cycloalkyl, —$CH_2$—$C_{3-8}$-cycloalkyl, aryl and —($C_{1-6}$-alkyl)-aryl;
- $R^{20}$ is H, $C_{1-8}$-alkyl, $C_{3-8}$-cycloalkyl, —$CH_2$—$C_{3-8}$-cycloalkyl, aryl or —($C_{1-6}$-alkyl)-aryl or $OR^{27}$;
- $R^{21}$, $R^{22}$, $R^{23}$ and $R^{24}$ are independently selected from the group consisting of H, fluorine, chlorine, bromine, iodine and $OR^{28}$;
- $R^{25}$, $R^{26}$, $R^{27}$ and $R^{28}$ are independently selected from the group consisting of H and $C_{1-6}$-alkyl, where $R^{25}$ is not H when both $R^1$ is aryl and $R^2$ is alkyl;
and wherein the compound is not
  4,5,6,7-tetrahydro-2-methyl-5,7-diphenylpyrazolo-[1,5-a]pyrimidine,
  4,5,6,7-tetrahydro-2,5-dimethyl-7-phenylpyrazolo-[1,5-a]pyrimidine, 4,5,6,7-tetrahydro-5,7-dimethyl-3-phenylpyrazolo-[1,5-a]pyrimidine, 4,5,6,7-tetrahydro-2,5,7-trimethylpyrazolo[1,5-a]pyrimidine, 4,5,6,7-tetrahydro-5,7-dimethyl-2-phenylpyrazolo-[1,5-a]pyrimidine, 4,5,6,7-tetrahydro-2-methyl-5,7-di-n-propylpyrazolo [1,5-a]pyrimidine-3-carbonitrile, 4,5,6,7-tetrahydro-5-methyl-7-[3-(trifluoromethyl)-phenyl]pyrazolo[1,5-a]pyrimidine-3-carbonitrile, 7-[4-(chloro)-phenyl]-4,5,6,7-tetrahydro-5-methylpyrazolo[1,5-a]pyrimidine-3-carbonitrile, 7-[3-(chloro)-phenyl]-4,5,6,7-tetrahydro-5-methylpyrazolo[1,5-a]pyrimidine-3-carbonitrile, 3,4-dihydro-2-(4-nitrophenyl)-4-phenyl-2H-pyrimido [2,1-b]benzothiazole, or 3,4-dihydro-4-(4-methylphenyl)-2-(4-nitrophenyl)-2H-pyrimido[2,1-b]benzothiazole.

2. A compound according to claim 1, wherein the compound is present as a physiologically compatible salt.

3. A compound according to claim 1, wherein the compound is present as a pure enantiomer or a pure diastereomer.

4. A compound according to claim 1, wherein the compound is present as a mixture of enantiomers or a mixture of stereoisomers.

5. A compound corresponding to the structure (I A), (I B) or (II)

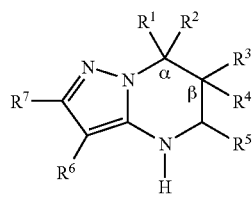

IA

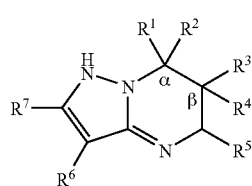

IB

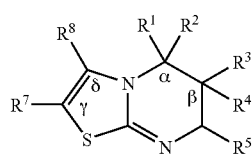

II or a salt thereof, or a stereoisomer, mixture of stereoisomers having an arbitrary mixture ratio, or a racemic mixture thereof;

wherein $R^1$ and $R^2$ are independently selected from the group consisting of H, O—$R^9$, S—$R^{10}$, $C_{1-6}$-alkyl, aryl' or —($C_{1-6}$-alkyl)-aryl', wherein aryl' is aryl$^1$, aryl$^2$, or aryl$^3$,

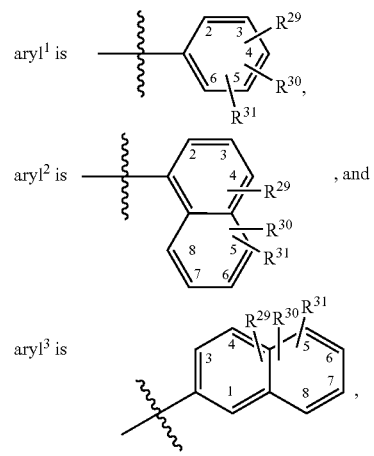

wherein exactly one of the radicals $R^1$ and $R^2$ is H, or wherein one of the radicals $R^1$ and $R^2$ is aryl' and the other radical of $R^1$ and $R^2$ is H or $C_{1-12}$-alkyl, and where $R^{29}$, $R^{30}$ and $R^{31}$ are independently selected from the group consisting of H, $C_{1-6}$-alkyl, F, Cl, Br, I, OH, O—$C_{1-6}$-alkyl, O-aryl$^1$ and O—$CH_2$-aryl$^1$, $R^3$ and $R^4$ are H, or unsubstituted, singly substituted or multiply substituted methyl, ethyl, n-propyl, 2-propyl, n-butyl, isobutyl, sec.-butyl, tert.-butyl, n-amyl, isoamyl, sec.-amyl, n-hexyl, isohexyl, sec.-hexyl, aryl' or —$CH_2$-aryl', where multiple substitution comprises replacement of multiple hydrogens bonded to one or more atoms by one or more substituents, and wherein at least one of the radicals $R^3$ and $R^4$ is H, or one of the radicals $R^1$ and $R^2$ together with one of the radicals $R^3$ and $R^4$ form W, where W is α'-CH=CH—$CH_2$-β', α'-CH=CH—$CH_2$—$CH_2$-β', or α'-O—$(CH_2)_m$- β' where m=2, 3, 4 or 5, or where W corresponds to

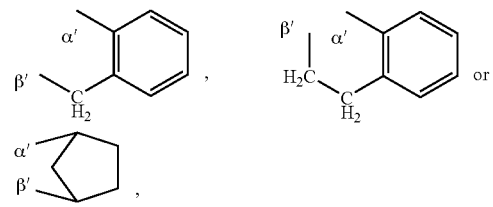

where the end of W identified by α' is joined to the atom identified by α in the compound corresponding to structure (I A), (I B) or (II), the end of W identified by β' is joined to the atom identified by β in the compound corresponding to structure (I A), (I B) or (II), the other radical of $R^1$ and $R^2$ is H, methyl, ethyl, n-propyl, 2-propyl, n-butyl, isobutyl, sec.-butyl, tert.-butyl, n-amyl, isoamyl, sec.-amyl, n-hexyl, isohexyl or sec.-hexyl and the other radical of $R^3$ and $R^4$ is H, methyl, ethyl, n-propyl, 2-propyl, n-butyl, isobutyl, sec.-butyl, tert.-butyl, n-amyl, isoamyl, sec.-amyl, n-hexyl, isohexyl, or sec.-hexyl;

$R^5$ is unsubstituted, singly substituted, or multiply substituted methyl, ethyl, n-propyl, 2-propyl, n-butyl, isobutyl, sec.-butyl, tert.-butyl, n-amyl, isoamyl, sec.-amyl, n-hexyl, isohexyl, sec.-hexyl, cyclopropyl, cyclobutyl, cyclopentyl, cyclohexyl or cycloheptyl, where multiple substitution comprises replacement of multiple hydrogens bonded to one or more atoms by one or more substituents, or $R^5$ is aryl', —(CH$_2$)$_k$-aryl' where k=1, 2, 3 or 4, heterocyclyl, or C(=O)R$^{11}$;

$R^6$ is H, methyl, ethyl, —CN, fluorine, chlorine, bromine, iodine, —C(=O)R$^{17}$ or —N=N-aryl$^1$;

$R^7$ is H, aryl$^1$, OR$^{18}$, S(O)$_q$R$^{19}$ where q=0, 1 or 2, or $R^7$ is unsubstituted, singly substituted, or multiply substituted methyl, ethyl, n-propyl, 2-propyl, n-butyl, isobutyl, sec.-butyl, tert.-butyl, n-amyl, isoamyl, sec.-amyl, n-hexyl, isohexyl or sec.-hexyl, where multiple substitution comprises replacement of multiple hydrogens bonded to one or more atoms by one or more substituents, $R^8$ is H or aryl', or the radicals $R^7$ and $R^8$ together form Y, where Y is γ'-CR$^{21}$=CR$^{22}$—CR$^{23}$=CR$^{24}$-δ', where the end of Y identified by γ' is joined to the atom identified by γ in the compound corresponding to structure (II), and the end of Y identified by δ' is joined to the atom identified by δ in the compound corresponding to structure (II);

$R^9$ is unsubstituted, singly substituted or multiply substituted methyl, ethyl, n-propyl, 2-propyl, n-butyl, isobutyl, sec.-butyl, tert.-butyl, n-amyl, isoamyl, sec.-amyl, n-hexyl, isohexyl, sec.-hexyl, cyclopropyl, cyclobutyl, cyclopentyl, cyclohexyl or cycloheptyl or is —[(CH$_2$)$_r$—O]$_s$—H where r=1, 2, 3, 4, 5 or 6 and s=1, 2, 3, 4, 5 or 6, where multiple substitution comprises replacement of multiple hydrogens bonded to one or more atoms by one or more substituents;

$R^{10}$ is aryl';

$R^{11}$ is aryl' or OR$^{25}$;

$R^{17}$ is OR$^{26}$;

$R^{18}$ is H or methyl;

$R^{19}$ is H, aryl$^1$, or unsubstituted, singly substituted or multiply substituted methyl, ethyl, n-propyl, 2-propyl, n-butyl, isobutyl, sec.-butyl, tert.-butyl, n-amyl, isoamyl, sec.-amyl, n-hexyl, isohexyl or sec.-hexyl, where multiple substitution comprises replacement of multiple hydrogens bonded to one or more atoms by one or more substituents;

$R^{21}$, $R^{22}$, $R^{23}$ and $R^{24}$ are independently selected from the group consisting of H, fluorine, chlorine, bromine, iodine and OR$^{28}$;

$R^{25}$ is H, methyl, ethyl, n-propyl, 2-propyl, n-butyl, isobutyl, sec.-butyl, tert.-butyl, n-amyl, isoamyl, sec.-amyl, n-hexyl, isohexyl or sec.-hexyl, where $R^{25}$ is not H when both $R^1$ is aryl and $R^2$ is alkyl;

$R^{26}$ is H, methyl, ethyl, n-propyl, 2-propyl, n-butyl, isobutyl, sec.-butyl, tert.-butyl, n-amyl, isoamyl, sec.-amyl, n-hexyl, isohexyl or sec.-hexyl;

$R^{28}$ is H, methyl or ethyl;

Heterocyclyl is furan-2-yl, furan-3-yl, thien-2-yl, thien-3-yl, pyridin-2-yl, pyridin-3-yl or pyridin-4-yl, where furanyl, thienyl and pyridinyl are unsubstituted, singly substituted or multiply substituted, and where multiple substitution comprises replacement of multiple hydrogens bonded to one or more atoms by one or more substituents;

$R^{29}$, $R^{30}$ and $R^{31}$, when occurring within $R^3$, $R^4$, $R^5$, $R^7$, $R^8$, $R^{10}$, $R^{11}$, or $R^{19}$, are independently selected from the group consisting of H, C$_{1-6}$-alkyl, C$_{3-8}$-cycloalkyl, (C$_{1-6}$ alkyl)-C$_{3-8}$-cycloalkyl, aryl, (C$_{1-6}$-alkyl)-aryl, heterocyclyl, (C$_{1-6}$ alkyl)-heterocyclyl, F, Cl, Br, I, —CN, —NC, —OR$^{32}$, —SR$^{33}$, —NO, —NO$_2$, NH$_2$, NHR$^{34}$, NR$^{35}$R$^{36}$, —N—OH, —N—OC$_{1-6}$-alkyl, —NHNH$_2$, —N=N-aryl, —(C=O)R$^{37}$, —(C=S)R$^{37}$, or

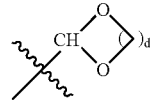

where d=1, 2 or 3, and may be in any arbitrary ring position;

$R^{32}$ and $R^{33}$ are independently selected from the group consisting of H, —C$_{1-6}$-alkyl, —C$_{3-8}$-cycloalkyl, —(C$_{1-6}$-alkyl)-C$_{3-8}$-cycloalkyl, -aryl, —(C$_{1-6}$-alkyl)-aryl, -heterocyclyl, —(C$_{1-6}$-alkyl)-heterocyclyl, (C=O)R$^{38}$, —[(CH$_2$)$_w$—O]$_z$—H or —[(CH$_2$)$_w$—O]$_z$—C$_{1-6}$-alkyl where w 1, 2, 3 or 4 and z=1, 2, 3, 4 or 5;

$R^{34}$ is C$_{1-6}$-alkyl, —CH$_2$-aryl or —(C=O)O-tert.-butyl;

$R^{35}$ and $R^{36}$ are C$_{1-6}$-alkyl or together are —(CH$_2$)$_g$— and form a ring where g=4 or 5;

$R^{37}$ is H, —C$_{1-6}$-alkyl, —C$_{3-8}$-cycloalkyl, —(C$_{1-6}$-alkyl)-C$_{3-8}$-cycloalkyl, -aryl, —(C$_{1-6}$-alkyl)-aryl, -heterocyclyl, —(C$_{1-6}$-alkyl)-heterocyclyl, —OR$^{39}$, —NH$_2$, —NHR$^{34}$, NR$^{35}$R$^{36}$;

$R^{38}$ is H, —C$_{1-6}$-alkyl, —C$_{3-8}$-cycloalkyl, —(C$_{1-6}$-alkyl)-C$_{3-8}$-cycloalkyl, -aryl, —(C$_{1-6}$-alkyl)-aryl; and $R^{39}$ is H, —C$_{1-6}$-alkyl, —C$_{3-8}$-cycloalkyl, —(C$_{1-6}$-alkyl)-C$_{3-8}$-cycloalkyl, -aryl, —(C$_{1-6}$-alkyl)-aryl, -heterocyclyl or —(C$_{1-6}$-alkyl)-heterocyclyl.

6. A compound according to claim 1, wherein $R^1$ and $R^2$ are independently selected from the group consisting of H, O—R$^9$, S—R$^{10}$, or unsubstituted, singly substituted, or multiply substituted methyl, ethyl, n-propyl, 2-propyl, n-butyl, tert.-butyl or n-hexyl, aryl' or —CH$_2$-aryl', where aryl' is aryl$^1$, aryl$^2$, or aryl$^3$,

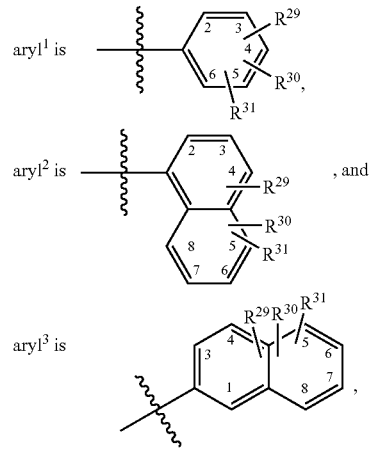

where $R^{29}$, $R^{30}$ and $R^{31}$ are independently selected from the group consisting of H, methyl, ethyl, 2-propyl, n-butyl, tert.-butyl, n-hexyl, F, Cl, Br, I, OH, O-methyl, and O-ethyl, wherein exactly one of $R^1$ and $R^2$ is H, or wherein one of the radicals $R^1$ and $R^2$ is aryl' and the other radical of $R^1$ and $R^2$ is H, methyl, ethyl, n-propyl, 2-propyl, n-butyl, tert.-butyl or n-hexyl, $R^3$ and $R^4$ are independently selected from the group consisting of H, methyl or aryl$^1$, wherein the aryl$^1$ substituents $R^{29}$, $R^{30}$ and $R^{31}$ are independent selected from the group consisting of H, methyl and O-methyl, wherein at least one of the radicals $R^3$ and $R^4$ is H, or one of the radicals $R^1$ and $R^2$ together with one of the radicals $R^3$ and $R^4$ form W, where W is $\alpha'$-CH=CH—CH$_2$-$\beta'$, $\alpha'$-CH=CH—CH$_2$—CH$_2$-$\beta'$, $\alpha'$-O—(CH$_2$)$_m$-$\beta'$ where m=2, 3, 4 or 5, or where W corresponds to

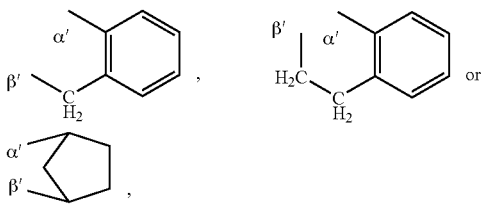

where the end of W identified by $\alpha'$ is joined to the atom identified by $\alpha$ in the compound corresponding to structure (I A), (I B) or (II), the end of W identified by $\beta'$ is joined to the atom identified by $\beta$ in the compound corresponding to structure (I A), (I B) or (II), and the other radical of $R^1$ and $R^2$ and the other radical of $R^3$ and $R^4$ is H;

$R^5$ is methyl, ethyl, n-propyl, 2-propyl, n-butyl, isobutyl, sec.-butyl, tert.-butyl, —(CH$_2$)$_4$—OH, cyclopropyl that is unsubstituted or singly substituted by C(=O)OH, C(=O)O-methyl or C(=O)O-ethyl, cyclopentyl, cyclohexyl, aryl$^1$ or —(CH$_2$)$_k$-aryl$^1$ where the aryl$^1$ substituents $R^{29}$, $R^{30}$ and $R^{31}$ are independently selected from the group consisting of H, —OH, —O-methyl, O—C$_6$H$_5$, CH$_3$, CF$_3$ or C(=O)OH and k=1 or 2, or $R^5$ is heterocyclyl or C(=O)R$^{11}$;

$R^6$ is H, —CN, bromine, —C(=O)R$^{17}$ or —N=N-phenyl;

$R^7$ is H, methyl, ethyl, n-propyl, 2-propyl, n-butyl, isobutyl, sec.-butyl or tert.-butyl, or aryl$^1$ where $R^{29}$, $R^{30}$ and $R^{31}$ are independently selected from the group consisting of H, OH, or S(O)$_q$R$^{19}$ where q=0 or 2, $R^8$ is H, aryl$^1$ where the aryl$^1$ substituents $R^{29}$, $R^{30}$ and $R^{31}$ are independently selected from the group consisting of H, methyl or chlorine, or aryl$^3$ where $R^{29}$, $R^{30}$ and $R^{31}$ are H, or the radicals $R^7$ and $R^8$ together form Y, where Y is $\gamma'$-CR$^{21}$=CR$^{22}$—CR$^{23}$=CR$^{24}$-$\delta'$, where the end of Y identified by $\gamma'$ is joined to the atom identified by $\gamma$ in the compound corresponding to structure (II), and the end of Y identified by $\delta'$ is joined to the atom identified by $\delta$ in the compound corresponding to structure (II);

$R^9$ is methyl, ethyl, n-propyl, 2-propyl, n-butyl, isobutyl, sec.-butyl, tert.-butyl, n-amyl, isoamyl, sec.-amyl, n-hexyl, isohexyl, sec.-hexyl, cyclopropyl, cyclopentyl, cyclohexyl, or —[(CH$_2$)$_r$—O]$_s$—H where r=1, 2 or 3 and s=1 or 2;

$R^{10}$ is aryl$^1$;

$R^{11}$ is aryl$^1$ where $R^{29}$, $R^{30}$ and $R^{31}$ are H or OR$^{25}$;

$R^{17}$ is OR$^{26}$;

$R^{19}$ is methyl or aryl$^1$, where one of the aryl$^1$ substituents $R^{29}$, $R^{30}$ and $R^{31}$ is H or —NO$_2$, and the two other aryl$^1$ substituents of $R^{29}$, $R^{30}$ and $R^{31}$ are H;

$R^{21}$ and $R^{23}$ are H;

$R^{22}$ is H, fluorine or OR$^{26}$;

$R^{24}$ is H or chlorine;

$R^{25}$ is H, methyl or ethyl, where $R^{25}$ is not H when $R^1$ is aryl and $R^2$ is alkyl;

$R^{26}$ is H, methyl or ethyl;

$R^{28}$ is methyl or ethyl; and

Heterocyclyl is furan-2-yl, furan-3-yl, thien-2-yl, thien-3-yl, pyridin-2-yl, pyridin-3-yl or pyridin-4-yl, where furanyl, thienyl and pyridinyl are unsubstituted, singly substituted, or multiply substituted by —NO$_2$, CH$_3$ or C(=O)OH, where multiple substitution comprises replacement of multiple hydrogens bonded to one or more atoms by one or more substituents.

7. A compound according to claim 1, wherein $R^1$ and $R^2$ are independently selected from the group consisting of H, O—CH$_2$—CH$_2$—OH, O-cyclohexyl, S-phenyl, methyl, phenyl, 3-fluorophenyl, 3-bromophenyl, 4-bromophenyl, 4-chlorophenyl, 4-fluorophenyl, 3-methylphenyl, 4-hydroxyphenyl, 4-methoxyphenyl, 2,4-dimethylphenyl, 3,4-dimethoxyphenyl, 2,3,4-trimethoxyphenyl, 2-naphthyl or —CH$_2$-phenyl, $R^3$ and $R^4$ are H, methyl or 4-methoxyphenyl, where at least one of $R^3$ and $R^4$ is H, or one of the radicals $R^1$ and $R^2$ together with one of the radicals $R^3$ and $R^4$ form W, where W is $\alpha'$-CH=CH—CH$_2$-$\beta'$, $\alpha'$-CH=CH—CH$_2$—CH$_2$-$\beta'$, or $\alpha'$-O—(CH$_2$)$_m$-$\beta'$ where m=2, 3, 4 or 5, or where W corresponds to

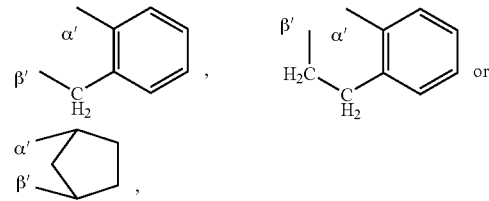

where the end of W identified by $\alpha'$ is joined to the atom identified by $\alpha$ in the compound corresponding to structure (I A), (I B) or (II), the end of W identified by $\beta'$ is joined to the atom identified by $\beta$ in the compound corresponding to structure (I A), (I B) or (II), and the other radical of $R^1$ and $R^2$ and the other radical of $R^3$ and $R^4$ are H;

$R^5$ is n-propyl, n-butyl, tert.-butyl, —(CH$_2$)$_4$—OH, cyclopropyl, cycloprop-2-yl-1-carboxylic acid ethyl ether, cyclohexyl, 4-trifluorophenyl, 4-phenoxyphenyl, 2-hydroxy-3-methoxyphenyl, 4-hydroxy-3-methoxyphenyl, 3-carboxy-2-hydroxy-phenyl, —(CH$_2$)$_2$-phenyl, 5-carboxyfuran-2-yl, 5-methylfuran-2-yl, 5-nitrofuran-2-yl, 5-nitro-thien-2-yl, pyridin-2-yl, pyridin-3-yl, C(=O)-phenyl, C(=O)OH or C(=O)Oethyl, where $R^5$ is not C(=O)OH when both $R^1$ is aryl and $R^2$ is alkyl;

$R^6$ is H, —CN, bromine, —C(=O)OH, —C(=O)Oethyl or —N=N-phenyl;

$R^7$ is H, phenyl, OH, —S-methyl, —SO$_2$-(4-nitrophenyl) or tert.-butyl;

$R^8$ is 4-chlorophenyl, 4-methylphenyl or 2-naphthyl; or the radicals $R^7$ and $R^8$ together form Y, where Y is $\gamma'$-CR$^{21}$=CR$^{22}$—CR$^{23}$=CR$^{24}$-$\delta'$, where the end of Y identified by $\gamma'$ is joined to the atom identified by $\gamma$ in the compound corresponding to structure (II), and the end of Y identified by $\delta'$ is joined to the atom identified by $\delta$ in the compound corresponding to structure (II); and $R^{21}$ is fluorine, methoxy or ethoxy.

8. A compound according to claim 1, wherein the compound is selected from the group consisting of:

3-bromo-5-(5-nitrofuran-2-yl)-7-m-tolyltetrahydro-pyrazolo[1,5-a]pyrimidine 3-bromo-7-(4-fluorophenyl)-7-methyl-5-(5-nitrofuran-2-yl)-tetrahydropyrazolo[1,5-a]pyrimidine 3-bromo-7-naphthalin-2-yl-5-(5-nitrofuran-2-yl)-tetrahydropyrazolo[1,5-a]pyrimidine 2-(3-bromo-7-m-tolyltetrahydropyrazolo[1,5-a]-pyrimidin-5-yl)-cyclopropanecarboxylic acid ethyl ester 2-[3-bromo-7-(4-bromophenyl)-tetrahydropyrazolo[1,5-a]pyrimidin-5-yl]-cyclopropanecarboxylic acid ethyl ester 2-(3-bromo-7-naphthalin-2-yl-tetrahydropyrazolo[1,5-a]pyrimidin-5-yl)-cyclopropanecarboxylic acid ethyl ester 3-bromo-7-(4-fluorophenyl)-7-methyl-5-(5-methyl-furan-2-yl)-tetrahydropyrazolo[1,5-a]pyrimidine 3-bromo-7-(3,4-dimethoxyphenyl)-tetrahydropyrazolo-[1,5-a]pyrimidine-5-carboxylic acid ethyl ester 3-bromo-7-(4-methoxyphenyl)-tetrahydropyrazolo[1,5-a]pyrimidine-5-carboxylic acid ethyl ester 3-bromo-7-(4-methoxyphenyl)-tetrahydropyrazolo[1,5-a]pyrimidine-5-carboxylic acid 3-bromo-7-(2,4-dimethylphenyl)-5-(5-nitrofuran-2-yl)-tetrahydropyrazolo[1,5-a]pyrimidine 3-bromo-7-(4-methoxyphenyl)-5-(5-nitrofuran-2-yl)-tetrahydropyrazolo[1,5-a]pyrimidine 5,5a,6,8a-tetrahydro-3H-1,4,8b-triaza-as-indacene-3,5-dicarboxylic acid diethyl ester; 5,5a,6,8a-tetrahydro-4H-1,4,8b-triaza-as-indacene-3,5-dicarboxylic acid diethyl ester 2-hydroxy-3-phenylazo-5,5a,6,8a-tetrahydro-3H-1,4,8b-triaza-as-indacene-5-carboxylic acid ethyl ester; 2-hydroxy-3-phenylazo-5,5a,6,8a-tetrahydro-4H-1,4,8b-triaza-as-indacene-5-carboxylic acid ethyl ester 2-tert.-butyl-5,5a,6,8a-tetrahydro-3H-1,4,8b-triaza-as-indacene-5-carboxylic acid ethyl ester; 2-tert.-butyl-5,5a,6,8a-tetrahydro-3H-1,4,8b-triaza-as-indacene-5-carboxylic acid ethyl ester 3-bromo-2-phenyl-5,5a,6,8a-tetrahydro-3H-1,4,8b-triaza-as-indacene-5-carboxylic acid ethyl ester; 3-bromo-2-phenyl-5,5a,6,8a-tetrahydro-4H-1,4,8b-triaza-as-indacene-5-carboxylic acid ethyl ester 7-(2,3,4-trimethoxyphenyl)-tetrahydropyrazolo[1,5-a]pyrimidine-3,5-dicarboxylic acid diethyl ester 3-cyano-2-methylsulfanyl-7-(2,3,4-trimethoxyphenyl)-tetrahydropyrazolo[1,5-a]pyrimidine-5-carboxylic acid ethyl ester 2-hydroxy-7-(4-hydroxyphenyl)-6-methyl-3-phenylazo-tetrahydropyrazolo[1,5-a]pyrimidine-5-carboxylic acid ethyl ester 3-bromo-7-(4-hydroxyphenyl)-6-methyl-2-phenyltetrahydropyrazolo[1,5-a]pyrimidine-5-carboxylic acid ethyl ester 5,5a,6,10b-tetrahydro-3H-1,4,10c-triazacyclopenta-[c]fluorene-3,5-dicarboxylic acid diethyl ester; 5,5a,6,10b-tetrahydro-4H-1,4,10c-triazacyclopenta[c]fluorene-3,5-dicarboxylic acid diethyl ester 2-hydroxy-3-phenylazo-5,5a,6,10b-tetrahydro-3H-1,4,10c-triazacyclopenta[c]fluorene-5-carboxylic acid ethyl ester; 2-hydroxy-3-phenylazo-5,5a,6,10b-tetrahydro-4H-1,4,10c-triazacyclopenta[c]fluorene-5-carboxylic acid ethyl ester 7-phenylsulfanyltetrahydropyrazolo[1,5-a]pyrimidine-3,5-dicarboxylic acid diethyl ester 3-cyano-2-methylsulfanyl-7-phenylsulfanyltetrahydropyrazolo[1,5-a]pyrimidine-5-carboxylic acid ethyl ester 3-cyano-2-methylsulfanyl-7-(2,3,4-trimethoxyphenyl)-tetrahydropyrazolo[1,5-a]pyrimidine-5-carboxylic acid 7-phenylsulfanyltetrahydropyrazolo[1,5-a]pyrimidine-3,5-dicarboxylic acid-3-ethyl ester 3-cyano-7-(2,4-dimethylphenyl)-2-methylsulfanyl-tetrahydropyrazolo[1,5-a]pyrimidine-5-carboxylic acid ethyl ester 3-cyano-7-(2,4-dimethylphenyl)-tetrahydropyrazolo-[1,5-a]pyrimidine-5-carboxylic acid ethyl ester 7-(2,4-dimethylphenyl)-tetrahydropyrazolo-[1,5-a]pyrimidine-3,5-dicarboxylic acid-3-ethyl ester 3-bromo-7-(2,4-dimethylphenyl)-2-phenyltetrahydropyrazolo-[1,5-a]pyrimidine-5-carboxylic acid 3-cyano-7-(2,4-dimethylphenyl)-2-methylsulfanyl-tetrahydropyrazolo[1,5-a]pyrimidine-5-carboxylic acid 3-cyano-7-(2,4-dimethylphenyl)-tetrahydropyrazolo-[1,5-a]pyrimidine-5-carboxylic acid 3-cyano-7-(3,4-dimethoxyphenyl)-2-methylsulfanyl-tetrahydropyrazolo[1,5-a]pyrimidine-5-carboxylic acid 7-(2,4-dimethylphenyl)-5-(5-nitrofuran-2-yl)-tetrahydropyrazolo[1,5-a]pyrimidine-3-carboxylic acid ethyl ester 7-(2,4-dimethylphenyl)-5-(5-nitrofuran-2-yl)-3-phenylazotetrahydropyrazolo[1,5-a]pyrimidin-2-ol 3-bromo-7-(2,4-dimethylphenyl)-5-(5-nitrofuran-2-yl)-2-phenylazotetrahydropyrazolo[1,5-a]pyrimidine 7-(2,4-dimethylphenyl)-2-methylsulfanyl-5-(5-nitrofuran-2-yl)-tetrahydropyrazolo[1,5-a]-pyrimidine-3-carbonitrile 7-(2,4-dimethylphenyl)-5-(5-nitrofuran-2-yl)-tetrahydropyrazolo[1,5-a]pyrimidine-3-carbonitrile 3-bromo-7-(3,4-dimethoxyphenyl)-5-(5-nitrofuran-2-yl)-2-phenyltetrahydropyrazolo[1,5-a]pyrimidine 7-(4-methoxyphenyl)-2-methylsulfanyl-5-(5-nitro-furan-2-yl)-tetrahydropyrazolo[1,5-a]pyrimidine-3-carbonitrile 7-(2,4-dimethylphenyl)-5-(2-ethoxycarbonylcyclo-propyl)-tetrahydropyrazolo[1,5-a]pyrimidine-3-carboxylic acid ethyl ester 2-[7-(2,4-dimethylphenyl)-2-hydroxy-3-phenylazo-tetrahydropyrazolo[1,5-a]pyrimidin-5-yl]-cyclopropanecarboxylic acid ethyl ester 2-[2-tert.-butyl-7-(2,4-dimethylphenyl)tetrahydro-pyrazolo[1,5-a]pyrimidin-5-yl]cyclopropanecarboxylic acid ethyl ester 2-[3-bromo-7-(2,4-dimethylphenyl)-2-phenyltetra-hydropyrazolo[1,5-a]pyrimidin-5-yl]cyclopropanecarboxylic acid ethyl ester 2-[3-cyano-7-(2,4-dimethylphenyl)-2-methylsulfanyl-tetrahydropyrazolo[1,5-a]pyrimidin-5-yl]-cyclopropanecarboxylic acid ethyl ester 5-(2-ethoxycarbonylcyclopropyl)-7-(3-fluorophenyl)-tetrahydropyrazolo[1,5-a]pyrimidine-3-carboxylic acid ethyl ester 2-[3-bromo-7-(3-bromophenyl)-2-phenyltetrahydro-pyrazolo[1,5-a]pyrimidin-5-yl]cyclopropane-carboxylic acid ethyl ester 2-[7-(3-bromophenyl)-3-cyano-2-methylsulfanyl-tetrahydropyrazolo[1,5-a]pyrimidin-5-yl]-cyclopropanecarboxylic acid ethyl ester 7-(2,4-dimethylphenyl)-5-(5-nitrothiophen-2-yl)-3-phenylazotetrahydropyrazolo[1,5-a]pyrimidin-2-ol 7-(2,4-dimethylphenyl)-2-methylsulfanyl-5-(5-nitrothiophen-2-yl)-tetrahydropyrazolo[1,5-a]-pyrimidine-3-carbonitrile 7-(2,4-dimethylphenyl)-5-(5-nitrothiophen-2-yl)-tetrahydropyrazolo[1,5-a]pyrimidine-3-carbonitrile 7-(3,4-dimethoxyphenyl)-5-(5-nitrothiophen-2-yl)-tetrahydropyrazolo[1,5-a]pyrimidine-3-carboxylic acid ethyl ester 7-(3,4-dimethoxyphenyl)-5-(5-nitrothiophen-2-yl)-3-phenylazotetrahydropyrazolo[1,5-a]pyrimidin-2-ol 3-bromo-7-(3,4-dimethoxyphenyl)-5-(5-nitrothiophen-2-yl)-2-phenyltetrahydropyrazolo[1,5-a]pyrimidine 7-(3,4-dimethoxyphenyl)-2-methylsulfanyl-5-(5-nitrothiophen-2-yl)-tetrahydropyrazolo[1,5-a]-pyrimidine-3-carbonitrile 7-(3,4-dimethoxyphenyl)-5-(5-nitrothiophen-2-yl)-tetrahydropyrazolo[1,5-a]pyrimidine-3-carbonitrile 7-(4-methoxyphenyl)-5-(5-nitrothiophen-2-yl)-tetrahydropyrazolo[1,5-a]pyrimidine-3-carboxylic acid ethyl ester 5-[3-bromo-7-(4-methoxyphenyl)-2-phenyltetrahydropyrazolo[1,5-a]pyrimidin-5-yl]-furan-2-carboxylic acid 5-benzoyl-7-(2,4-dimethylphenyl)-tetrahydropyrazolo-[1,5-a]pyrimidine-3-carboxylic acid ethyl ester 5-benzoyl-7-(2,4-dimethylphenyl)-2-methylsulfanyl-tetrahydropyrazolo[1,5-a]pyrimidine-3-carbonitrile 5-benzoyl-7-(2,4-dimethylphenyl)-tetrahydropyrazolo-[1,5-a]pyrimidine-3-carbonitrile 5-benzoyl-7-(3,4-dimethoxyphenyl)-tetrahydro-pyrazolo[1,5-a]pyrimidine-3-carboxylic acid ethyl ester

[3-bromo-7-(3,4-dimethoxyphenyl)-2-phenyltetrahydropyrazolo[1,5-a]pyrimidin-5-yl]-phenylmethanone 5-benzoyl-7-(3,4-dimethoxyphenyl)-2-methylsulfanyl-tetrahydropyrazolo[1,5-a]pyrimidine-3-carbonitrile 5-benzoyl-7-(3,4-dimethoxyphenyl)tetrahydropyrazolo-[1,5-a]pyrimidine-3-carbonitrile 5-benzoyl-7-(4-methoxyphenyl)-tetrahydropyrazolo-[1,5-a]pyrimidine-3-carboxylic acid ethyl ester 5-benzoyl-7-(4-methoxyphenyl)-2-methylsulfanyl-tetrahydropyrazolo[1,5-a]pyrimidine-3-carbonitrile 5-benzoyl-7-(4-methoxyphenyl)tetrahydropyrazolo-[1,5-a]pyrimidine-3-carbonitrile 5-benzoyl-7-(3-fluorophenyl)-tetrahydropyrazolo-[1,5-a]pyrimidine-3-carboxylic acid ethyl ester

[3-bromo-7-(3-fluorophenyl)-2-phenyltetrahydro-pyrazolo[1,5-a]pyrimidin-5-yl]-phenylmethanone

[3-bromo-7-(3-bromophenyl)-2-phenyltetrahydro-pyrazolo[1,5-a]pyrimidin-5-yl]-phenylmethanone 7-(2,4-dimethylphenyl)-5-(4-phenoxyphenyltetra-hydropyrazolo[1,5-a]pyrimidine-3-carboxylic acid ethyl ester 3-bromo-7-(2,4-dimethylphenyl)-5-(4-phenoxyphenyl)-2-phenyltetrahydropyrazolo[1,5-a]pyrimidine 7-(2,4-dimethylphenyl)-2-methylsulfanyl-5-(4-phenoxyphenyl)-tetrahydropyrazolo[1,5-a]pyrimidine-3-carbonitrile 7-(2,4-dimethylphenyl)-5-(4-phenoxyphenyl)-tetrahydropyrazolo[1,5-a]pyrimidine-3-carbonitrile 7-(3,4-dimethoxyphenyl)-5-(4-phenoxyphenyl)-tetrahydropyrazolo[1,5-a]pyrimidine-3-carboxylic acid ethyl ester 7-(3,4-dimethoxyphenyl)-2-methylsulfanyl-5-(4-phenoxyphenyl)-tetrahydropyrazolo[1,5-a]pyrimidine-3-carbonitrile 3-[3-cyano-7-(4-hydroxyphenyl)-6-methyltetrahydropyrazolo[1,5-a]pyrimidin-5-yl]-2-hydroxybenzoic acid 3-(3-cyano-5,5a,6,10b-tetrahydro-3H-1,4,10c-triaza-cyclopenta[c]fluoren-5-yl)-2-hydroxybenzoic acid;

3-(3-cyano-5,5a,6,10b-tetrahydro-4H-1,4,10c-triaza-cyclopenta[c]fluoren-5-yl)-2-hydroxybenzoic acid 3-(3-cyano-7-phenylsulfanyltetrahydropyrazolo[1,5-a]pyrimidin-5-yl]-2-hydroxybenzoic acid 3-[2-tert.-butyl-7-(4-chlorophenyl)-7-methyltetra-hydropyrazolo[1,5-a]pyrimidin-5-yl]-2-hydroxybenzoic acid 5-(4-hydroxy-3-methoxyphenyl)-7-(4-hydroxyphenyl)-6-methyltetrahydropyrazolo[1,5-a]pyrimidine-3-carboxylic acid ethyl ester 5-(4-hydroxy-3-methoxyphenyl)-7-(4-hydroxyphenyl)-6-methyltetrahydropyrazolo[1,5-a]pyrimidine-3-carbonitrile 5-(4-hydroxy-3-methoxyphenyl)-5,5a,6,10b-tetrahydro-3H-1,4,10c-triazacyclopenta[c]fluorene-3-carboxylic acid ethyl ester; 5-(4-hydroxy-3-methoxyphenyl)-5,5a,6,10b-tetrahydro-4H-1,4,10c-triazacyclopenta-[c]fluorene-3-carboxylic acid ethyl ester 4-(2-tert.-butyl-5,5a,6,10b-tetrahydro-3H-1,4,10c-triazacyclopenta[c]fluoren-5-yl)-2-methoxyphenol;

4-(2-tert.-butyl-5,5a,6,10b-tetrahydro-4H-1,4,10c-triazacyclopenta[c]fluoren-5-yl)-2-methoxyphenol 5-(4-hydroxy-3-methoxyphenyl)-2-methylsulfanyl-5,5a,6,10b-tetrahydro-3H-1,4,10c-triaza-cyclopenta[c]fluorene-3-carbonitrile; 5-(4-hydroxy-3-methoxyphenyl)-2-methylsulfanyl-5,5a,6,10b-tetrahydro-3H-1,4,10c-triazacyclopenta[c]fluorene-3-carbonitrile 5-(4-hydroxy-3-methoxyphenyl)-7-phenylsulfanyl-tetrahydropyrazolo[1,5-a]pyrimidine-3-carboxylic acid ethyl ester 4-(2-tert.-butyl-7-phenylsulfanyl-tetrahydro-pyrazolo[1,5-a]pyrimidin-5-yl)-2-methoxyphenol 4-(3-bromo-2-phenyl-7-phenylsulfanyl-tetrahydro-pyrazolo[1,5-a]pyrimidin-5-yl)-2-methoxyphenol 5-(2-hydroxy-3-methoxyphenyl)-7-phenylsulfanyl-tetrahydropyrazolo[1,5-a]pyrimidine-3-carboxylic acid ethyl ester 7-(4-chlorophenyl)-5-(2-hydroxy-3-methoxyphenyl)-7-methyltetrahydropyrazolo[1,5-a]pyrimidine-3-carboxylic acid ethyl ester 5-(4-hydroxybutyl)-5,5a,6,10b-tetrahydro-3H-1,4,10c-triazacyclopenta[c]fluorene-3-carbonitrile; 5-(4-hydroxybutyl)-5,5a,6,10b-tetrahydro-4H-1,4,10c-triazacyclopenta[c]fluorene-3-carbonitrile 5-(4-hydroxybutyl)-2-methylsulfanyl-7-phenyl-sulfanyltetrahydropyrazolo[1,5-a]pyrimidine-3-carbonitrile 5-(4-hydroxybutyl)-7-phenylsulfanyltetrahydro-pyrazolo[1,5-a]pyrimidine-3-carbonitrile 7-(4-chlorophenyl)-5-(4-hydroxybutyl)-7-methyltetrahydropyrazolo[1,5-a]pyrimidine-3-carbonitrile 5-butyl-2-methylsulfanyl-5,5a,6,10b-tetrahydro-3H-1,4,10c-triazacyclopenta[c]fluorene-3-carbonitrile; 5-butyl-2-methylsulfanyl-5,5a,6,10b-tetrahydro-4H-1,4,10c-triazacyclopenta[c]fluorene-3-carbonitrile 5-butyl-2-methylsulfanyl-7-phenylsulfanyltetrahydropyrazolo[1,5-a]pyrimidine-3-carbonitrile 5-butyl-7-phenylsulfanyl-tetrahydropyrazolo[1,5-a]pyrimidine-3-carbonitrile 5-butyl-(4-chlorophenyl)-7-methylsulfanyltetrahydropyrazolo[1,5-a]pyrimidine-3-carbonitrile 5-cyclopropyl-7-(2,4-dimethylphenyl)-3-phenylazo-tetrahydropyrazolo[1,5-a]pyrimidin-2-ol 2-tert.-butyl-5-cyclopropyl-7-(2,4-dimethylphenyl)-tetrahydropyrazolo[1,5-a]pyrimidine 5-cyclopropyl-7-(2,4-dimethylphenyl)-2-methyl-sulfanyltetrahydro-pyrazolo[1,5-a]pyrimidine-3-carbonitrile 2-tert.-butyl-5-cyclopropyl-7-(3,4-dimethoxyphenyl)-tetrahydropyrazolo[1,5-a]pyrimidine 3-bromo-5-cyclopropyl-7-(3,4-dimethoxyphenyl)-2-phenyltetrahydropyrazolo[1,5-a]pyrimidine 5-cyclopropyl-7-(4-methoxyphenol)-tetrahydro-pyrazolo[1,5-a]pyrimidine-3-carboxylic acid ethyl ester 5-cyclopropyl-3,5,5a,6,7,11b-hexahydro-1,4,11c-triazacyclopenta[c]phenanthrene-3-carbonitrile 7-(2,4-dimethylphenyl)-5-pyridin-2-yl-tetrahydro-pyrazolo[1,5-a]pyrimidine-3-carboxylic acid ethyl ester 7-(2,4-dimethylphenyl)-3-phenylazo-5-pyridin-2-yl-tetrahydropyrazolo[1,5-a]pyrimidin-2-ol 3-bromo-7-(2,4-dimethylphenyl)-2-phenyl-5-pyridin-2-yl-tetrahydropyrazolo[1,5-a]pyrimidine 7-(2,4-dimethylphenyl)-2-methylsulfanyl-5-pyridin-2-yl-tetrahydropyrazolo[1,5-a]pyrimidine-3-carbonitrile 7-(3,4-dimethoxyphenyl)-2-methylsulfanyl-5-phenethyl-tetrahydropyrazolo[1,5-a]pyrimidine-3-carbonitrile 7-(3,4-dimethoxyphenyl)-5-phenethyl-tetrahydro-pyrazolo[1,5-a]pyrimidine-3-carbonitrile 5-cyclopropyl-7-(2-hydroxyethoxy)-tetrahydropyrazolo[1,5-a]pyrimidine-3-carboxylic acid ethyl ester 2-(2-tert.-butyl-5-cyclopropyltetrahydropyrazolo-[1,5-a]pyrimidin-7-yloxy)-ethanol 5-cyclopropyl-3,5,5a,6,7,8a-hexahydro-8-oxa-1,4,8b-triaza-as-indacene-3-carboxylic acid ethyl ester;

5-cyclopropyl-4,5,5a,6,7,8a-hexahydro-8-oxa-1,4,8b-triaza-as-indacene-3-carboxylic acid ethyl ester 5-cyclopropyl-3-phenylazo-3,5,5a,6,7,8a-hexahydro-8-oxa-1,4,8b-triaza-as-indacen-2-ol; 5-cyclopropyl-3-phenylazo-4,5,5a,6,7,8a-hexahydro-8-oxa-1,4,8b-triaza-as-indacen-2-ol 7-cyclohexyloxy-5-cyclopropyltetrahydropyrazolo-[1,5-a]pyrimidin-3-carboxylic acid ethyl ester 7-cyclohexyloxy-5-cyclopropyl-2-methylsulfanyl-tetrahydropyrazolo[1,5-a]pyrimidin-3-carbonitrile 7-(4-chlorophenyl)-5-cyclohexyltetrahydropyrazolo-[1,5-a]pyrimidin-3-carbonitrile 5-cyclohexyl-7-(2-hydroxyethoxy)-tetrahydropyrazolo-[1,5-a]pyrimidine-3-carboxylic acid ethyl ester 5-cyclohexyl-3,5,5a,6,7,8a-hexahydro-8-oxa-1,4,8b-triaza-as-indacene-3-carboxylic acid ethyl ester; 5-cyclohexyl-4,5,5a,6,7,8a-hexahydro-8-oxa-1,4,8b-triaza-as-indacene-3-carboxylic acid ethyl ester 5-cyclohexyl-7-cyclohexyloxytetrahydropyrazolo[1,5-a]pyrimidine-3-carboxylic acid ethyl ester 7-(2,4-dimethylphenyl)-3-phenylazo-5-propyltetra-hydropyrazolo[1,5-a]pyrimidin-2-ol 7-(2,4-dimethylphenyl)-2-methylsulfanyl-5-propyl-tetrahydropyrazolo[1,5-a]pyrimidine-3-carbonitrile 5-tert.-butyl-7-(2,4-dimethylphenyl)-tetrahydro-pyrazolo[1,5-a]pyrimidine-3-carboxylic acid ethyl ester 2,5-di-tert.-butyl-7-(3,4-dimethoxyphenyl)-tetra-hydropyrazolo[1,5-a]pyrimidine 3-bromo-5-tert.-butyl-7-(3,4-dimethoxyphenyl)-2-phenyltetrahydropyrazolo[1,5-a]pyrimidine 2-[3-cyano-6,7-bis-(4-methoxyphenyl)-tetrahydro-pyrazolo[1,5-a]pyrimidin-5-yl]-cyclopropanecarboxylic acid ethyl ester 3-cyano-6,7-bis-(4-methoxyphenyl)-tetrahydro-pyrazolo[1,5-a]pyrimidine-5-carboxylic acid 4-[3-bromo-6-methyl-2-phenyl-5-(4-trifluoromethyl-phenyl)-tetrahydropyrazolo[1,5-a]pyrimidin-7-yl]-phenol 7-(4-hydroxyphenyl)-6-methyl-2-methylsulfanyl-5-(4-trifluoro-methylphenyl)-tetrahydropyrazolo[1,5-a]-pyrimidine-3-carbonitrile 7-(4-hydroxyphenyl)-6-methyl-5-(4-trifluoromethyl-phenyl)-tetrahydropyrazolo[1,5-a]pyrimidine-3-carbonitrile 2-(4-nitrophenylsulfonyl)-5-phenylsulfanyl-7-pyridin-2-yl-6,7-dihydro-5H-thiazolo[3,2-a]-pyrimidine 3-(4-chlorophenyl)-5-phenylsulfanyl-7-pyridin-2-yl-6,7-dihydro-5H-thiazolo[3,2-a]pyrimidine 5-phenylsulfanyl-7-pyridin-2-yl-3-p-tolyl-6,7-dihydro-5H-thiazolo[3,2-a]pyrimidine 7-methoxy-4-phenylsulfanyl-2-pyridin-2-yl-3,4-dihydro-2H-9-thia-1,4a-diazafluorene 7-ethoxy-4-phenylsulfanyl-2-pyridin-2-yl-3,4-dihydro-2H-9-thia-1,4a-diazafluorene 7-fluoro-4-phenylsulfanyl-2-pyridin-2-yl-3,4-dihydro-2H-9-thia-1,4a-diazafluorene 3-naphthalin-2-yl-5-phenylsulfanyl-7-pyridin-2-yl-6,7-dihydro-5H-thiazolo[3,2-a]pyrimidine 7-phenyl-3-phenylazo-5-pyridin-2-yl-3,5,6,7-tetrahydro-pyrazolo[1,5-a]pyrimidin-2-ol 7-phenylsulfanyl-5-pyridin-2-yl-3,5,6,7-tetrahydro-pyrazolo[1,5-a]pyrimidine-3-carboxylic acid ethyl ester 3-phenylazo-7-phenylsulfanyl-5-pyridin-2-yl-3,5,6,7-tetrahydropyrazolo[1,5-a]pyrimidin-2-ol 3-bromo-7-phenylsulfanyl-5-pyridin-2-yl-3,5,6,7-tetrahydropyrazolo[1,5-a]pyrimidine 7-phenylsulfanyl-5-pyridin-2-yl-3,5,6,7-tetrahydro-pyrazolo[1,5-a]pyrimidine-3-carbonitrile 7-(3,4-dimethoxyphenyl)-2-methylsulfanyl-5-pyridin-2-yl-tetrahydropyrazolo[1,5-a]pyrimidine-3-carbonitrile 3-bromo-7-(3,4-dimethoxyphenyl)-2-phenyl-5-pyridin-2-yl-tetrahydropyrazolo[1,5-a]pyrimidine 3-bromo-7-(3,4-dimethoxyphenyl)-2-phenyl-tetrahydropyrazolo[1,5-a]pyrimidine-5-carboxylic acid ethyl ester 3-bromo-7-(3,4-dimethoxyphenyl)-5-(5-nitrofuran-2-yl)-2-phenyl-tetrahydropyrazolo[1,5-a]pyrimidine 3-cyano-7-(3,4-dimethoxyphenyl)-2-methylsulfanyl-tetrahydropyrazolo[1,5-a]pyrimidine-5-carboxylic acid ethyl ester 3-cyano-7-(3,4-dimethoxyphenyl)-tetrahydropyrazolo-[1,5-a]pyrimidine-5-carboxylic acid ethyl ester 3-bromo-7-(3,4-dimethoxyphenyl)-2-phenyl-5-pyridin-2-yl-4,5,6,7-tetrahydropyrazolo[1,5-a]pyrimidine 7-(3,4-dimethoxyphenyl)-5-pyridin-2-yl-4,5,6,7-tetrahydropyrazolo[1,5-a]pyrimidine-3-carbonitrile 7-(3,4-dimethoxyphenyl)-2-methylsulfanyl-5-(5-nitro-furan-2-yl)-tetrahydropyrazolo[1,5-a]pyrimidine-3-carbonitrile, and 7-(3,4-dimethoxyphenyl)-5-pyridin-2-yl-4,5,6,7-tetrahydropyrazolo[1,5-a]pyrimidine-3-carboxylic acid ethyl ester.

9. A pharmaceutical formulation comprising at least one compound corresponding to structure (I A), (I B) or (II)

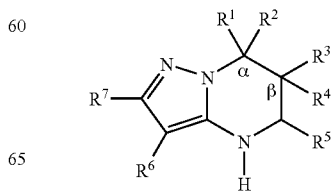

IA

-continued

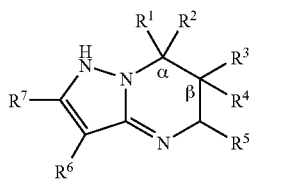

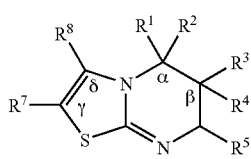

or a salt thereof, or a stereoisomer, mixture of stereoisomers having an arbitrary mixture ratio, or a racemate thereof; wherein $R^1$ and $R^2$ are independently selected from the group consisting of H, O—$R^9$, S—$R^{10}$, $C_{1-12}$-alkyl, $C_{3-8}$-cycloalkyl, —$CH_2$—$C_{3-8}$-cycloalkyl, aryl, —($C_{1-6}$-alkyl)-aryl, heterocyclyl or —($C_{1-6}$ alkyl)-heterocyclyl, wherein exactly one of the radicals $R^1$ and $R^2$ is H, or wherein one of the radicals $R^1$ and $R^2$ is aryl and the other radical of $R^1$ and $R^2$ is H or $C_{1-12}$-alkyl, $R^3$ and $R^4$ are selected from the group consisting of H, $C_{1-12}$-alkyl, $C_{3-8}$-cycloalkyl, —$CH_2$—$C_{3-8}$-cycloalkyl, aryl or —($C_{1-6}$-alkyl)-aryl, wherein at least one of the radicals $R^3$ and $R^4$ is H, or one of the radicals $R^1$ and $R^2$ together with one of the radicals $R^3$ and $R^4$ form W, where W is $\alpha'$-$(CH_2)_n$-$\beta'$ where n=3, 4, 5 or 6, $\alpha'$-CH=CH—$CH_2$-$\beta'$, $\alpha'$-$CH_2$—CH=CH-$\beta'$, $\alpha'$-CH=CH—$CH_2$—$CH_2$-$\beta'$, $\alpha'$-$CH_2$—CH=CH—$CH_2$-$\beta'$, $\alpha'$-$CH_2$—$CH_2$—CH=CH-$\beta'$, or $\alpha'$-O—$(CH_2)_m$-$\beta'$ where m=2, 3, 4 or 5, or where W corresponds to

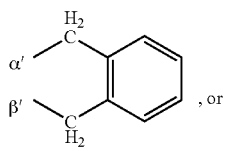

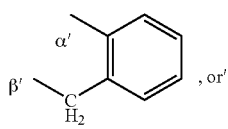

where X = $CH_2$, O, or S, or

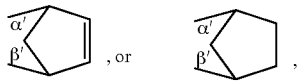

where the end of W identified by $\alpha'$ is joined to the atom identified by $\alpha$ in the compound corresponding to structure (I A), (I B) or (II), the end of W identified by $\beta'$ is joined to the atom identified by $\beta$ in the compound corresponding to structure (I A), (I B) or (II), the other radical of $R^1$ and $R^2$ is H or $C_{1-12}$-alkyl, and the other radical of $R^3$ and $R^4$ is H or $C_{1-12}$-alkyl;

$R^5$ is $C_{1-12}$-alkyl, $C_{3-8}$-cycloalkyl, —$CH_2$—$C_{3-8}$-cycloalkyl, aryl, —($C_{1-6}$ alkyl)-aryl, heterocyclyl, —($C_{1-6}$ alkyl)-heterocyclyl or C(=O)$R^{11}$;

$R^6$ is H, $C_{1-8}$-alkyl, —CN, fluorine, chlorine, bromine, iodine, $NO_2$, $NH_2$, $NHR^{12}$, $NR^{13}R^{14}$, $OR^{15}$, $S(O)_pR^{16}$ where p=0, 1 or 2, —C(=O)$R^{17}$ or —N=N-aryl;

$R^7$ is H, $C_{1-8}$-alkyl, aryl, —CN, fluorine, chlorine, bromine, iodine, $NO_2$, $NH_2$, $NHR^{12}$, $NR^{13}R^{14}$, $OR^{18}$, $S(O)^qR^{19}$ where q=0, 1 or 2, or C(=O)$R^{20}$, $R^8$ is H, $C_{1-8}$-alkyl or aryl, or $R^7$ and $R^8$ together form Y, wherein Y is $\gamma'$-$CR^{21}$=$CR^{22}$—$CR^{23}$=$CR^{24}$-$\delta'$, where the end of Y identified by $\gamma'$ is joined to the atom identified by $\gamma$ in the compound corresponding to structure (II), and where the end of Y identified by $\delta'$ is joined to the atom identified by $\delta$ in the compound corresponding to structure (II);

$R^9$ and $R^{10}$ are independently selected from the group consisting of H, $C_{1-8}$-alkyl, $C_{3-8}$-cycloalkyl, —$CH_2$—$C_{3-8}$-cycloalkyl, aryl and —($C_{1-6}$-alkyl)-aryl;

$R^{11}$ is H, $C_{1-8}$-alkyl, $C_{3-8}$-cycloalkyl, —$CH_2$—$C_{3-8}$-cycloalkyl, aryl or $OR^{25}$;

$R^{12}$ is $C_{1-6}$-alkyl or —$CH_2$-aryl;

$R^{13}$ and $R^{14}$ are identical or different $C_{1-6}$-alkyl radicals, or together are —$(CH_2)_h$— and form a ring, where h=4 or 5;

$R^{15}$ and $R^{16}$ are independently selected from the group consisting of H, $C_{1-8}$-alkyl, $C_{3-8}$-cycloalkyl, —$CH_2$—$C_{3-8}$-cycloalkyl, aryl and —($C_{1-6}$-alkyl)-aryl;

$R^{17}$ is H, $C_{1-8}$-alkyl, $C_{3-8}$-cycloalkyl, —$CH_2$—$C_{3-8}$-cycloalkyl, aryl, —($C_{1-6}$-alkyl)-aryl, $NH_2$, $NHR^{12}$, $NR^{13}R^{14}$ or $OR^{26}$;

$R^{18}$ and $R^{19}$ are independently selected from the group consisting of H, $C_{1-8}$-alkyl, $C_{3-8}$-cycloalkyl, —$CH_2$—$C_{3-8}$-cycloalkyl, aryl or —($C_{1-6}$-alkyl)-aryl;

$R^{20}$ is H, $C_{1-8}$-alkyl, $C_{3-8}$-cycloalkyl, —$CH_2$—$C_{3-8}$-cycloalkyl, aryl or —($C_{1-6}$-alkyl)-aryl or $OR^{27}$;

$R^{21}$, $R^{22}$, $R^{23}$ and $R^{24}$ are independently selected from the group consisting of H, fluorine, chlorine, bromine, iodine and $OR^{28}$;

$R^{25}$, $R^{26}$, $R^{27}$ and $R^{28}$ are independently selected from the group consisting of H or $C_{1-6}$-alkyl, where $R^{25}$ is not H when both $R^1$ is aryl and $R^2$ is alkyl;

and a pharmaceutically acceptable carrier.

10. A medicament according to claim 9, wherein the compound corresponding to structure (I A), (I B) or (II) is present as a physiologically compatible salt.

11. A pharmaceutical formulation according to claim 9, wherein the compound corresponding to structure (I A), (I B) or (II) is present as a pure enantiomer or a pure diastereomer.

12. A pharmaceutical formulation according to claim 9, wherein the compound corresponding to structure (I A), (I B) or (II) is present as a mixture of enantiomers or a mixture of stereoisomers.

13. A pharmaceutical composition comprising at least one compound corresponding to structure (I A), (I B) or (II) of claim 1.

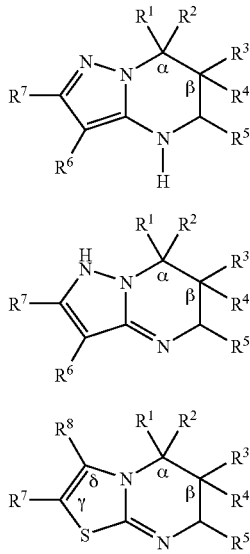

or a salt thereof, or a stereoisomer, mixture of stereoisomers having an arbitrary mixture ratio, or a racemate thereof;
wherein $R^1$, $R^2$, $R^3$, $R^4$, $R^5$, $R^6$, $R^7$ and $R^8$ are as defined in claim 1;
and at least one pharmaceutical auxiliary substance.

14. A method for treating pain comprising administering a pharmaceutically effective amount of a compound corresponding to structure (I A), (I B) or (II)

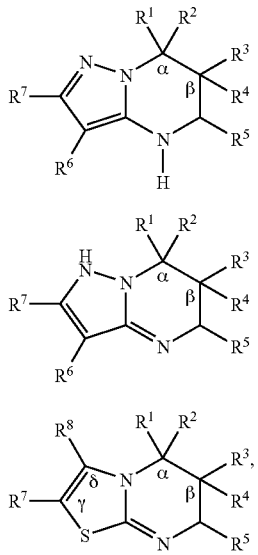

or a or salt thereof, or a stereoisomer, mixture of stereoisomers having an arbitrary mixture ratio, or a racemate thereof;
wherein
$R^1$ and $R^2$ are independently selected from the group consisting of H, O—$R^9$, S—$R^{10}$, $C_{1-12}$-alkyl, $C_{3-8}$-cycloalkyl, —$CH_2$—$C_{3-8}$-cycloalkyl, aryl, —($C_{1-6}$-alkyl)-aryl, heterocyclyl or —($C_{1-6}$ alkyl)-heterocyclyl, wherein exactly one of the radicals $R^1$ and $R^2$ is H, or wherein one of the radicals $R^1$ and $R^2$ is aryl and the other radical of $R^1$ and $R^2$ is H or $C_{1-12}$-alkyl, $R^3$ and $R^4$ are selected from the group consisting of H, $C_{1-12}$-alkyl, $C_{3-8}$-cycloalkyl, —$CH_2$—$C_{3-8}$-cycloalkyl, aryl or —($C_{1-6}$-alkyl)-aryl, wherein at least one of the radicals $R^3$ and $R^4$ is H, or one of the radicals $R^1$ and $R^2$ together with one of the radicals $R^3$ and $R^4$ form W, where W is α'-$(CH_2)_n$-β' where n=3, 4, 5 or 6, α'-CH=CH—$CH_2$-β', α'-$CH_2$—CH=CH-β', α'-CH=CH—$CH_2$—$CH_2$-β', α'-$CH_2$—CH=CH—$CH_2$-β', α'-$CH_2$—$CH_2$—CH=CH-β', or α'-O—$(CH_2)_m$-β' where m=2, 3, 4 or 5, or where W corresponds to

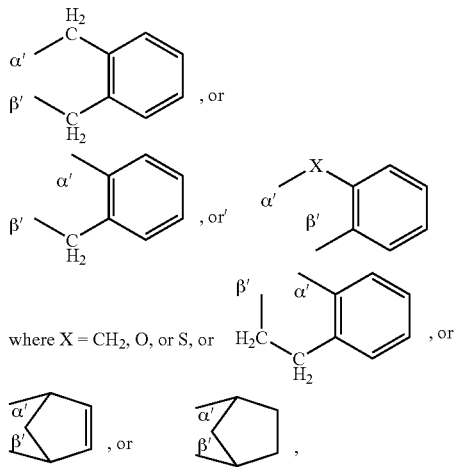

where X = $CH_2$, O, or S, or where the end of W identified by α' is joined to the atom identified by α in the compound corresponding to structure (I A), (I B) or (II), the end of W identified by β' is joined to the atom identified by β in the compound corresponding to structure (I A), (I B) or (II), the other radical of $R^1$ and $R^2$ is H or $C_{1-12}$-alkyl, and the other radical of $R^3$ and $R^4$ is H or $C_{1-12}$-alkyl;

$R^5$ is $C_{1-12}$-alkyl, $C_{3-8}$-cycloalkyl, —$CH_2$—$C_{3-8}$-cycloalkyl, aryl, —($C_{1-6}$ alkyl)-aryl, heterocyclyl, —($C_{1-6}$ alkyl)-heterocyclyl or C(=O)$R^{11}$;

$R^6$ is H, $C_{1-8}$-alkyl, —CN, fluorine, chlorine, bromine, iodine, $NO_2$, $NH_2$, $NHR^{12}$, $NR^{13}R^{14}$, $OR^{15}$, $S(O)_pR^{16}$ where p=0, 1 or 2, —C(=O)$R^{17}$ or —N=N-aryl;

$R^7$ is H, $C_{1-8}$-alkyl, aryl, —CN, fluorine, chlorine, bromine, iodine, $NO_2$, $NH_2$, $NHR^{12}$, $NR^{13}R^{14}$, $OR^{18}$, $S(O)_qR^{19}$ where q=0, 1 or 2, or C(=O)$R^{20}$, $R^8$ is H, $C_{1-8}$-alkyl or aryl, or $R^7$ and $R^8$ together form Y, wherein Y is γ'-$CR^{21}$=$CR^{22}$—$CR^{23}$=$CR^{24}$-δ', where the end of Y identified by γ' is joined to the atom identified by γ in the compound corresponding to structure (II), and where the end of Y identified by δ' is joined to the atom identified by δ in the compound corresponding to structure (II);

$R^9$ and $R^{10}$ are independently selected from the group consisting of H, $C_{1-8}$-alkyl, $C_{3-8}$-cycloalkyl, —$CH_2$—$C_{3-8}$-cycloalkyl, aryl and —($C_{1-6}$-alkyl)-aryl;

$R^{11}$ is H, $C_{1-8}$-alkyl, $C_{3-8}$-cycloalkyl, —$CH_2$—$C_{3-8}$-cycloalkyl, aryl or $OR^{25}$;

$R^{12}$ is $C_{1-6}$-alkyl or —$CH_2$-aryl;

$R^{13}$ and $R^{14}$ are identical or different $C_{1-6}$-alkyl radicals, or together are —$(CH_2)_h$— and form a ring, where h=4 or 5;

$R^{15}$ and $R^{16}$ are independently selected from the group consisting of H, $C_{1-8}$-alkyl, $C_{3-8}$-cycloalkyl, —$CH_2$—$C_{3-8}$-cycloalkyl, aryl or —($C_{1-6}$-alkyl)-aryl;

$R^{17}$ is H, $C_{1-8}$-alkyl, $C_{3-8}$-cycloalkyl, —$CH_2$—$C_{3-8}$-cycloalkyl, aryl, —($C_{1-6}$-alkyl)-aryl, $NH_2$, $NHR^{12}$, $NR^{13}R^{14}$ or $OR^{26}$;

$R^{18}$ and $R^{19}$ are independently selected from the group consisting of H, $C_{1-8}$-alkyl, $C_{3-8}$-cycloalkyl, —$CH_2$—$C_{3-8}$-cycloalkyl, aryl and —($C_{1-6}$-alkyl)-aryl;

$R^{20}$ is H, $C_{1-8}$-alkyl, $C_{3-8}$-cycloalkyl, —$CH_2$—$C_{3-8}$-cycloalkyl, aryl or —($C_{1-6}$-alkyl)-aryl or $OR^{27}$;

$R^{21}$, $R^{22}$, $R^{23}$ and $R^{24}$ are independently selected from the group consisting of H, fluorine, chlorine, bromine, iodine and $OR^{28}$;

$R^{25}$, $R^{26}$, $R^{27}$ and $R^{28}$ are independently selected from the group consisting of H or $C_{1-6}$-alkyl, where $R^{25}$ is not H when both $R^1$ is aryl and $R^2$ is alkyl.

15. A method according to claim 14, wherein the compound corresponding to structure (I A), (I B) or (II) is present as a physiologically compatible salt.

16. A method according to claim 14, wherein the compound corresponding to structure (I A), (I B) or (II) is present as a pure enantiomer or a pure diastereomer.

17. A method according to claim 14, wherein the compound corresponding to structure (I A), (I B) or (II) is present as a mixture of enantiomers or a mixture of stereoisomers.

18. A method for treatment of Alzheimer's disease, comprising administering a pharmaceutically effective amount of a compound corresponding to structure (I A), (I B) or (II),

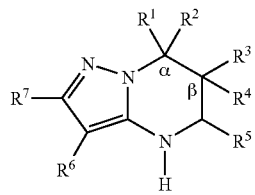

IA

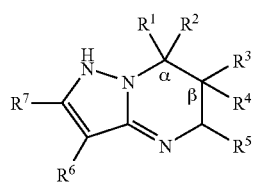

IB

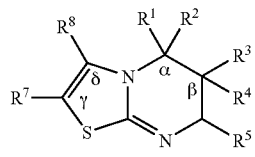

II or a salt thereof, or a stereoisomer, mixture of stereoisomers having an arbitrary mixture ratio, or a racemate thereof; wherein $R^1$, $R^2$, $R^3$, $R^4$, $R^5$, $R^6$, $R^7$ and $R^8$ are as defined in claim 9.

19. A method according to claim 18, wherein the compound corresponding to structure (I A), (I B) or (II) is present as a physiologically compatible salt.

20. A method according to claim 18, wherein the compound corresponding to structure (I A), (I B) or (II) is present as a pure enantiomer or a pure diastereomer.

21. A method according to claim 18, wherein the compound corresponding to structure (I A), (I B) or (II) is present as a mixture of enantiomers or a mixture of stereoisomers.

22. A method of ligand-binding a nucleoside transport protein, adenosine kinase, adenosine deaminase, or $A_1$, $A_2$, or $A_3$ receptors comprising providing a compound corresponding to formula (I A) or (I B)

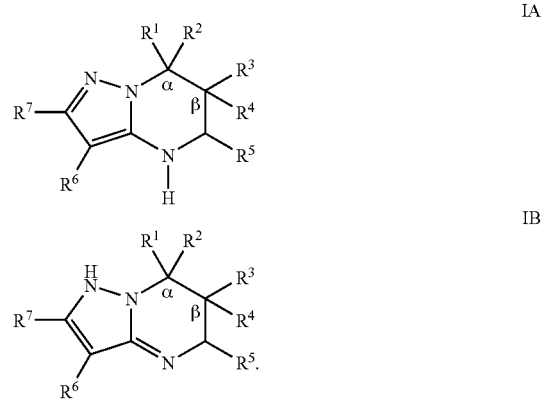

or a salt thereof, or a stereoisomer, mixture of stereoisomers having an arbitrary mixture ratio, or a racemate thereof; wherein $R^1$ and $R^2$ are independently selected from the group consisting of H, O—$R^9$, S—$R^{10}$, $C_{1-12}$-alkyl, $C_{3-8}$-cycloalkyl, —$CH_2$—$C_{3-8}$-cycloalkyl, aryl, —($C_{1-6}$-alkyl)-aryl, heterocyclyl or —($C_{1-6}$ alkyl)-heterocyclyl, wherein exactly one of the radicals $R^1$ and $R^2$ is H, or wherein one of the radicals $R^1$ and $R^2$ is aryl and the other radical of $R^1$ and $R^2$ is H or $C_{1-12}$-alkyl, $R^3$ and $R^4$ are selected from the group consisting of H, $C_{1-12}$-alkyl, $C_{3-8}$-cycloalkyl, —$CH_2$—$C_{3-8}$-cycloalkyl, aryl or —($C_{1-6}$-alkyl)-aryl, wherein at least one of the radicals $R^3$ and $R^4$ is H, or one of the radicals $R^1$ and $R^2$ together with one of the radicals $R^3$ and $R^4$ form W, where W is $\alpha'$-$(CH_2)_n$-$\beta'$ where n=3, 4, 5 or 6, $\alpha'$-CH=CH—$CH_2$-$\beta'$, $\alpha'$-$CH_2$—CH=CH-$\beta'$, $\alpha'$-CH=CH—$CH_2$—$CH_2$-$\beta'$, $\alpha'$-$CH_2$—CH=CH—$CH_2$-$\beta'$, $\alpha'$-$CH_2$—$CH_2$—CH=CH-$\beta'$, or $\alpha'$-O—$(CH_2)_m$-$\beta'$ where m=2, 3, 4 or 5, or where W corresponds to

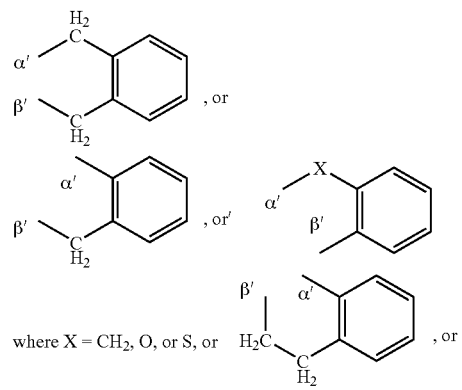

where X = $CH_2$, O, or S, or

-continued

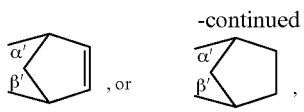, or where the end of W identified by α' is joined to the atom identified by α in the compound corresponding to structure (I A) or (I B), the end of W identified by β' is joined to the atom identified by β in the compound corresponding to structure (I A) or (I B), the other radical of $R^1$ and $R^2$ is H or $C_{1-12}$-alkyl, and the other radical of $R^3$ and $R^4$ is H or $C_{1-12}$-alkyl;

$R^5$ is $C_{1-12}$-alkyl, $C_{3-8}$-cycloalkyl, —$CH_2$—$C_{3-8}$-cycloalkyl, aryl, —($C_{1-6}$ alkyl)-aryl, heterocyclyl, —($C_{1-6}$ alkyl)-heterocyclyl or $C(=O)R^{11}$;

$R^6$ is H, $C_{1-8}$-alkyl, —CN, fluorine, chlorine, bromine, iodine, $NO_2$, $NH_2$, $NHR^{12}$, $NR^{13}R^{14}$, $OR^{15}$, $S(O)_pR^{16}$ where p=0, 1 or 2, —$C(=O)R^{17}$ or —N=N-aryl;

$R^7$ is H, $C_{1-8}$-alkyl, aryl, —CN, fluorine, chlorine, bromine, iodine, $NO_2$, $NH_2$, $NHR^{12}$, $NR^{13}R^{14}$, $OR^{18}$, $S(O)^qR^{19}$ where q=0, 1 or 2, or $C(=O)R^{20}$, $R^9$ and $R^{10}$ are independently selected from the group consisting of H, $C_{1-8}$-alkyl, $C_{3-8}$-cycloalkyl, —$CH_2$—$C_{3-8}$-cycloalkyl, aryl and —($C_{1-6}$-alkyl)-aryl;

$R^{11}$ is H, $C_{1-8}$-alkyl, $C_{3-8}$-cycloalkyl, —$CH_2$—$C_{3-8}$-cycloalkyl, aryl or $OR^{25}$;

$R^{12}$ is $C_{1-6}$-alkyl or —$CH_2$-aryl;

$R^{13}$ and $R^{14}$ are identical or different $C_{1-6}$-alkyl radicals, or together are —$(CH_2)_h$— and form a ring, where h=4 or 5;

$R^{15}$ and $R^{16}$ are independently selected from the group consisting of H, $C_{1-8}$-alkyl, $C_{3-8}$-cycloalkyl, —$CH_2$—$C_{3-8}$-cycloalkyl, aryl or —($C_{1-6}$-alkyl)-aryl;

$R^{17}$ is H, $C_{1-8}$-alkyl, $C_{3-8}$-cycloalkyl, —$CH_2$—$C_{3-8}$-cycloalkyl, aryl, —($C_{1-6}$-alkyl)-aryl, $NH_2$, $NHR^{12}$, $NR^{13}R^{14}$ or $OR^{26}$;

$R^{18}$ and $R^{19}$ are independently selected from the group consisting of H, $C_{1-8}$-alkyl, $C_{3-8}$-cycloalkyl, —$CH_2$—$C_{3-8}$-cycloalkyl, aryl and —($C_{1-6}$-alkyl)-aryl;

$R^{20}$ is H, $C_{1-8}$-alkyl, $C_{3-8}$-cycloalkyl, —$CH_2$—$C_{3-8}$-cycloalkyl, aryl or —($C_{1-6}$-alkyl)-aryl or $OR^{27}$;

$R^{25}$, $R^{26}$ and $R^{27}$ are independently selected from the group consisting of H or $C_{1-6}$-alkyl, where $R^{25}$ is not H when both $R^1$ is aryl and $R^2$ is alkyl;

in the presence of a nucleoside transport protein, adenosine kinase, adenosine deaminase, or $A_1$, $A_2$, or $A_3$ receptors.

23. A method according to claim 22, wherein the compound corresponding to structure (I A) or (I B) is present as a physiologically compatible salt.

24. A method according to claim 22, wherein the compound corresponding to structure (I A) or (I B) is present as a pure enantiomer or a pure diastereomer.

25. A method according to claim 22, wherein the compound corresponding to structure (I A) or (I B) is present as a mixture of enantiomers or a mixture of stereoisomers.

26. A method for treating pain comprising administering a pharmacuetically effective amount of a pharmaceutical formulation according to claim 9.

27. A process for the preparation of compounds corresponding to structure (I A) or (I B) as well as their pharmaceutically acceptable salts

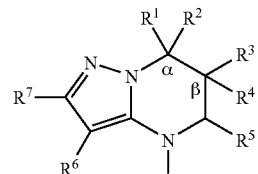

IA

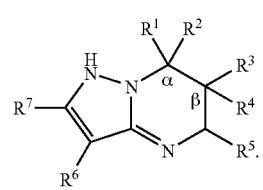

IB $R^1$ and $R^2$ are independently selected from the group consisting of H, O—$R^9$, S—$R^{10}$, $C_{1-12}$-alkyl, $C_{3-8}$-cycloalkyl, —$CH_2$—$C_{3-8}$-cycloalkyl, aryl, —($C_{1-6}$-alkyl)-aryl, heterocyclyl or —($C_{1-6}$ alkyl)-heterocyclyl, wherein exactly one of the radicals $R^1$ and $R^2$ is H, or wherein one of the radicals $R^1$ and $R^2$ is aryl and the other radical of $R^1$ and $R^2$ is H or $C_{1-12}$-alkyl, $R^3$ and $R^4$ are selected from the group consisting of H, $C_{1-12}$-alkyl, $C_{3-8}$-cycloalkyl, —$CH_2$—$C_{3-8}$-cycloalkyl, aryl or —($C_{1-6}$-alkyl)-aryl, wherein at least one of the radicals $R^3$ and $R^4$ is H, or one of the radicals $R^1$ and $R^2$ together with one of the radicals $R^3$ and $R^4$ form W, where W is α'-$(CH_2)_n$-β' where n=3, 4, 5 or 6, α'-CH=CH—$CH_2$-β', α'-$CH_2$—CH=CH-β', α'-CH=CH—$CH_2$—$CH_2$-β', α'-$CH_2$—CH=CH—$CH_2$-β', α'-$CH_2$—$CH_2$—CH=CH-β', or α'-O—$(CH_2)_m$-β' where m=2, 3, 4 or 5, or where W corresponds to

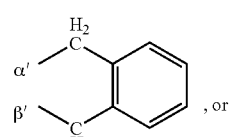, or

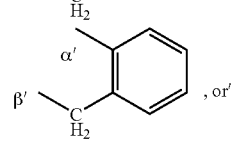, or where X = $CH_2$, O, or S, or 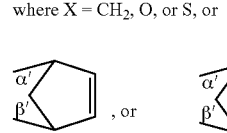, or

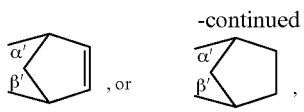, or where the end of W identified by α' is joined to the atom identified by α in the compound corresponding to structure (I A) or (I B), the end of W identified by β' is joined to the atom identified by β in the compound corresponding to structure (I A) or (I B), the other radical of $R^1$ and $R^2$ is H or $C_{1-12}$-alkyl, and the other radical of $R^3$ and $R^4$ is H or $C_{1-12}$-alkyl;

$R^5$ is $C_{1-12}$-alkyl, $C_{3-8}$-cycloalkyl, —$CH_2$—$C_{3-8}$-cycloalkyl, aryl, —($C_{1-6}$ alkyl)-aryl, heterocyclyl, —($C_{1-6}$ alkyl)-heterocyclyl or $C(=O)R^{11}$;

$R^6$ is H, $C_{1-8}$-alkyl, —CN, fluorine, chlorine, bromine, iodine, $NO_2$, $NH_2$, $NHR^{12}$, $NR^{13}R^{14}$, $OR^{15}$, $S(O)_pR^{16}$ where p=0, 1 or 2, —$C(=O)R^{17}$ or —N=N-aryl;

$R^7$ is H, $C_{1-8}$-alkyl, aryl, —CN, fluorine, chlorine, bromine, iodine, $NO_2$, $NH_2$, $NHR^{12}$, $NR^{13}R^{14}$, $OR^{18}$, $S(O)^qR^{19}$ where q=0, 1 or 2, or $C(=O)R^{20}$, $R^9$ and $R^{10}$ are independently selected from the group consisting of H, $C_{1-8}$-alkyl, $C_{3-8}$-cycloalkyl, —$CH_2$—$C_{3-8}$-cycloalkyl, aryl and —($C_{1-6}$-alkyl)-aryl;

$R^{11}$ is H, $C_{1-8}$-alkyl, $C_{3-8}$-cycloalkyl, —$CH_2$—$C_{3-8}$-cycloalkyl, aryl or $OR^{25}$;

$R^{12}$ is $C_{1-6}$-alkyl or —$CH_2$-aryl;

$R^{13}$ and $R^{14}$ are identical or different $C_{1-6}$-alkyl radicals, or together are —$(CH_2)_h$— and form a ring, where h=4 or 5;

$R^{15}$ and $R^{16}$ are independently selected from the group consisting of H, $C_{1-8}$-alkyl, $C_{3-8}$-cycloalkyl, —$CH_2$—$C_{3-8}$-cycloalkyl, aryl or —($C_{1-6}$-alkyl)-aryl;

$R^{17}$ is H, $C_{1-8}$-alkyl, $C_{3-8}$-cycloalkyl, —$CH_2$—$C_{3-8}$-cycloalkyl, aryl, —($C_{1-6}$-alkyl)-aryl, $NH_2$, $NHR^{12}$, $NR^{13}R^{14}$ or $OR^{26}$;

$R^{18}$ and $R^{19}$ are independently selected from the group consisting of H, $C_{1-8}$-alkyl, $C_{3-8}$-cycloalkyl, —$CH_2$—$C_{3-8}$-cycloalkyl, aryl or —($C_{1-6}$-alkyl)-aryl;

$R^{20}$ is H, $C_{1-8}$-alkyl, $C_{3-8}$-cycloalkyl, —$CH_2$—$C_{3-8}$-cycloalkyl, aryl or —($C_{1-6}$-alkyl)-aryl or $OR^{27}$; and $R^{25}$, $R^{26}$, and $R^{27}$ are independently selected from the group consisting of H and $C_{1-6}$-alkyl, where $R^{25}$ is not H when both $R^1$ is aryl and $R^2$ is alkyl; comprising reacting a pyrazolamine corresponding to structure (IIIA) or (IIIB),

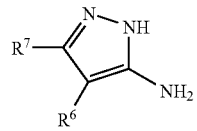

IIIA

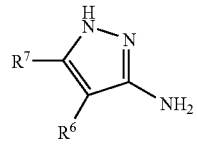

IIIB wherein $R^6$ and $R^7$ are as defined above in this claim, in the presence of an acid, with an aldehyde corresponding to structure (IV)

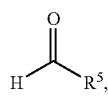

IV wherein $R^5$ is as defined above in this claim, and with an olefin corresponding to structure (V)

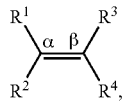

V wherein $R^1$, $R^2$, $R^3$ and $R^4$ are as defined above in this claim, with the proviso that if one of the radicals $R^1$ and $R^2$ together with one of the radicals $R^3$ and $R^4$ forms W, the end of W identified by α' is joined to the α-carbon atom of the olefin of the general structure (V), and the end of W identified by β' is joined to the β-carbon atom of the olefin of the general structure (V).

28. A process according to claim 27, wherein the reaction of the heterocyclylamine corresponding to structure (III A) or (III B) with the aldehyde corresponding to structure (IV) and with the olefin corresponding to structure (V) is carried out in a one-pot process.

29. A process according to claim 27, wherein the acid is trifluoroacetic acid.

30. A process according to of claim 27, wherein the reaction is carried out in an organic solvent at a temperature of 0° to 100° C. and at a reaction time of 0.25 to 12 hours.

31. A process according to claim 27, wherein the reaction is carried out at a temperature of 15° to 40° C.

32. A process for the preparation of compounds corresponding to structure (II) or pharmaceutically acceptable salts thereof

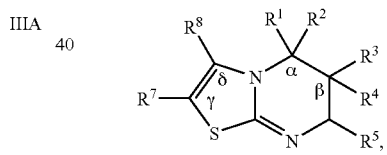

II wherein $R^1$ and $R^2$ are independently selected from the group consisting of H, O—$R^9$, S—$R^{10}$, $C_{1-12}$-alkyl, $C_{3-8}$-cycloalkyl, —$CH_2$—$C_{3-8}$-cycloalkyl, aryl, —($C_{1-6}$-alkyl)-aryl, heterocyclyl or —($C_{1-6}$ alkyl)-heterocyclyl, wherein exactly one of the radicals $R^1$ and $R^2$ is H, or wherein one of the radicals $R^1$ and $R^2$ is aryl and the other radical of $R^1$ and $R^2$ is H or $C_{1-12}$-alkyl, $R^3$ and $R^4$ are selected from the group consisting of H, $C_{1-12}$-alkyl, $C_{3-8}$-cycloalkyl, —$CH_2$—$C_{3-8}$-cycloalkyl, aryl or —($C_{1-6}$-alkyl)-aryl, wherein at least one of the radicals $R^3$ and $R^4$ is H, or one of the radicals $R^1$ and $R^2$ together with one of the radicals $R^3$ and $R^4$ form W, where W is α'-$(CH_2)_n$-β' where n=3, 4, 5 or 6, α'-CH=CH—$CH_2$-β', α'-$CH_2$—CH=CH-β', α'-CH=CH—$CH_2$—$CH_2$-β', α'-$CH_2$—CH=CH—$CH_2$-β', α'-$CH_2$—$CH_2$—CH=CH-β', or α'-O—$(CH_2)_m$-β' where m=2, 3, 4 or 5, or where W corresponds to

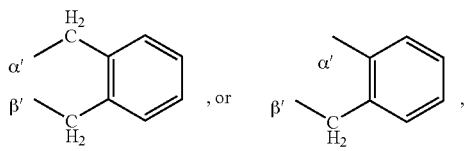
, or

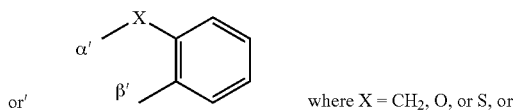
or where X = CH₂, O, or S, or

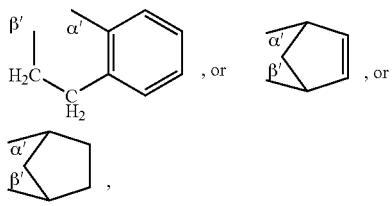
, or where the end of W identified by α' is joined to the atom identified by α in the compound corresponding to structure (II), the end of W identified by β' is joined to the atom identified by β in the compound corresponding to structure (II), the other radical of $R^1$ and $R^2$ is H or $C_{1-12}$-alkyl, and the other radical of $R^3$ and $R^4$ is H or $C_{1-12}$-alkyl;

$R^5$ is $C_{1-12}$-alkyl, $C_{3-8}$-cycloalkyl, —CH₂—$C_{3-8}$-cycloalkyl, aryl, —($C_{1-6}$ alkyl)-aryl, heterocyclyl, —($C_{1-6}$ alkyl)-heterocyclyl or C(=O)$R^{11}$;

$R^7$ is H, $C_{1-8}$-alkyl, aryl, —CN, fluorine, chlorine, bromine, iodine, NO₂, NH₂, NHR¹², NR¹³R¹⁴, OR¹⁸, S(O)$_q$R¹⁹ where q=0, 1 or 2, or C(=O)R²⁰, $R^8$ is H, $C_{1-8}$-alkyl or aryl, or $R^7$ and $R^8$ together form Y, wherein Y is γ'-CR²¹=CR²²—CR²³=CR²⁴-δ', where the end of Y identified by γ' is joined to the atom identified by γ in the compound corresponding to structure (II), and where the end of Y identified by δ' is joined to the atom identified by δ in the compound corresponding to structure (II);

$R^9$ is $C_{1-8}$-alkyl, $C_{3-8}$-cycloalkyl or —CH₂—$C_{3-8}$-cycloalkyl, aryl or —($C_{1-6}$-alklyl)-aryl;

$R^{10}$ is $C_{1-8}$-alkyl, $C_{3-8}$-cycloalkyl or —CH₂—$C_{3-8}$-cycloalkyl, aryl or —($C_{1-6}$-alklyl)-aryl;

$R^{11}$ is H, $C_{1-8}$-alkyl, $C_{3-8}$-cycloalkyl or —CH₂—$C_{3-8}$-cycloalkyl, aryl or OR²⁵;

$R^{12}$ is $C_{1-6}$-alkyl or —CH₂-aryl;

$R^{13}$ and $R^{14}$ are identical or different $C_{1-6}$-alkyl or together are —(CH₂)$_h$- and form a ring where h=4 or 5;

$R^{18}$ is H, $C_{1-8}$-alkyl, $C_{3-8}$-cycloalkyl, —CH₂—$C_{3-8}$-cycloalkyl, aryl or —($C_{1-6}$-alkyl)-aryl;

$R^{19}$ is H, $C_{1-8}$-alkyl, $C_{3-8}$-cycloalkyl, —CH₂—$C_{3-8}$-cycloalkyl, aryl or —($C_{1-6}$-alkyl)-aryl;

$R^{20}$ is H, $C_{1-8}$-alkyl, $C_{3-8}$-cycloalkyl, —CH₂—$C_{3-8}$-cycloalkyl, aryl or —($C_{1-6}$-alkyl)-aryl or OR²⁷;

$R^{21}, R^{22}, R^{23}$ and $R^{24}$ are independently selected from the group consisting of H, fluorine, chlorine, bromine, iodine and OR²⁸;

$R^{25}, R^{26}, R^{27}$ and $R^{28}$ are independently selected from the group consisting of H or $C_{1-6}$-alkyl, where $R^{25}$ is not H when both $R^1$ is aryl and $R^2$ is alkyl; comprising reacting a thiazolamine corresponding to structure (VI),

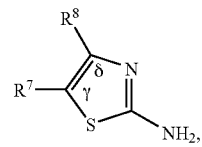
VI wherein $R^7$ and $R^8$ are as defined above in this claim, with the proviso that if $R^7$ and $R^8$ form Y, the end of Y identified by γ' is coupled to the atom of the thiazolamine of the general structure (VI) identified by γ and the end of Y identified by δ' is coupled to the atom of the thiazolamine of the general structure (VI) identified by δ, in the presence of an acid, with an aldehyde corresponding to structure (IV)

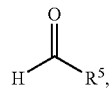
IV wherein $R^5$ is as defined above in this claim, and with an olefin corresponding to structure (V)

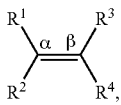
V wherein $R^1, R^2, R^3$ and $R^4$ are as defined above in this claim, with the proviso that if one of the radicals $R^1$ and $R^2$ together with one of the radicals $R^3$ and $R^4$ form W, the end of W identified by α' is joined to the α-carbon atom of the olefin corresponding to structure (V) and the end of W identified by β' is joined to the β-carbon atom of the olefin corresponding to structure (V).

33. A process according to claim 32, wherein the reaction of the heterocyclylamine corresponding to structure (VI) with the aldehyde corresponding to structure (IV) and with the olefin corresponding to structure (V) is carried out in a one-pot process.

34. A process according to claim 32, wherein the acid is trifluoroacetic acid.

35. A process according to claim 32, wherein the reaction is carried out in an organic solvent at a temperature of 0° to 100° C. and at a reaction time of 0.25 to 12 hours.

36. A process according claim 32, wherein the reaction is carried out at a temperature of 15° to 40° C.

37. A substance library containing at least one compound corresponding to structure (I A), (I B) or (II)

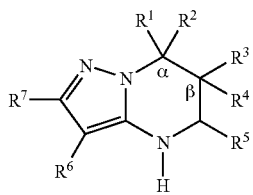
IA
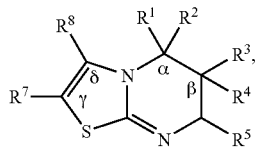
II
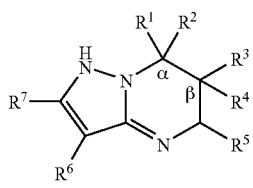
IB
wherein
R$^1$, R$^2$, R$^3$, R$^4$, R$^5$, R$^6$, R$^7$ and R$^8$ are as defined in claim 1.
* * * * *